United States Patent
Calhoun et al.

(10) Patent No.: US 10,668,258 B1
(45) Date of Patent: Jun. 2, 2020

(54) INTRAVASCULAR DEVICES, SYSTEMS, AND METHODS TO ADDRESS EYE DISORDERS

(71) Applicant: J.D. Franco & Co., LLC, Plano, TX (US)

(72) Inventors: Michael Calhoun, Lighthouse Point, FL (US); Stephen Michael, Maple Grove, MN (US); Zachary Tegels, Minneapolis, MN (US)

(73) Assignee: J.D. Franco & Co., LLC, Plano, TX (US)

( * ) Notice: Subject to any disclaimer, the term of this patent is extended or adjusted under 35 U.S.C. 154(b) by 0 days.

(21) Appl. No.: 16/698,560

(22) Filed: Nov. 27, 2019

Related U.S. Application Data

(60) Provisional application No. 62/908,955, filed on Oct. 1, 2019, provisional application No. 62/900,891, filed
(Continued)

(51) Int. Cl.
*A61M 25/10* (2013.01)
*A61M 29/02* (2006.01)
(Continued)

(52) U.S. Cl.
CPC ......... *A61M 25/104* (2013.01); *A61B 5/0066* (2013.01); *A61M 25/09* (2013.01);
(Continued)

(58) Field of Classification Search
CPC ........ A61B 17/12109; A61B 17/12136; A61B 17/12045; A61B 2017/12127;
(Continued)

(56) References Cited

U.S. PATENT DOCUMENTS 2,690,595 A 10/1954 Raiche
3,367,101 A 2/1968 Garnet et al.
(Continued)

FOREIGN PATENT DOCUMENTS

WO WO 98/52639 A1 11/1998
WO WO 98/53761 A1 12/1998
(Continued)

OTHER PUBLICATIONS

Altinbas, N.K. et al, "Effect of Carotid Artery Stenting on Ophthalmic Artery Flow Patterns," Journal of Ultrasound Medicine, 2014; 33: pp. 629-638.
(Continued)

*Primary Examiner* — Katherine M Shi
(74) *Attorney, Agent, or Firm* — Bookoff McAndrews, PLLC

(57) ABSTRACT

A method may include accessing an artery in communication with an ophthalmic artery of a subject, and advancing a microcatheter along the accessed artery so as to align a distal end of the microcatheter with an ostium of the ophthalmic artery, wherein the microcatheter includes a lumen having a guidewire positioned therein. In addition, the method includes proximally withdrawing the guidewire relative to the microcatheter so as to enable a distal portion of the microcatheter to assume a curved relaxed configuration, and cannulating the ostium with the distal portion of the microcatheter when the distal portion is in the curved relaxed configuration.

20 Claims, 55 Drawing Sheets

Related U.S. Application Data on Sep. 16, 2019, provisional application No. 62/832,437, filed on Apr. 11, 2019, provisional application No. 62/786,574, filed on Dec. 31, 2018.

(51) Int. Cl.
*A61M 25/09* (2006.01)
*A61B 5/00* (2006.01)
*A61M 25/06* (2006.01)
*A61M 25/01* (2006.01)

(52) U.S. Cl.
CPC ......... *A61M 29/02* (2013.01); *A61M 25/0662* (2013.01); *A61M 2025/0183* (2013.01); *A61M 2025/1079* (2013.01); *A61M 2210/12* (2013.01)

(58) Field of Classification Search
CPC A61B 2017/22001; A61B 2017/22038; A61B 2017/22041; A61B 2017/22048; A61B 2017/22054; A61B 2017/22067; A61B 2017/22069; A61B 2017/22071; A61F 9/007; A61F 2002/821; A61F 9/00781; A61M 2025/1052; A61M 25/104; A61M 2025/1015
See application file for complete search history.

(56) References Cited

U.S. PATENT DOCUMENTS

| | | |
|---|---|---|
| 3,435,826 A | 4/1969 | Fogarty |
| 4,224,929 A | 9/1980 | Furihata |
| 4,403,612 A | 9/1983 | Fogarty |
| 4,445,897 A | 5/1984 | Ekbladh et al. |
| 4,794,931 A | 1/1989 | Yock |
| 4,857,045 A | 8/1989 | Rydell |
| 4,886,061 A | 12/1989 | Fischell et al. |
| 4,894,051 A | 1/1990 | Shiber |
| 4,898,575 A | 2/1990 | Fischell et al. |
| 4,926,858 A | 5/1990 | Gifford, III et al. |
| 4,936,835 A | 6/1990 | Haaga |
| 4,950,277 A | 8/1990 | Faar |
| 4,957,482 A | 9/1990 | Shiber |
| 4,979,939 A | 12/1990 | Shiber |
| 4,986,807 A | 1/1991 | Faar |
| 5,000,185 A | 3/1991 | Yock |
| 5,000,734 A | 3/1991 | Boussignac et al. |
| 5,007,896 A | 4/1991 | Shiber |
| 5,019,088 A | 5/1991 | Faar |
| 5,024,651 A | 6/1991 | Shiber |
| 5,026,384 A | 6/1991 | Farr et al. |
| 5,087,265 A | 2/1992 | Summers |
| 5,100,425 A | 3/1992 | Fischell et al. |
| 5,135,531 A | 8/1992 | Shiber |
| 5,176,693 A | 1/1993 | Pannek, Jr. |
| 5,292,332 A | 3/1994 | Lee |
| 5,313,949 A | 5/1994 | Yock |
| 5,314,438 A | 5/1994 | Shturman |
| 5,318,576 A | 6/1994 | Plassche et al. |
| 5,336,234 A | 8/1994 | Vigil et al. |
| 5,366,464 A | 11/1994 | Belknap |
| 5,395,311 A | 3/1995 | Andrews |
| 5,402,790 A | 4/1995 | Jang et al. |
| 5,409,454 A | 4/1995 | Fischell et al. |
| 5,415,634 A | 5/1995 | Glynn et al. |
| 5,419,761 A | 5/1995 | Narayanan et al. |
| 5,507,292 A | 4/1996 | Jang et al. |
| 5,554,119 A | 9/1996 | Harrison et al. |
| 5,709,701 A | 1/1998 | Parodi |
| 5,820,595 A | 10/1998 | Parodi |
| 5,897,567 A | 4/1999 | Ressemann et al. |
| 5,951,514 A | 9/1999 | Sahota |
| 5,972,019 A | 10/1999 | Engelson et al. |
| 6,010,522 A | 1/2000 | Barbut et al. |
| 6,146,370 A | 11/2000 | Barbut |
| 6,206,868 B1 | 3/2001 | Parodi |
| 6,302,908 B1 | 10/2001 | Parodi |
| 6,336,933 B1 | 1/2002 | Parodi |
| 6,344,054 B1 | 2/2002 | Parodi |
| 6,413,235 B1 | 7/2002 | Parodi |
| 6,423,032 B2 | 7/2002 | Parodi |
| 6,494,890 B1 | 12/2002 | Shturman et al. |
| 6,540,712 B1 | 4/2003 | Parodi et al. |
| 6,595,980 B1 | 7/2003 | Barbut |
| 6,623,471 B1 | 9/2003 | Barbut |
| 6,626,861 B1 | 9/2003 | Hart et al. |
| 6,641,573 B1 | 11/2003 | Parodi |
| 6,645,222 B1 | 11/2003 | Parodi et al. |
| 6,824,558 B2 | 11/2004 | Parodi |
| 6,827,726 B2 | 12/2004 | Parodi |
| 6,837,881 B1 | 1/2005 | Barbut |
| 6,855,162 B2 | 2/2005 | Parodi |
| 6,902,540 B2 | 6/2005 | Dorros et al. |
| 6,905,490 B2 | 6/2005 | Parodi |
| 6,908,474 B2 | 6/2005 | Hogendijk et al. |
| 6,929,634 B2 | 8/2005 | Dorros et al. |
| 6,936,053 B1 | 8/2005 | Weiss |
| 6,936,060 B2 | 8/2005 | Hogendijk et al. |
| 6,974,469 B2 | 12/2005 | Broome et al. |
| 7,214,201 B2 | 5/2007 | Burmeister et al. |
| 7,235,095 B2 | 6/2007 | Haverkost et al. |
| 7,309,334 B2 | 12/2007 | Von Hoffmann |
| 7,384,411 B1 | 6/2008 | Condado |
| 7,604,612 B2 | 10/2009 | Ressemann et al. |
| 7,806,906 B2 | 10/2010 | Don Michael |
| 7,867,273 B2 | 1/2011 | Pappas et al. |
| 7,901,445 B2 | 3/2011 | Wallace et al. |
| 7,927,347 B2 | 4/2011 | Hogendijk et al. |
| 8,123,779 B2 | 2/2012 | Demond et al. |
| 8,157,760 B2 | 4/2012 | Criado et al. |
| 8,267,956 B2 | 9/2012 | Salahieh et al. |
| 8,353,850 B2 | 1/2013 | Ressemann et al. |
| 8,409,237 B2 | 4/2013 | Galdonik et al. |
| 8,414,516 B2 | 4/2013 | Chang |
| 8,439,937 B2 | 5/2013 | Montague et al. |
| 8,545,432 B2 | 10/2013 | Renati et al. |
| 8,834,404 B2 | 9/2014 | Beaudin |
| 8,852,226 B2 | 10/2014 | Gilson et al. |
| 8,863,631 B1 | 10/2014 | Janardhan et al. |
| 9,078,682 B2 | 7/2015 | Lenker et al. |
| 9,241,699 B1 | 1/2016 | Kume et al. |
| 9,259,215 B2 | 2/2016 | Chou et al. |
| 9,265,512 B2 | 2/2016 | Garrison et al. |
| 9,987,164 B2 | 6/2018 | Calhoun |
| 10,195,077 B2 | 2/2019 | Calhoun et al. |
| 10,265,085 B2 | 4/2019 | Zaidat |
| 10,342,699 B2 | 7/2019 | Calhoun et al. |
| 2001/0001114 A1 | 5/2001 | Tsugita et al. |
| 2002/0077656 A1 | 6/2002 | Ginn et al. |
| 2002/0087128 A1 | 7/2002 | Paques et al. |
| 2002/0143291 A1 | 10/2002 | Slater |
| 2002/0151922 A1 | 10/2002 | Hogendijk et al. |
| 2002/0165573 A1 | 11/2002 | Barbut |
| 2003/0023200 A1 | 1/2003 | Barbut et al. |
| 2003/0023227 A1 | 1/2003 | Zadno-Azizi et al. |
| 2003/0199802 A1 | 10/2003 | Barbut |
| 2003/0199819 A1 | 10/2003 | Beck |
| 2003/0203958 A1 | 10/2003 | Kunz et al. |
| 2005/0149117 A1 | 7/2005 | Khosravi et al. |
| 2006/0136022 A1 | 6/2006 | Wong, Jr. et al. |
| 2006/0259132 A1 | 11/2006 | Schaffer et al. |
| 2007/0026035 A1 | 2/2007 | Burke et al. |
| 2008/0027519 A1 | 1/2008 | Guerrero |
| 2008/0243229 A1 | 10/2008 | Wallace et al. |
| 2009/0018455 A1 | 1/2009 | Chang |
| 2009/0024072 A1 | 1/2009 | Criado et al. |
| 2009/0030323 A1 | 1/2009 | Fawzi et al. |
| 2009/0221961 A1 | 9/2009 | Tal et al. |
| 2010/0076365 A1 | 3/2010 | Riina et al. |
| 2010/0100045 A1 | 4/2010 | Pravongviengkham et al. |
| 2010/0125244 A1 | 5/2010 | McAndrew |
| 2010/0234884 A1 | 9/2010 | Lafontaine et al. |
| 2011/0143993 A1 | 6/2011 | Langer et al. |

(56) References Cited

U.S. PATENT DOCUMENTS

| | | |
|---|---|---|
| 2011/0152683 A1 | 6/2011 | Gerrans et al. |
| 2011/0152998 A1 | 6/2011 | Berez et al. |
| 2011/0160762 A1 | 6/2011 | Hogendijk et al. |
| 2011/0274748 A1 | 11/2011 | Robinson et al. |
| 2012/0046679 A1 | 2/2012 | Patel et al. |
| 2012/0078287 A1 | 3/2012 | Barbut |
| 2012/0101510 A1 | 4/2012 | Lenker et al. |
| 2013/0035628 A1 | 2/2013 | Garrison et al. |
| 2013/0197621 A1 | 8/2013 | Ryan et al. |
| 2013/0281788 A1 | 10/2013 | Garrison |
| 2014/0154246 A1 | 6/2014 | Robinson et al. |
| 2014/0222066 A1 | 8/2014 | Tegels |
| 2015/0032121 A1 | 1/2015 | Janardhan et al. |
| 2015/0065804 A1 | 3/2015 | Kleyman |
| 2015/0272732 A1 | 10/2015 | Tilson et al. |
| 2015/0313607 A1 | 11/2015 | Zhadkevich |
| 2015/0359549 A1 | 12/2015 | Lenker et al. |
| 2015/0366580 A1 | 12/2015 | Lenihan et al. |
| 2016/0166754 A1 | 6/2016 | Kassab et al. |
| 2016/0317328 A1 | 11/2016 | Berez et al. |
| 2017/0164963 A1 | 6/2017 | Goyal |
| 2017/0326001 A1 | 11/2017 | Franco et al. |
| 2017/0348120 A1 | 12/2017 | Calhoun et al. |
| 2018/0132876 A1 | 5/2018 | Zaidat |
| 2018/0317944 A1* | 11/2018 | Calhoun ............... A61B 17/22 |

FOREIGN PATENT DOCUMENTS

| | | |
|---|---|---|
| WO | WO 00/54673 A1 | 9/2000 |
| WO | WO 03/018085 A2 | 3/2003 |
| WO | WO 2007/103464 A2 | 9/2007 |
| WO | WO 2014/022866 A1 | 2/2014 |
| WO | WO 2016/109586 A1 | 7/2016 |
| WO | WO 2017/156333 A1 | 9/2017 |
| WO | WO 2018/053121 A1 | 3/2018 |
| WO | WO 2018/106858 A1 | 6/2018 |

OTHER PUBLICATIONS

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Paques, M. et al., "Superselective ophthalmic artery fibrinolytic therapy for the treatment of central retinal vein occlusion." British Journal of Ophthalmology, 2000, 84: 1387-1391.

Tan, P.L. et al., "AMD and the alternative complement pathway: genetics and functional implications," Human Genomics, 2016, 10:23, 13 pages.

Xu, H. et al., "Targeting the complement system for the management of retinal inflammatory and degenerative diseases," European Journal of Pharmacology, 2016, 787, pp. 94-104.

Yamane, T. et al., "The technique of ophthalmic arterial infusion therapy for patients with intraocular retinoblastoma," International Journal of Clinical Oncology, Apr. 2004; vol. 9, Issue 2, pp. 69-73.

Zeumer, H. et al., "Local intra-arterial fibrinolytic therapy in patients with stroke: urokinase versus recombinant tissue plagminogen activator (r-TPA)," Neuroradiology, 1993; 35: pp. 159-162.

Zipfel, P.F., et al., "The Role of Complement in AMD," Inflammation and Retinal Disease: Complement Biology and Pathology, Advances in Experimental Medicine and Biology, 2010, 703, pp. 9-24.

Examination Report No. 2 for AU Application No. 2013296195, dated Jun. 27, 2017 (6 pages).

Notice of Allowance for KR 20157005602, dated Sep. 25, 2017 (3 pages).

Loh, K. et al., "Prevention and management of vision loss relating to facial filler injections." Singapore Medical Journal, 2016; 57(8): 438-443.

International Search Report and Written Opinion for International Application No. PCT/US2017/051551, dated Dec. 15, 2017 (14 pages).

International Search Report and Written Opinion for International Application No. PCT/US2017/052901, dated Dec. 8, 2017 (9 pages).

Bird, B. et al., "Anatomy, Head and Neck, Ophthalmic Arteries," NCBI Bookshelf, a service of the National Library of Medicine, National Institutes of Health, Oct. 27, 2018, 5 pages. www.ncbi.nlm.nih.gov/books/NBK482317/.

Hattenbach, L. et al., "Experimental Endoscopic Endovascular Cannulation: A Novel Approach to Thrombolysis in Retinal Vessel Occlusion," Investigative Ophthalmology & Visual Science, Jan. 2012, vol. 53, No. 1, pp. 42-46.

Khan, T.T. et al., "An Anatomical Analysis of the Supratrochlear Artery: Considerations in Facial Filler Injections and Preventing Vision Loss," Aesthetic Surgery Journal, 2017, vol. 37(2), pp. 203-208.

Schumacher, M. et al., "Intra-arterial fibrinolytic therapy in central retinal artery occlusion," Neuroradiology (1993) 35: pp. 600-605.

Schwenn, O.K. et al., "Experimental Percutaneous Cannulation of the Supraorbital Arteries: Implication for Future Therapy," Investigative Ophthalmology & Visual Science, May 2005, vol. 46, No. 5, pp. 1557-1560.

Wang, R. et al., "Evaluation of Ophthalmic Artery Branch Retrograde Intervention in the Treatment of Central Retinal Artery Occlusion (CRAO)," Medical Science Monitor, 2017, 23: pp. 114-120.

Zhao, W. et al. "Three-Dimensional Computed Tomographic Study on the Periorbital Branches of the Ophthalmic Artery: Arterial Variations and Clinical Relevance," Aesthetic Surgery Journal, 2018, pp. 1-9.

International Search Report and Written Opinion for corresponding PCT/US2013/053670, dated Dec. 26, 2013 (16 pp.).

Hayreh et al. "Ocular Arterial Occlusive Disorders and Carotid Artery Disease," American Academy of Ophthalmology, 2017; vol. 1, No. 1: pp. 12-18.

Hayreh et al. "The Ophthalmic Artery," British Journal of Ophthalmology, 1962; 46, 65: pp. 65-98.

Hayreh, S.S., "The Ophthalmic Artery III. Branches," British Journal of Ophthalmology, 1962, 46, pp. 212-247.

International Search Report and Written Opinion for International Application No. PCT/US2018/031229, dated Jul. 27, 2018 (19 pages).

Mazur et al., Catheterization and Cardiovascular Diagnosis, vol. 31, Issue 1, Abstract (1994).

(56) References Cited

OTHER PUBLICATIONS

Aurboonyawat et al., "Indirect Carotid-Cavernous Sinus Fistulas Treated by Transvenous Approach Through the Superior Ophthalmic Vein: A Case Report and Technical Note," Siriraj Med. J., vol. 59, pp. 191-194, 2007.
Kleintjes, "Forehead anatomy: Arterial variations and venous link of the midline forehead flap," Journal of Plastic, Reconstructive & Aesthetic Surgery, vol. 60, Issue 6, pp. 593-606, 2007.
International Search Report and Written Opinion for International Application No. PCT/US2018/014766, dated Mar. 29, 2018 (7 pages).

* cited by examiner

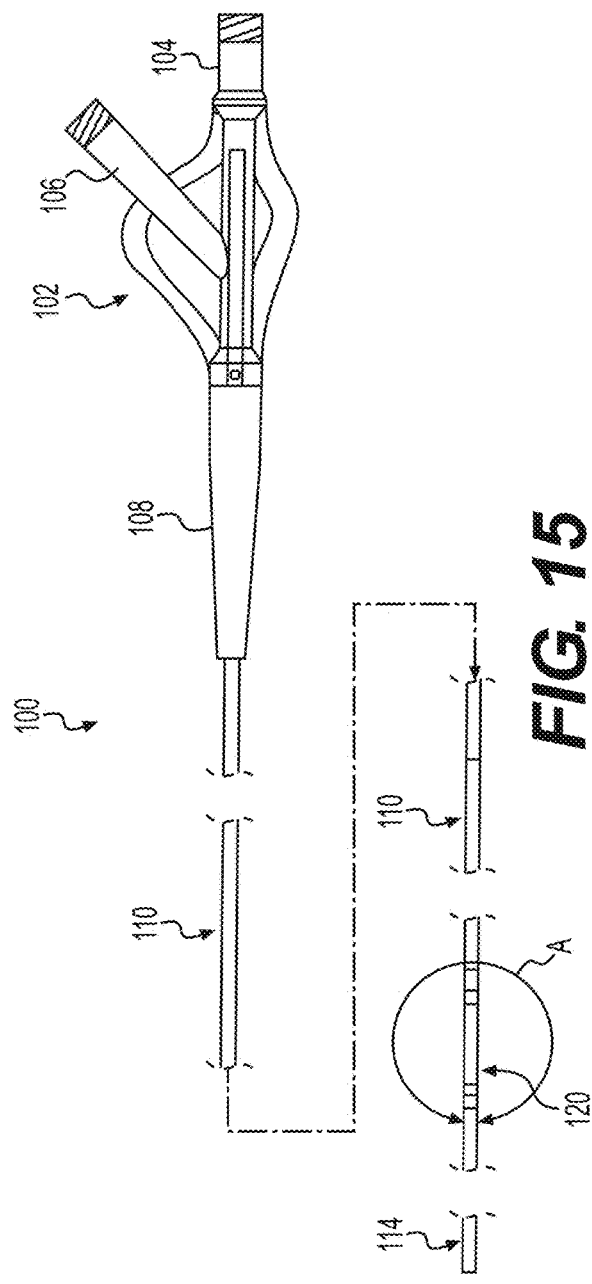
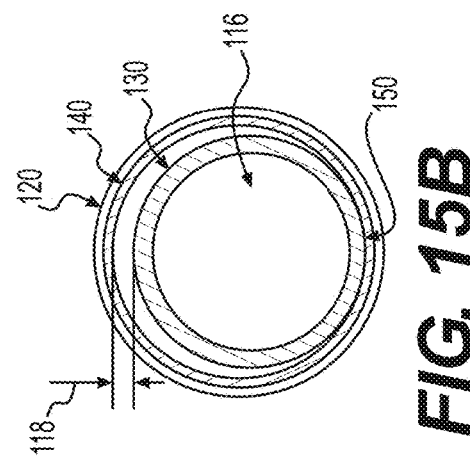
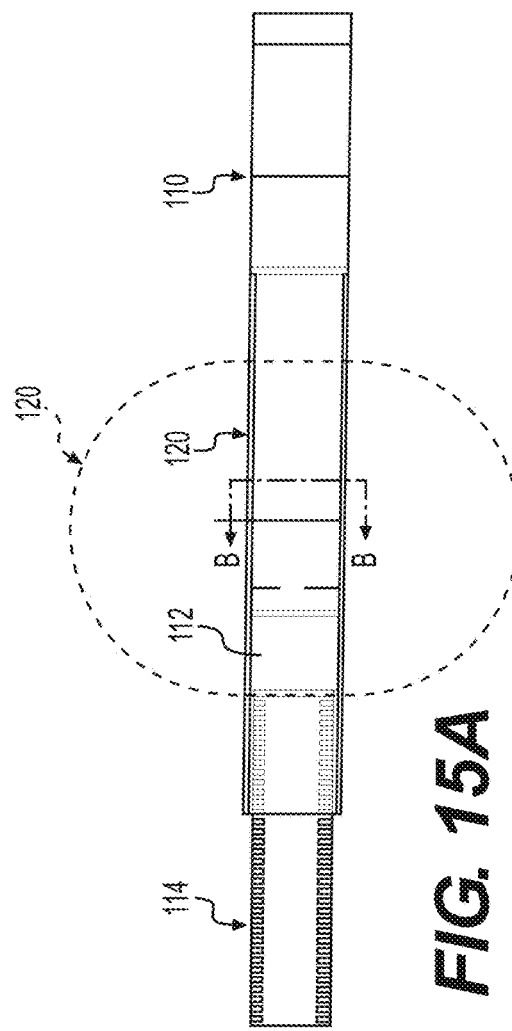

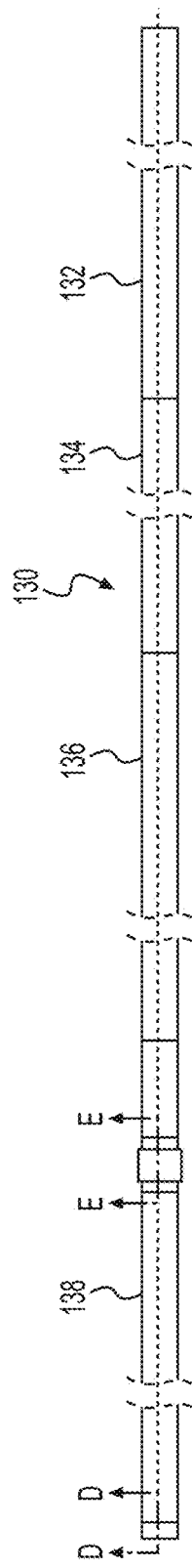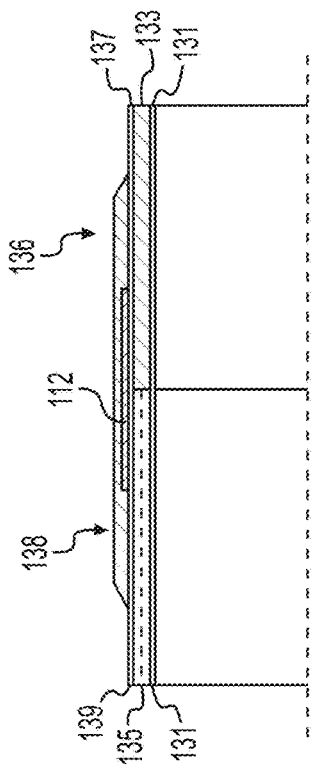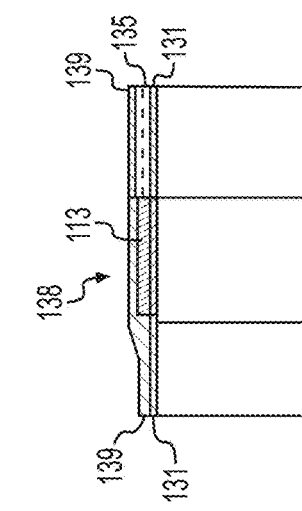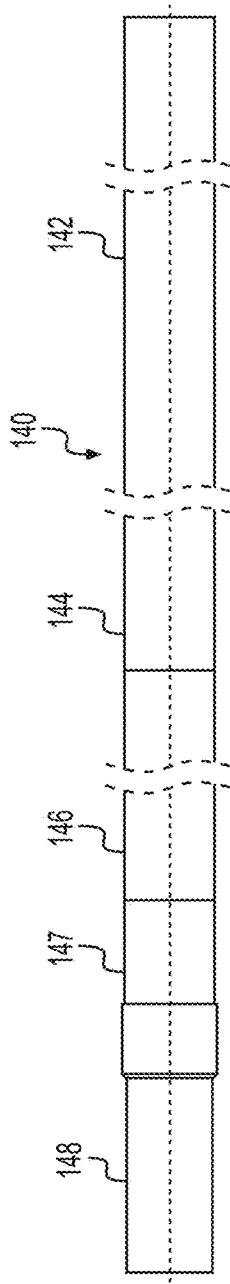

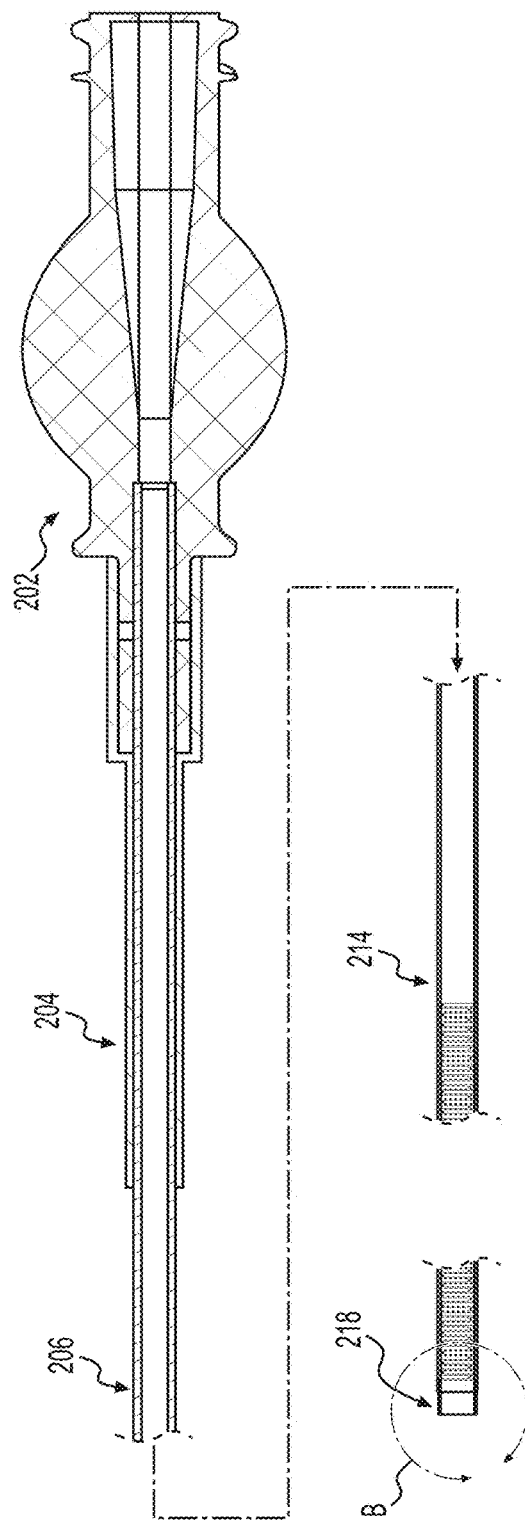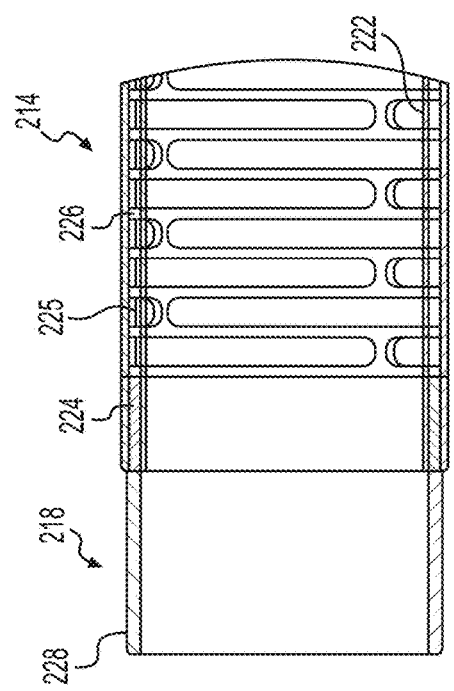

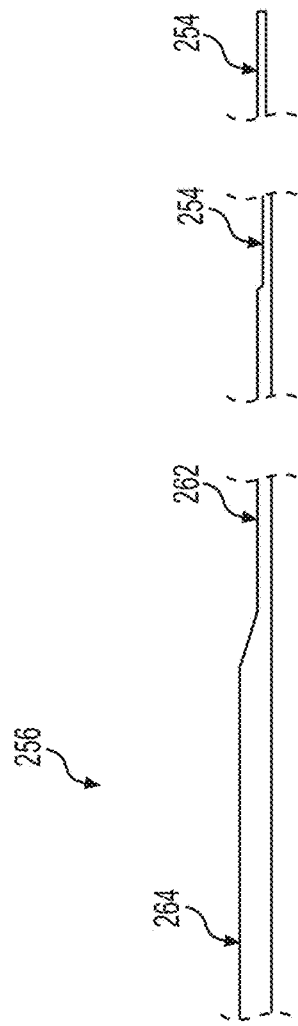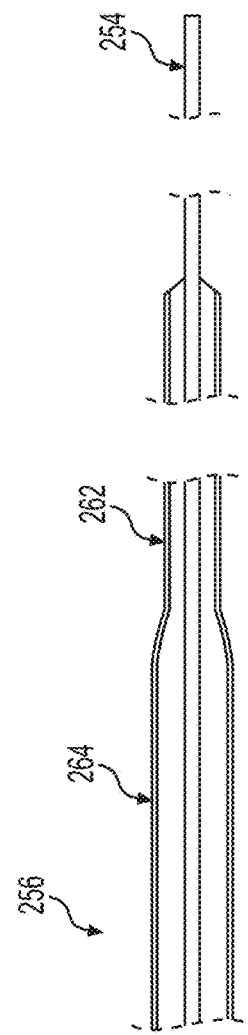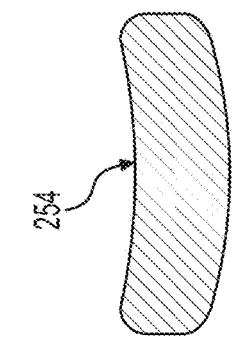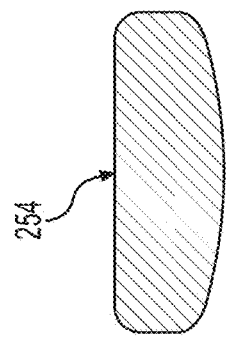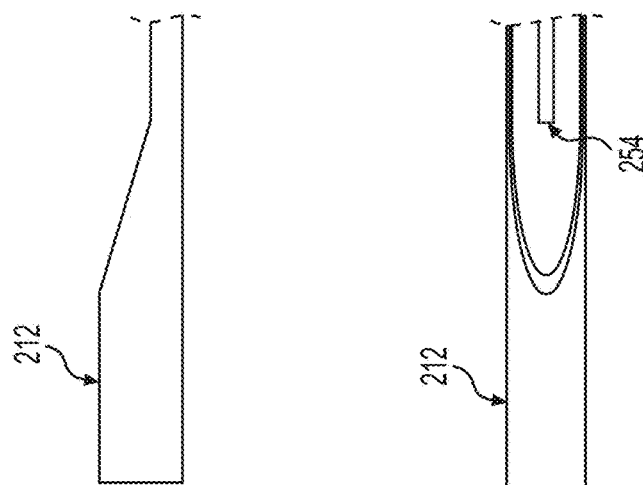

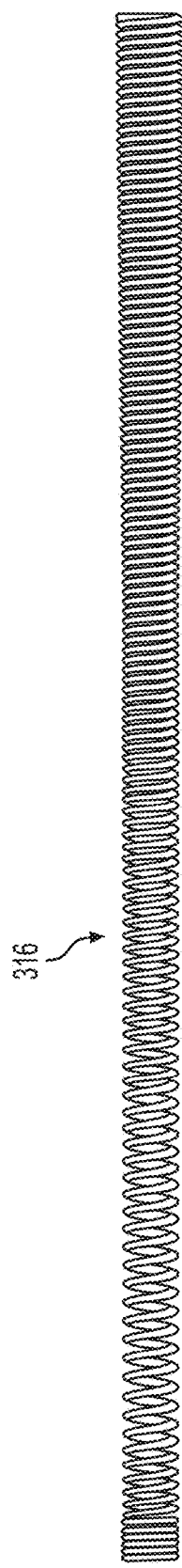
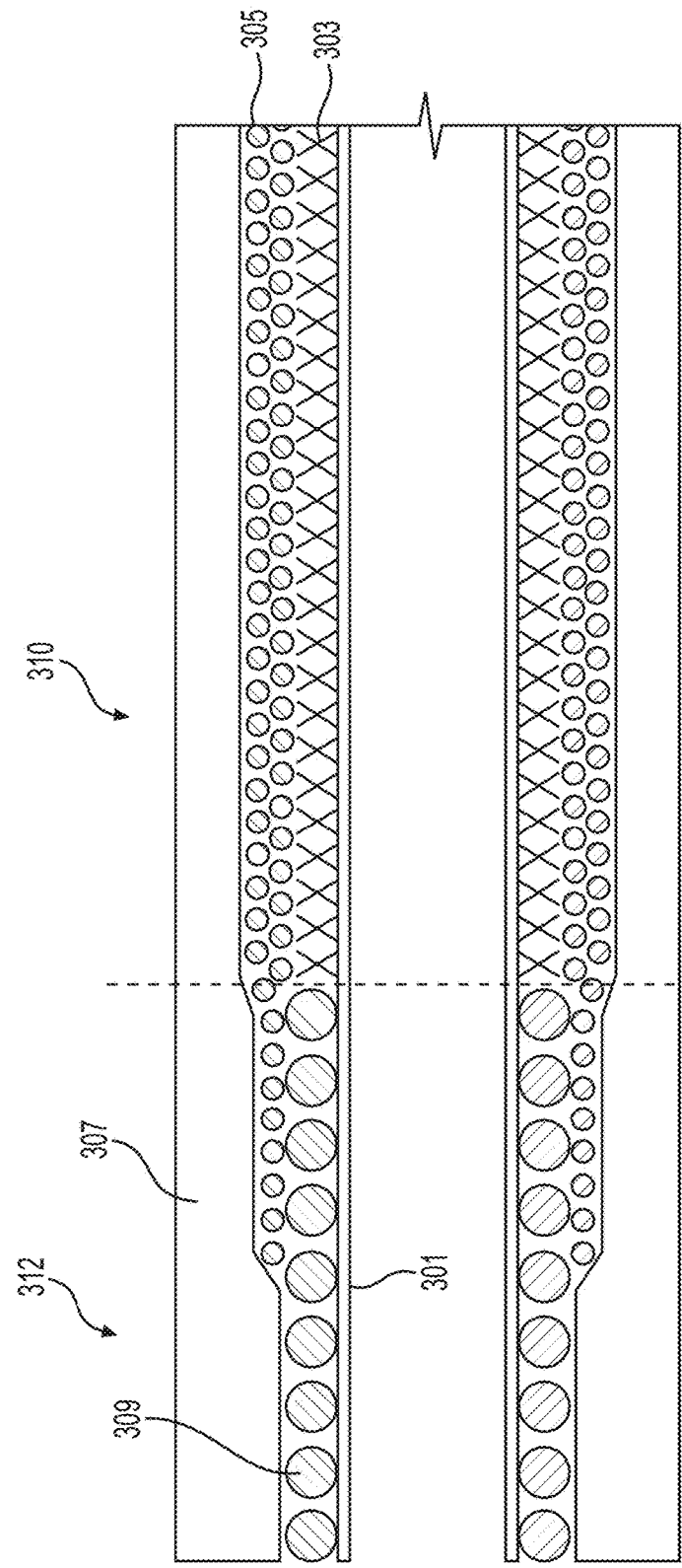
FIG. 17D
FIG. 17E

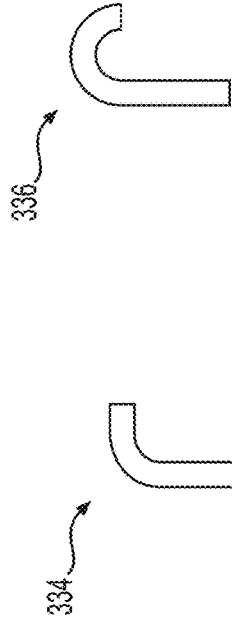
FIG. 18A
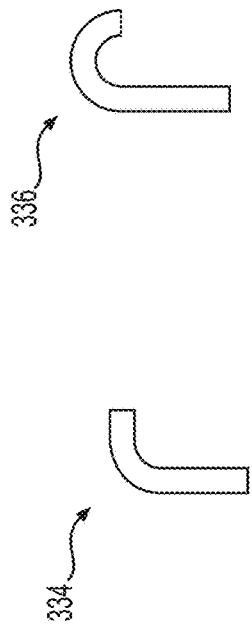
FIG. 18B
FIG. 18C
FIG. 18D
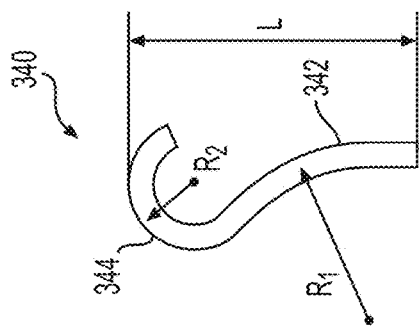
FIG. 18E
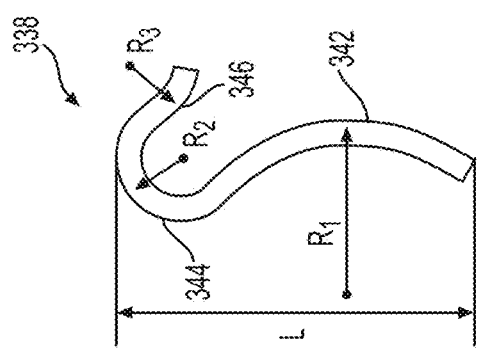
FIG. 18F

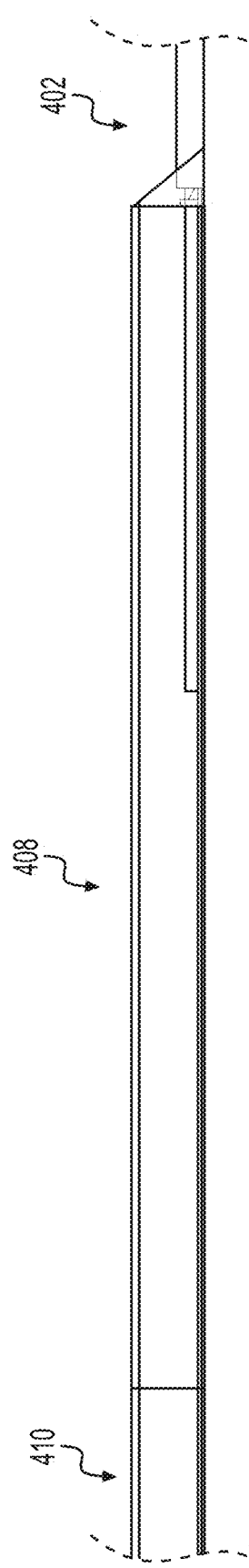

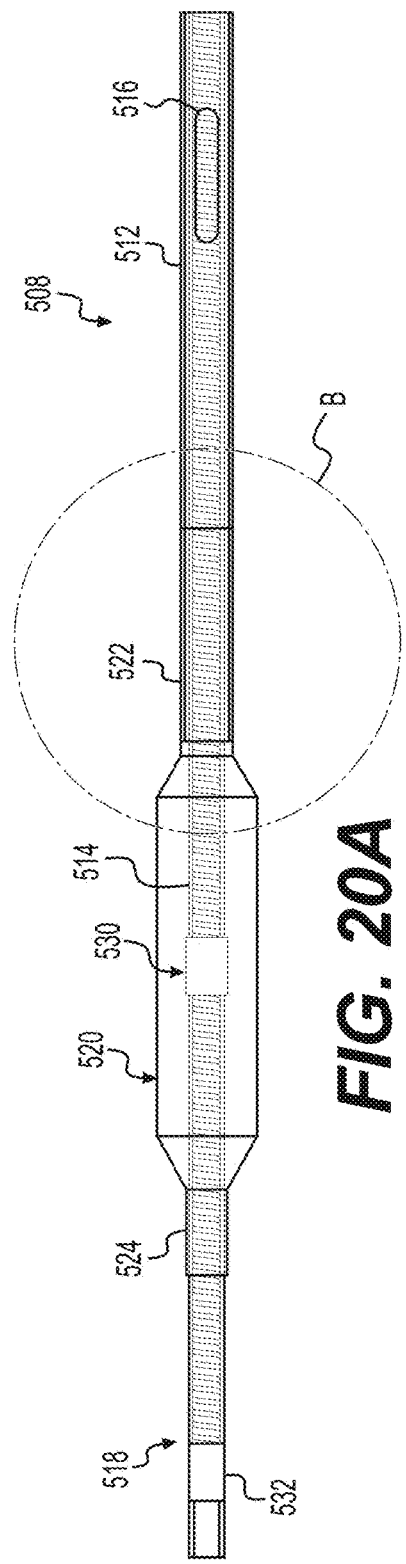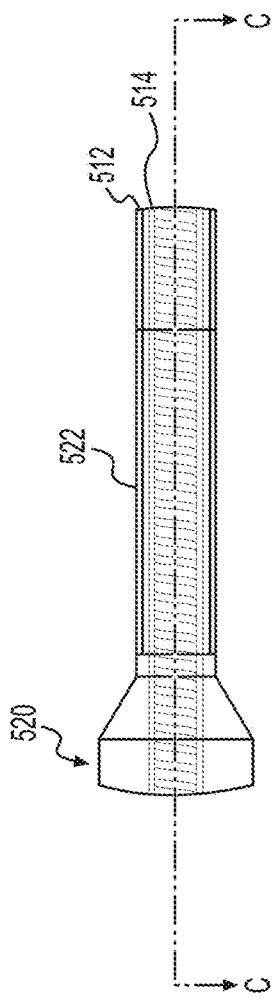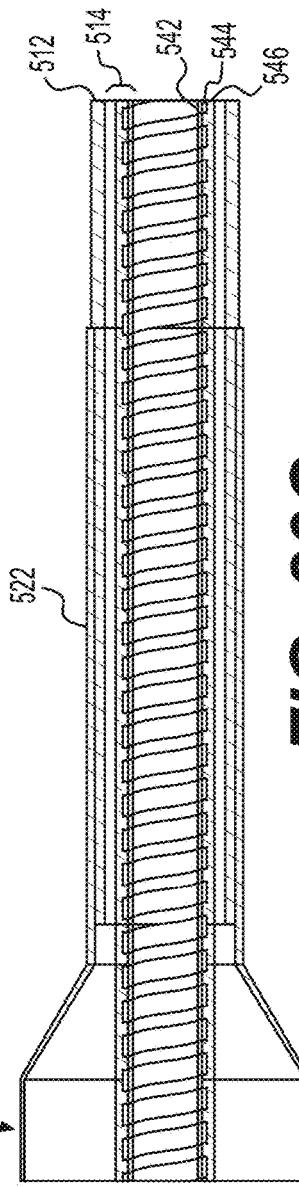

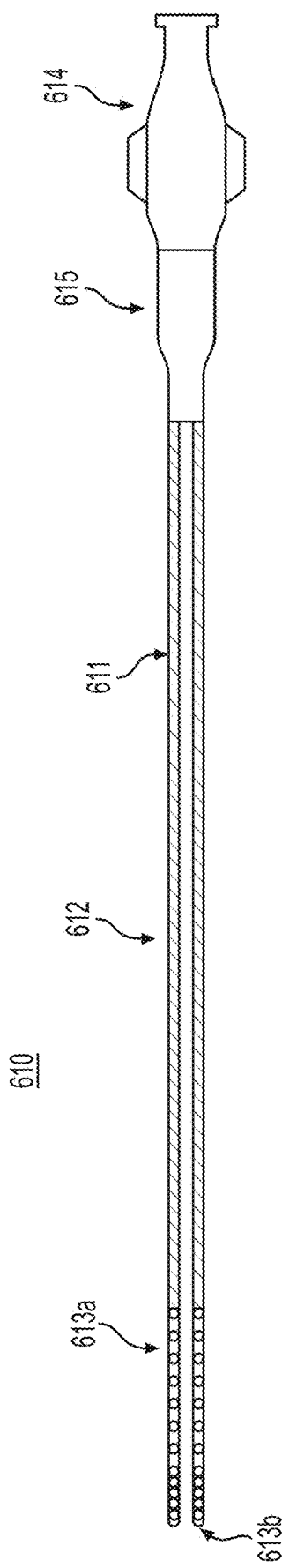
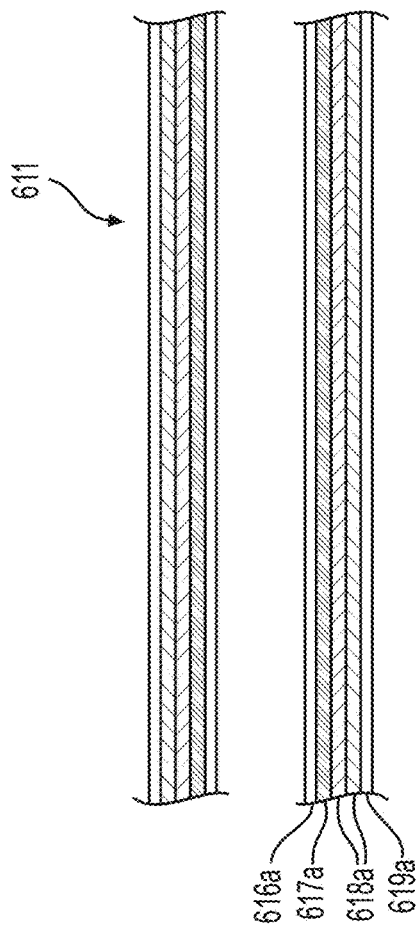
FIG. 21A
FIG. 21B

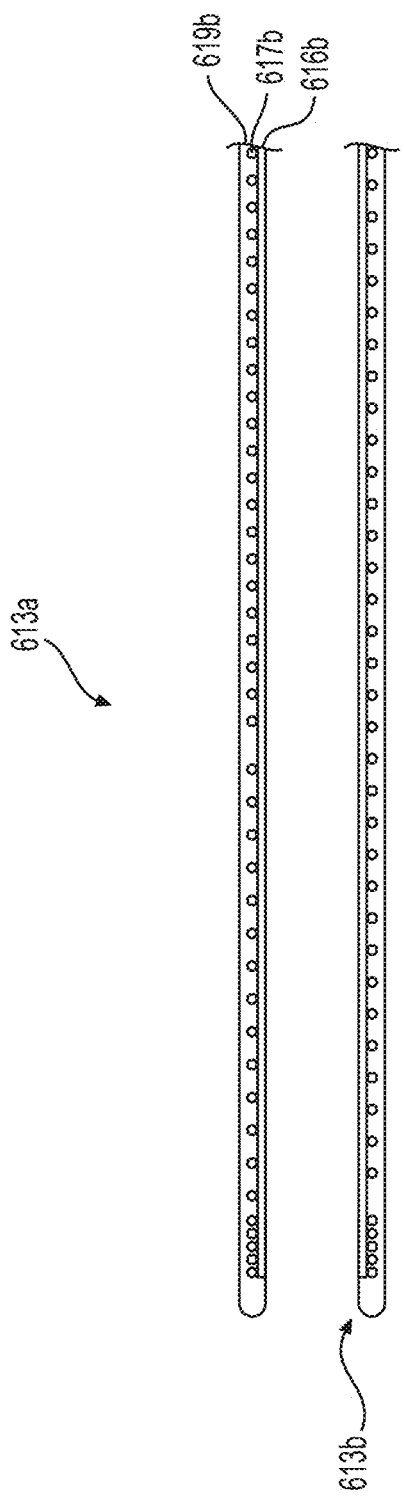
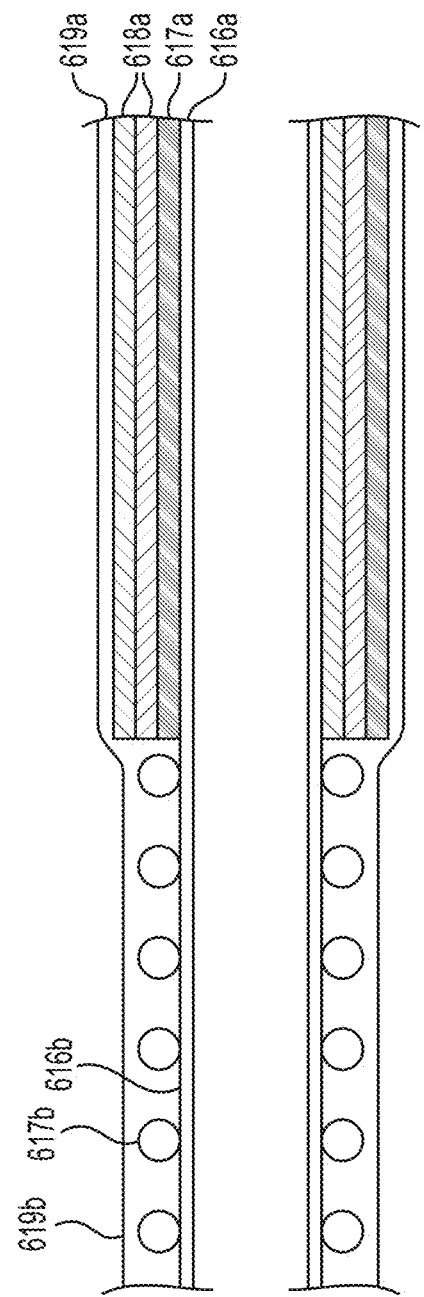
FIG. 21C
FIG. 21D

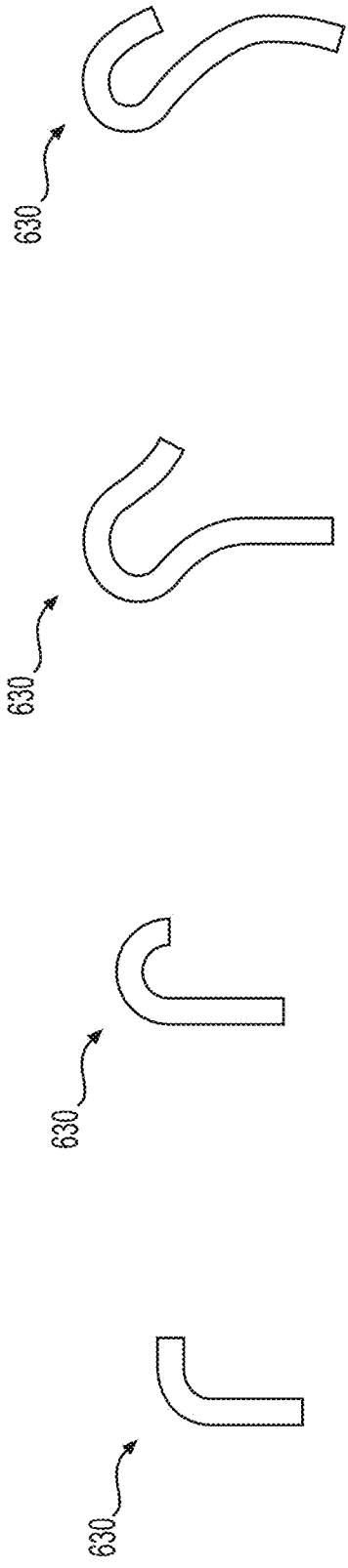
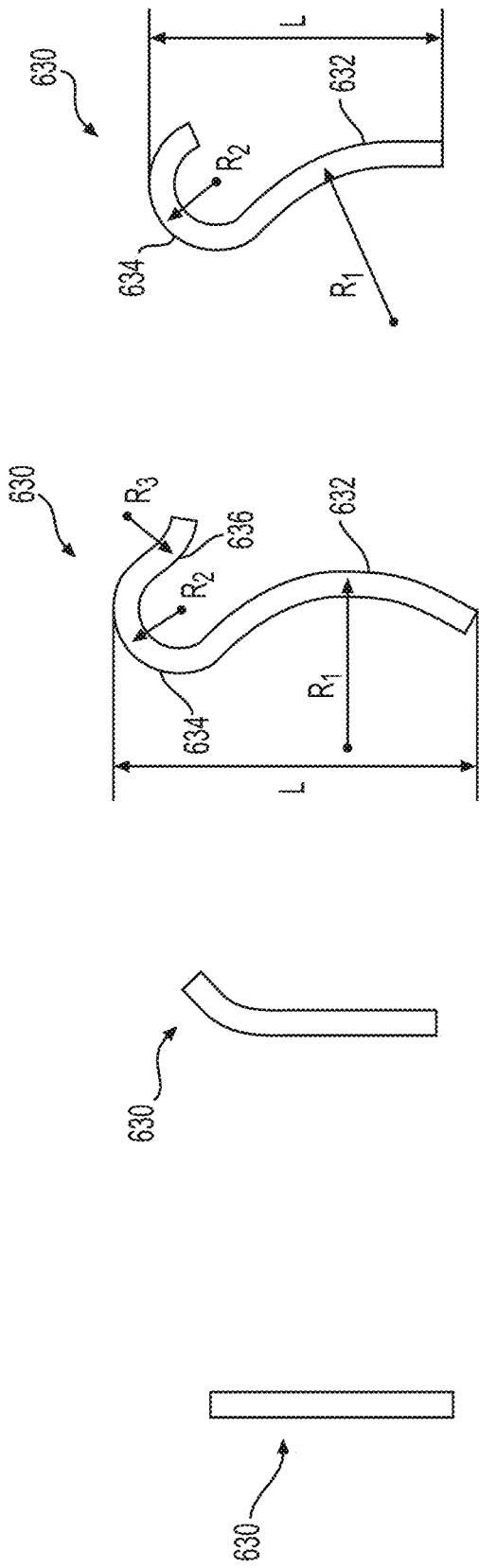
FIG. 23A  FIG. 23B  FIG. 23C  FIG. 23D
FIG. 23E  FIG. 23F  FIG. 23G  FIG. 23H

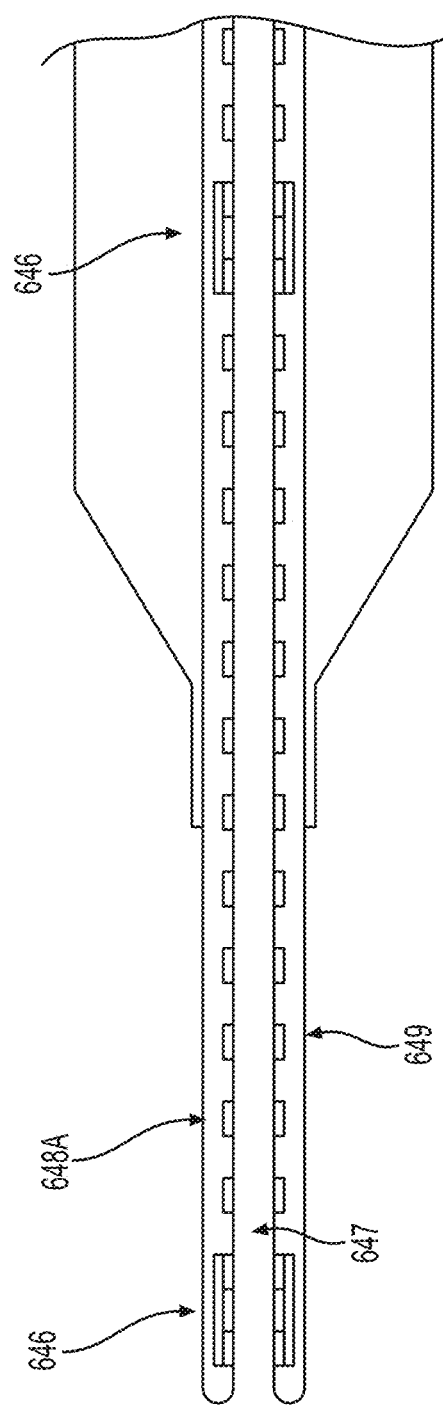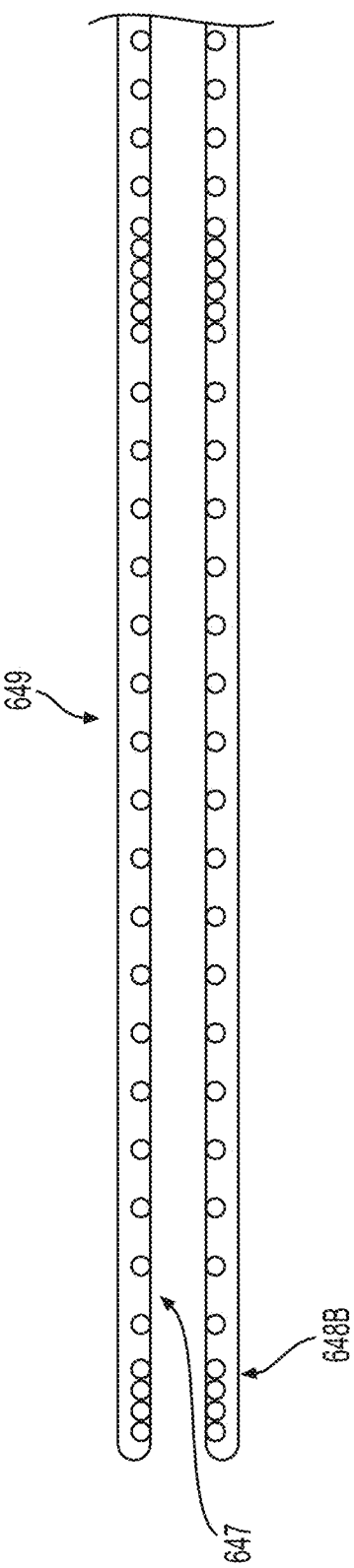
FIG. 24D
FIG. 24E

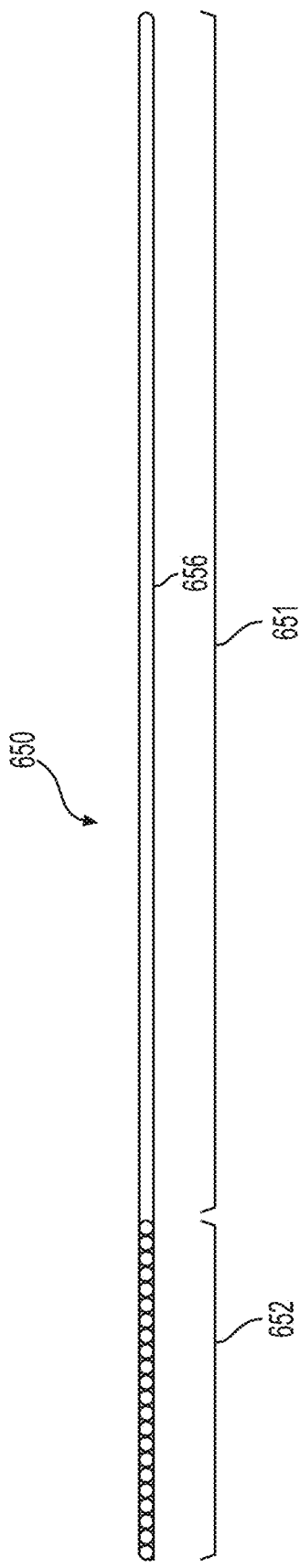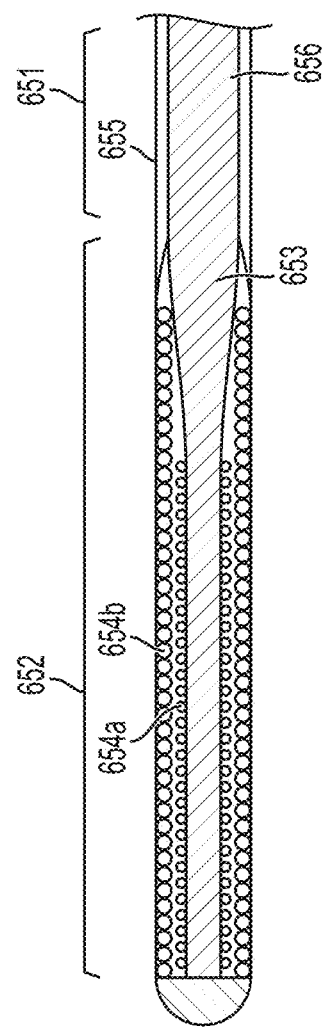
FIG. 25A
FIG. 25B

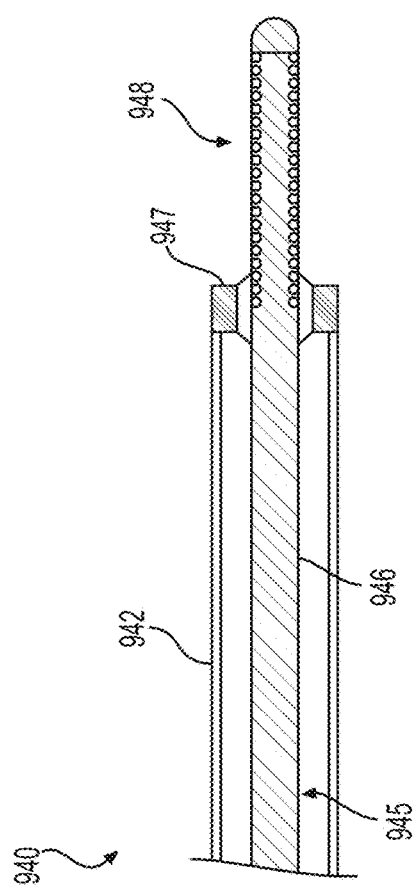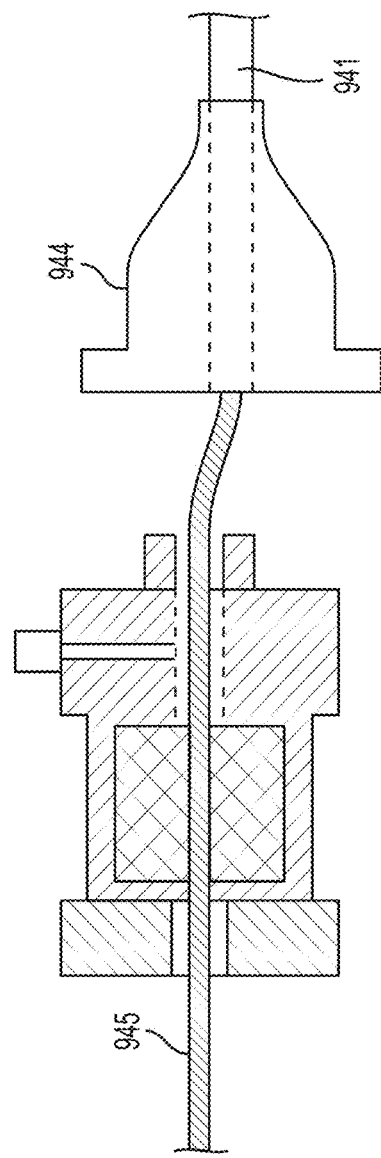
FIG. 35A
FIG. 35B

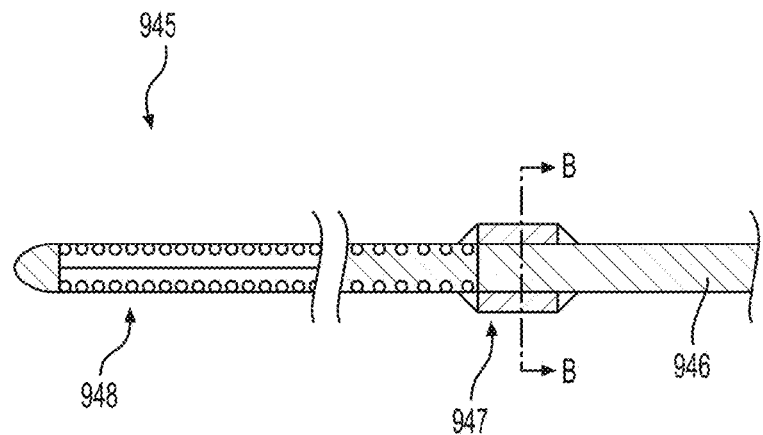
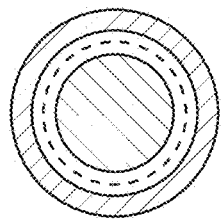
FIG. 35C  FIG. 35D
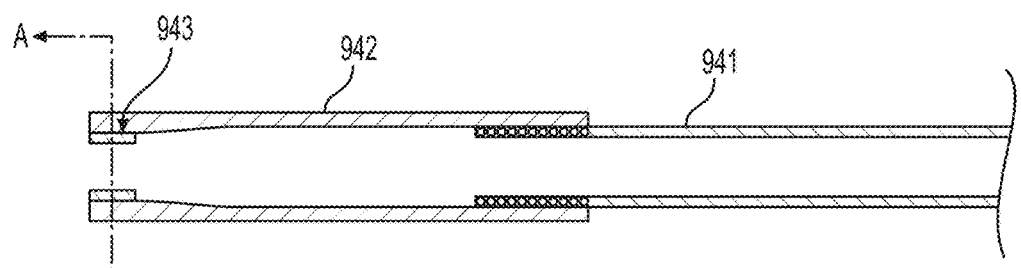
FIG. 35E
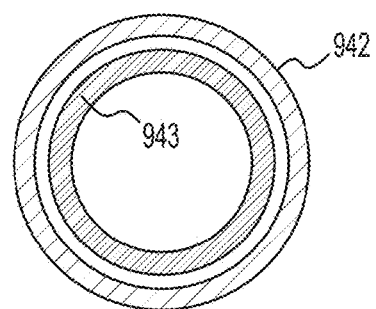
FIG. 35F

INTRAVASCULAR DEVICES, SYSTEMS, AND METHODS TO ADDRESS EYE DISORDERS

CROSS-REFERENCE TO RELATED APPLICATIONS

This application claims the benefit of priority of U.S. Provisional Patent Application No. 62/786,574, filed on Dec. 31, 2018, U.S. Provisional Application No. 62/832,437, filed on Apr. 11, 2019, U.S. Provisional Application No. 62/900,891, filed on Sep. 16, 2019, and U.S. Provisional Application No. 62/908,955, filed on Oct. 1, 2019, each of which is incorporated by reference herein in its entirety.

TECHNICAL FIELD

Aspects of the present disclosure generally relate to intravascular devices, systems and methods to address eye disorders.

BACKGROUND

Accessing and treating the ophthalmic artery is challenging but could address diseases of the eye. Improvements in devices, systems and methods for such purposes are needed.

SUMMARY

Blood is supplied to the eye primarily via the internal carotid artery (ICA), ophthalmic artery (OA) and retinal artery (RA). Disease in any of these arteries, or elsewhere in the arterial path from the heart, may compromise blood supply to the eye and contribute to eye disorders such as age-related macular degeneration (AMD), glaucoma, diabetic retinopathy, among others. Thus, treating such arterial disease may effectively treat the associated eye disorder. The inventors have found that people with AMD often have arterial disease in the ICA, the ostium of the OA as it branches off the ICA, and in the short limb of the OA. The devices, systems and methods described herein are intended to provide improved access and treatment of these vascular targets.

In one embodiment, a method may comprise accessing an oculofacial artery (OFA) at an access site on a face of a patient; advancing a device through OFA access site to an ophthalmic artery (OA); and treating a portion of the OA with the device. In some embodiments, the wherein the OFA comprises the supra-trochlear artery or the supra-orbital artery.

In another embodiment, a method may comprise accessing a superficial temporal artery (STA) near an ear of a patient; advancing a device through STA access site to an ophthalmic artery (OA); and treating a portion of the OA with the device.

In yet another embodiment, a method may comprise accessing a superficial temporal artery (STA) near an ear of a patient; advancing a device through STA access site to a cerebral vascular target; and treating a portion of the cerebral vascular target with the device.

In still another embodiment, a method may comprise accessing a superficial temporal artery (STA) near an ear of a patient; advancing a device through STA access site to a coronary artery target; and treating a portion of the coronary artery target with the device.

Further, in one embodiment, a method may comprise accessing an occipital artery (OcA) near an occipital bone of a patient; advancing a device through OcA access site to an ophthalmic artery (OA); and treating a portion of the OA with the device.

In another embodiment, a method may comprise accessing an occipital artery (OcA) near an occipital bone of a patient; advancing a device through OcA access site to a cerebral vascular target; and treating a portion of the cerebral vascular target with the device.

In yet another embodiment, a method may comprise accessing an occipital artery (OcA) near an occipital bone of a patient; advancing a device through OcA access site to a coronary artery target; and treating a portion of the coronary artery target with the device.

In still another embodiment, a device may include a catheter for insertion through an internal carotid artery (ICA) to reach an ostium of an ophthalmic artery (OA), wherein the ICA includes clinoid segment just proximal of the OA ostium, wherein the clinoid segment includes an inside bend and an outside bend, the catheter comprising: an elongate tubular shaft having a proximal straight portion, a curved distal portion and a distal tip; the curved portion having a primary curve extending from the straight portion and a secondary curve extending from the primary curve; the primary curve having curvature in a first direction, the secondary curve having a curvature in a second direction, wherein the first direction is different than the second direction, wherein, when the distal curved portion is positioned in the ICA, the primary curve engages the outside bend and extends toward the inside bend, and the secondary curve extends from the inside bend toward the OA ostium.

In another embodiment, a device may include a catheter for insertion through an internal carotid artery (ICA) to reach an ostium of an ophthalmic artery (OA), wherein the ICA includes clinoid segment just proximal of the OA ostium, wherein the clinoid segment includes an inside bend and an outside bend, the catheter comprising: an elongate tubular shaft having a proximal straight portion, a curved distal portion and a distal tip; the curved portion having a primary curve extending from the straight portion and a secondary curve extending from the primary curve; the primary curve having curvature in a first direction, the secondary curve having a curvature in a second direction, wherein the first direction is different than the second direction; wherein the primary curve is configured to engage the outside bend and extend towards the inside bend of the clinoid segment when the distal curved portion is positioned in the ICA; and wherein the secondary curve is configured to extend from the inside bend of the clinoid segment toward the OA ostium when the distal curved portion is positioned in the ICA.

In some embodiments, one or more of the following may also apply: the first direction is opposite the second direction, the primary curve and the secondary curve are coplanar, the secondary curve extends from the inside bend to point the distal tip toward the OA ostium, the secondary curve extends from the inside bend to position the distal tip in the OA ostium, the distal tip points at least partially proximally, the primary curve has a radius of curvature of 7.5 to 15 mm and an arc angle of 35 to 55 degrees such that the primary curve has a tighter bend than the inside bend of the clinoid segment, the primary curve has a tighter bend than the inside bend of the clinoid segment, and/or the secondary curve substantially spans the inside bend to the outside bend of the clinoid segment adjacent the OA ostium.

In yet another embodiment, a method may comprise accessing an artery in communication with an ophthalmic artery of a subject; advancing a microcatheter along the accessed artery so as to align a distal end of the microcatheter with an ostium of the ophthalmic artery, wherein the microcatheter includes a lumen having a guidewire positioned therein; proximally withdrawing the guidewire relative to the microcatheter so as to enable a distal portion of the microcatheter to assume a curved relaxed configuration; and cannulating the ostium with the distal portion of the microcatheter when the distal portion is in the curved relaxed configuration.

In some embodiments, one or more of the following may also apply: after cannulating the ostium with the distal portion of the microcatheter, advancing the guidewire into the ophthalmic artery; before proximally withdrawing the guidewire, inflating a balloon within one of a cervical segment, a petrous segment, or a lacerum segment of an internal carotid artery; in the curved relaxed configuration, the distal portion of the microcatheter corresponds to a shape of a shepherd's hook; t performing an angioplasty procedure via a balloon; and/or the accessed artery is an internal carotid artery, and during the angioplasty procedure, the balloon is located in one of the ophthalmic artery, the ostium, or extending partially within the internal carotid artery and into a short limb of the ophthalmic artery.

In still another embodiment, a method may comprise accessing an internal carotid artery in communication with an ophthalmic artery of a subject; advancing a microcatheter along the internal carotid artery so as to align a distal end of the microcatheter with an ostium between the internal carotid artery and the ophthalmic artery, wherein the microcatheter includes a lumen having a guidewire positioned therein; proximally withdrawing the guidewire relative to the microcatheter so as to enable a distal portion of the microcatheter to assume a curved relaxed configuration, wherein, in the curved relaxed configuration, a central longitudinal axis of the distal portion includes at least a first curve in a first direction and a second curve in a second direction different than the first direction; and cannulating the ostium via the distal portion of the microcatheter when the distal portion is in the curved relaxed configuration.

In some embodiments, one or more of the following may also apply: delivering the microcatheter to the internal carotid artery via a delivery artery, wherein the delivery artery is one of a supra-orbital artery, a supra-trochlear artery, a superficial temporal artery, or an occipital artery; before proximally withdrawing the guidewire, inflating a balloon within one of a cervical segment, a petrous segment, or a lacerum segment of the internal carotid artery; in the curved relaxed configuration, the distal portion of the microcatheter corresponds to a shape of a shepherd's hook; the seating the first curve in one of an ophthalmic segment or a communicating segment of the internal carotid artery, and seating the second curve in one of a clinoid segment or an ophthalmic segment of the internal carotid artery to stabilize the microcatheter; a radius of curvature of the first curve is larger than a radius of curvature of the second curve; in the curved relaxed configuration, the central longitudinal axis of the distal portion of the microcatheter further includes a third curve in a third direction; a radius of curvature of the first curve is larger than a radius of curvature of the second curve, and the radius of curvature of the second curve is larger than a radius of curvature of the third curve; performing an angioplasty procedure via a balloon; and/or, during the angioplasty procedure, the balloon is located in one of the ophthalmic artery, the ostium between the ophthalmic artery and the internal carotid artery, or extending partially within the internal carotid artery and into a short limb of the ophthalmic artery.

Further, in one embodiment, a method may comprise accessing an internal carotid artery in communication with an ophthalmic artery of a subject; advancing a support catheter along the internal carotid artery; stopping antegrade flow within the internal carotid artery by inflating a balloon of the support catheter within one of a cervical segment, a petrous segment, or a lacerum segment of the internal carotid artery; advancing a microcatheter along the internal carotid artery via the support catheter so as to align a distal end of the microcatheter with an ostium between the internal carotid artery and the ophthalmic artery, wherein the microcatheter includes a lumen having a guidewire positioned therein; proximally withdrawing the guidewire relative to the microcatheter so as to enable a distal portion of the microcatheter to assume a curved relaxed configuration, wherein, in the curved relaxed configuration, a central longitudinal axis of the distal portion includes at least a first curve in a first direction and a second curve in a second direction different than the first direction; and cannulating the ostium via the distal portion of the microcatheter when the distal portion is in the curved relaxed configuration.

In some embodiments, one or more of the following may also apply: in the curved relaxed configuration, the distal portion of the microcatheter corresponds to a shape of a shepherd's hook; seating the first curve in one of an ophthalmic segment or a communicating segment of the internal carotid artery, and seating the second curve in one of a clinoid segment or an ophthalmic segment of the internal carotid artery to stabilize the microcatheter; and/or performing an angioplasty procedure in one of the ophthalmic artery, the ostium between the internal carotid artery and the ophthalmic artery, or partially within the internal carotid artery and a short limb of the ophthalmic artery.

In yet another embodiment, a method may comprise accessing an artery in communication with an ophthalmic artery of a subject; advancing a balloon microcatheter along the accessed artery so as to align a distal end of the balloon microcatheter with an ostium of the ophthalmic artery, wherein the balloon microcatheter includes a lumen having a guidewire positioned therein; proximally withdrawing the guidewire relative to the balloon microcatheter so as to enable a distal portion of the balloon microcatheter to assume a curved relaxed configuration; cannulating the ostium with the distal portion of the balloon microcatheter when the distal portion is in the curved relaxed configuration; and performing a balloon dilation procedure by inflating a balloon of the balloon microcatheter within the ostium.

In some embodiments, one or more of the following also applies: the accessed artery is an internal carotid artery, and, during the balloon dilation procedure, a distal portion of the balloon is positioned within the ostium or the ophthalmic artery, while a proximal portion of the balloon is positioned within the internal carotid artery; during the balloon dilation procedure, no portion of the balloon extends beyond a short limb of the ophthalmic artery; the balloon microcatheter includes a first wall defining a first lumen and a second wall defining a second lumen; the proximally withdrawing the guidewire includes proximally withdrawing the guidewire through the first lumen; an annular space between the first wall and the second wall defines an inflation lumen for the balloon; in the curved relaxed configuration, a central longitudinal axis of the distal portion of the balloon microcatheter includes at least a first curve in a first direction and a second curve in a second direction different than the first direction; a radius of curvature of the first curve is larger than a radius of curvature of the second curve; in the curved relaxed configuration, the central longitudinal axis of the distal portion further includes a third curve; a radius of curvature of the first curve is larger than a radius of curvature of the second curve, and a radius of curvature of the second curve is larger than a radius of curvature of the third curve; a shape of the distal portion of the balloon microcatheter in the curved relaxed configuration corresponds to a shepherd's hook; and/or the accessed artery is an internal carotid artery, and, when the distal portion of the balloon microcatheter assumes the curved relaxed configuration, the method further comprises seating the first curve in one of an ophthalmic segment or a communicating segment of the internal carotid artery, and seating the second curve in one of a clinoid segment or the ophthalmic segment of the internal carotid artery to stabilize the balloon microcatheter.

In another embodiment, a method may comprise accessing an internal carotid artery in communication with an ophthalmic artery of a subject; advancing a balloon microcatheter along the internal carotid artery so as to align a distal end of the balloon microcatheter with an ostium of the ophthalmic artery, wherein the balloon microcatheter includes a lumen having a guidewire positioned therein; proximally withdrawing the guidewire relative to the balloon microcatheter so as to enable a distal portion of the balloon microcatheter to assume a curved relaxed configuration, wherein, in the curved relaxed configuration, a central longitudinal axis of the distal portion includes at least a first curve in a first direction and a second curve in a second direction different than the first direction; cannulating the ostium with the distal portion of the balloon microcatheter when the distal portion is in the curved relaxed configuration; and performing an angioplasty procedure by inflating a balloon of the balloon microcatheter within the ostium, wherein, during the performing the angioplasty, no portion of the balloon extends beyond a short limb of the ophthalmic artery.

In some embodiments, one or more of the following may also apply: during the balloon dilation procedure, a distal portion of the balloon is positioned within the ostium or the ophthalmic artery, while a proximal portion of the balloon is positioned within the internal carotid artery; the lumen having the guidewire positioned therein is a first lumen, and wherein the balloon microcatheter includes a first wall defining the first lumen and a second wall defining a second lumen; the inflating the balloon includes delivering inflation fluid to the balloon via the second lumen, wherein the second lumen is arranged between the first wall and the second wall; a radius of curvature of the first curve is greater than a radius of curvature of the second curve; a shape of the distal portion of the balloon microcatheter in the curved relaxed configuration corresponds to a shepherd's hook; and/or, when the distal portion of the balloon microcatheter assumes the curved relaxed configuration, the method further comprises seating the first curve in one of an ophthalmic segment or a communicating segment of the internal carotid artery, and seating the second curve in one of a clinoid segment or the ophthalmic segment of the internal carotid artery to stabilize the balloon microcatheter.

In yet another aspect, a method may comprise accessing an internal carotid artery in communication with an ophthalmic artery of a subject; advancing a balloon microcatheter along the internal carotid artery so as to align a distal end of the balloon microcatheter with an ostium between the internal carotid artery and the ophthalmic artery, wherein the balloon microcatheter includes a lumen having a guidewire positioned therein; proximally withdrawing the guidewire relative to the balloon microcatheter so as to enable a distal portion of the balloon microcatheter to assume a curved relaxed configuration, wherein, in the curved relaxed configuration, a central longitudinal axis of the distal portion includes at least a first curve in a first direction and a second curve in a second direction different than the first direction; seating the first curve in one of an ophthalmic segment or a communicating segment of the internal carotid artery, and seating the second curve in one of a clinoid segment or an ophthalmic segment of the internal carotid artery to stabilize the balloon microcatheter; cannulating the ostium via the distal portion of the balloon microcatheter when the distal portion is in the curved relaxed configuration; and performing an angioplasty procedure by inflating a balloon of the balloon microcatheter within the ostium, wherein, during the performing the angioplasty, a distal portion of the balloon is positioned within the ostium or the ophthalmic artery, a proximal portion of the balloon is positioned within the internal carotid artery, and no portion of the balloon extends beyond a short limb of the ophthalmic artery.

In still another embodiment, a microcatheter device may include a proximal portion; and a curved distal portion, the curved distal portion having: a first curve segment having a first curve radius in a first direction; a second curve segment distal of the first curve segment and having a second curve radius extending in a second direction that is different from the first direction; and a third curve segment distal of the second curve segment and having a third curve radius, wherein the first curve radius is from about 7.5 mm to about 15 mm, the second curve radius is from about 2 mm to about 3 mm, and the third curve radius is about 1 mm.

In other embodiments, one or more of the following may also apply: the first curve, the second curve, and the third curve are co-planar; the first direction is opposite to the second direction; the third curve includes a distal tip, and, when the microcatheter device is inserted into an internal carotid artery of a subject, the second curve is configured to point the distal tip toward an ostium between the internal carotid artery and an ophthalmic artery of the subject; when the microcatheter device is inserted into the internal carotid artery of the subject, the second curve is configured to position the distal tip in the ostium; the first curve has a tighter bend than a bend of a clinoid segment of an internal carotid artery of a subject; and/or the first curve has an arc angle of 35° to 55°.

In another embodiment, a microcatheter, which is to be introduced into an internal carotid artery to reach an ostium of an ophthalmic artery, the internal carotid artery including a clinoid segment proximal to the ostium, and having an inside bend and an outside bend, may include a proximal straight portion; a curved distal portion having a first curve extending from the straight portion and curving in a first direction, and a second curve extending from the first curve and curving in a second direction that is different from the first direction; and a distal tip, wherein, when the microcatheter is inserted into the internal carotid artery, the curved distal portion of the microcatheter is positioned in the internal carotid artery, the first curve engages the outside bend of the clinoid segment, and the second curve extends from the inside bend toward the ostium.

In some embodiments, one or more of the following may also apply: the first curve and the second curve are co-planar; the first direction is opposite to the second direction; the second curve is configured to point the distal tip toward the ostium; the second curve is configured to position the distal tip in the ostium; the first curve has a tighter bend than a bend of the clinoid segment; the first curve has a radius of curvature of 7.5 mm to 15 mm and an arc angle of 35° to 55°; the second curve has a radius of curvature of 2 mm to 3 mm and an arc angle of 170° to 190°; and/or the curved distal portion further includes a third curve extending from the second curve and having a radius of curvature of 1 mm and an arc angle of 15° to 30°.

In yet another embodiment, a microcatheter device may include a proximal portion; and a curved distal portion, the curved distal portion having: a first curve segment having a first curve radius in a first direction; a second curve segment distal of the first curve segment and having a second curve radius extending in a second direction that is opposite from the first direction; and a third curve segment distal of the second curve segment and having a third curve radius, the third curve segment defining a distal tip, wherein each of the first curve segment, second curve segment, and third curve segment are coplanar, and wherein the curved distal portion has a shape corresponding to a shepherd's hook.

In some embodiments, one or more of the following may also apply: the first curve segment has a radius of curvature of 7.5 mm to 15 mm and an arc angle of 35° to 55°; the second curve segment has a radius of curvature of 2 mm to 3 mm and an arc angle of 170° to 190°; and/or the third curve segment has a radius of curvature of 1 mm and an arc angle of 15° to 30°.

In another embodiment, a method may comprise percutaneously accessing a superficial temporal artery of a subject; advancing a device in a retrograde direction within the superficial temporal artery of the subject; advancing the device in the retrograde direction within an external carotid artery of the subject; advancing the device within a carotid bifurcation of a common carotid artery of the subject; and advancing the device in an antegrade direction within an internal carotid artery of the subject toward an ostium between an ophthalmic artery and the internal carotid artery.

In other embodiments, one or more of the following may also apply: percutaneously accessing the superficial temporal artery includes accessing the superficial temporal artery through a skin of a subject proximate to an ear of the subject; advancing the device into the ophthalmic artery; the device includes a guidewire and a microcatheter, and the method further comprises proximally withdrawing the guidewire relative to the microcatheter so as to enable a distal portion of the microcatheter to assume a curved relaxed configuration; when the distal portion of the microcatheter assumes the curved relaxed configuration, a central longitudinal axis of the distal portion includes at least first curve in a first direction, and a second curve in a second direction different than the first direction; when the distal portion of the microcatheter assumes the curved relaxed configuration, the first curve is seated in one of an ophthalmic segment or a communicating segment of the internal carotid artery, and the second curve is seated in one of a clinoid segment or the ophthalmic segment of the internal carotid artery to stabilize the microcatheter; a radius of curvature of the first curve is larger than a radius of curvature of the second curve; in the curved relaxed configuration, the central longitudinal axis of the distal portion further includes a third curve in a third direction; a radius of curvature of the first curve is larger than a radius of curvature of the second curve, and the radius of curvature of the second curve is larger than a radius of curvature of the third curve; cannulating the ostium via the distal portion of the microcatheter when the distal portion is in the curved relaxed configuration; the method further comprises performing a balloon dilation procedure in the ostium or the ophthalmic artery via a balloon on a distal end of the device; the advancing the device in the antegrade direction within the internal carotid artery includes advancing the device to one of a cervical segment, a petrous segment, a lacerum segment, or a cavernous segment of the internal carotid artery; fluidly connecting the device to a reversing system, wherein the reversing system includes a proximal manifold, a common conduit connected to the proximal manifold, and a reversing manifold connected to the common conduit; the reversing manifold comprises a U-turn conduit; and/or the advancing the device includes advancing the device via one or more micro motors of the reversing manifold.

In yet another aspect, a method may comprise percutaneously accessing an occipital artery of a subject; advancing a device in a retrograde direction within the occipital artery of the subject; advancing the device in the retrograde direction within an external carotid artery of the subject; advancing the device within a carotid bifurcation of a common carotid artery of the subject; and advancing the device in an antegrade direction within an internal carotid artery of the subject toward an ostium between an ophthalmic artery and the internal carotid artery of the subject.

In addition, one or more of the following may also apply: advancing the device into the ophthalmic artery; the device includes a guidewire and a microcatheter, and the method further comprises proximally withdrawing the guidewire relative to the microcatheter so as to enable a distal portion of the microcatheter to assume a curved relaxed configuration; a shape of the distal portion of the microcatheter in the curved relaxed configuration corresponds to a shepherd's hook; when the distal portion of the microcatheter assumes the curved relaxed configuration, a central longitudinal axis of the distal portion includes at least first curve in a first direction, and a second curve in a second direction different than the first direction; when the distal portion of the microcatheter assumes the curved relaxed configuration, the first curve is seated in one of an ophthalmic segment or a communicating segment of the internal carotid artery, and the second curve is seated in one of a clinoid segment or the ophthalmic segment of the internal carotid artery to stabilize the microcatheter; cannulating the ostium via the distal portion of the microcatheter when the distal portion is in the curved relaxed configuration; the advancing the device in the antegrade direction within the internal carotid artery includes advancing the device to one of a cervical segment, a petrous segment, a lacerum segment, or a cavernous segment of the internal carotid artery; and/or percutaneously accessing the occipital artery includes accessing the occipital artery through a skin of the subject proximate to an occipital bone of the subject.

In still another aspect, a method may comprise percutaneously accessing a superficial temporal artery of a subject; advancing a device in a retrograde direction within the superficial temporal artery of the subject, the device including a guidewire, a microcatheter, and a balloon at a distal end of the microcatheter; advancing the device in the retrograde direction within an external carotid artery of the subject; advancing the device within a carotid bifurcation of a common carotid artery of the subject; advancing the device in an antegrade direction within an internal carotid artery of the subject toward an ostium between an ophthalmic artery and the internal carotid artery; proximally withdrawing the guidewire relative to the microcatheter so as to enable a distal portion of the microcatheter to assume a curved relaxed configuration; and performing a balloon dilation procedure by dilating the balloon of the microcatheter in the ostium or the ophthalmic artery.

In another embodiment, the method further comprises seating a first curve of the distal portion in one of an ophthalmic segment or a communicating segment of the internal carotid artery, and seating a second curve the distal portion in one of a clinoid segment or the ophthalmic segment of the internal carotid artery to stabilize the microcatheter.

In another embodiment, a method may comprise acquiring an optical coherence tomography (OCT) en face image of a target anatomy of a subject; acquiring one or more OCT cross-sectional images of the target anatomy; identifying one or more dark areas in the acquired OCT en face image; selecting one or more OCT cross-sectional images corresponding to the identified one or more OCT en face image dark areas; identifying one or more dark areas in each of the selected OCT cross-sectional images; identifying one or more layers in each of the selected one or more OCT cross-sectional images in which photoreceptors reside; determining whether the identified one or more OCT cross-sectional image dark areas reside within the identified one or more layers; and, when the determining step determines a majority of the identified one or more OCT cross-sectional image dark areas reside within the one or more identified layers, indicating a treatment for arterial disease.

In some embodiments, one or more of the following may also apply: the target anatomy is a fovea of the subject; in the step of acquiring the OCT en face image of at least the fovea, an OCT en face image of the fovea, macula, and at least a majority of a retina of the subject is acquired; the OCT cross-sectional images include cross-sectional images of eye tissue and layers from a retina to a choroid of the subject; the treatment for arterial disease includes treating at least one of a blockage, a stenosis, a lesion, plaque, or other physiology of the subject; and/or the treatment includes balloon dilation.

In yet another embodiment, a method may comprise acquiring an optical coherence tomography (OCT) en face image of a fovea of a subject; acquiring one or more OCT cross-sectional images of the fovea, the OCT cross-sectional images including cross-sectional images of eye tissue and layers from a retina to a choroid of the subject; identifying one or more dark areas in the acquired OCT en face image; selecting one or more OCT cross-sectional images corresponding to the identified one or more OCT en face image dark areas; identifying one or more dark areas in each of the selected OCT cross-sectional images; identifying one or more layers in each of the selected one or more OCT cross-sectional images in which photoreceptors reside; determining whether the identified one or more OCT cross-sectional image dark areas reside within the identified one or more layers; and, when the determining step determines a majority of the identified one or more OCT cross-sectional image dark areas reside within the one or more identified layers, indicating a treatment for arterial disease.

In some embodiments, one or more of the following may also apply: in the step of acquiring the OCT en face image of at least the fovea, an OCT en face image of the fovea, macula, and at least a majority of the retina of the subject is acquired; the treatment for arterial disease includes treating at least one of a blockage, a stenosis, a lesion, plaque, or other physiology of the subject; the treatment includes balloon dilation; the balloon dilation includes balloon dilation of an ophthalmic artery of the subject; and/or the arterial disease includes one or more of age-related macular degeneration (AMD), glaucoma, or diabetic retinopathy.

In still another embodiment, a method may comprise acquiring an optical coherence tomography (OCT) en face image of a fovea of a subject; acquiring one or more OCT cross-sectional images of the fovea; identifying one or more dark areas in the acquired OCT en face image; selecting one or more OCT cross-sectional images corresponding to the identified one or more OCT en face image dark areas; identifying one or more dark areas in each of the selected OCT cross-sectional images; identifying one or more layers in each of the selected one or more OCT cross-sectional images in which photoreceptors reside; determining whether the identified one or more OCT cross-sectional image dark areas reside within the identified one or more layers; and, when the determining step determines a majority of the identified one or more OCT cross-sectional image dark areas reside within the one or more identified layers, indicating a treatment for arterial disease, the treatment for arterial disease including treating at least one of a blockage, a stenosis, a lesion, plaque, or other physiology of the subject, and, when the determining step determines the majority of the identified one or more OCT cross-sectional image dark areas do not reside within the one or more identified layers, not indicating a treatment for arterial disease.

In some embodiments, one or more of the following may also apply: in the step of acquiring the OCT en face image of at least the fovea, an OCT en face image of the fovea, macula, and at least a majority of a retina of the subject is acquired; the OCT cross-sectional images include cross-sectional images of eye tissue and layers from a retina to a choroid of the subject; the treatment includes balloon dilation; the balloon dilation includes balloon dilation of an ophthalmic artery of the subject; the arterial disease includes one or more of age-related macular degeneration (AMD), glaucoma, or diabetic retinopathy; the OCT cross-sectional image is acquired by swept source OCT; and/or the OCT cross-sectional image is acquired by spectral domain OCT.

In another embodiment, a microcatheter may comprise a shaft having variable flexibility along a length thereof, the shaft including: a multilayered proximal section including a proximal section outer layer; a multilayered mid-section including a mid-section outer layer that is more flexible than the proximal section outer layer; a multilayered distal section including a distal section outer layer that is more flexible than the mid-section outer layer, and a braid; and a distal tip including a variable pitch coil, the variable pitch coil having a distal closed-gap pitch, a proximal open-gap pitch, and a middle open-gap pitch greater than the proximal pitch, a distal end of the variable pitch coil terminating proximally of a distalmost end of the distal tip, wherein the braid of the distal section terminates at a distal end of the distal section and abuts a proximal end of the variable pitch coil.

In some embodiments, one or more of the following may also apply: an outer diameter of the distal tip is tapered toward the distal end of the distal tip; the multilayered distal section includes a dual-layer coil of helical hollow strands, wherein the helical hollow strands have an elliptical cross-sectional shape; the proximal section outer layer includes a polymer, and wherein the multilayered proximal section further includes a dual-layer coil comprising a helical hollow strand of wire, a single-layer braid, and an inner liner; the mid-section outer layer includes a polymer that is more flexible than the polymer of the proximal section outer layer, and wherein the multilayered mid-section further includes the dual-layer coil comprising the helical hollow strands of wire, the single-layer braid, and the inner liner; the distal section outer layer includes a polymer that is more flexible than the polymer of the mid-section outer layer, and wherein the multilayered distal section further includes the dual-layer coil comprising the helical hollow strands of wire, the single-layer braid, and the inner liner; the distal tip further includes a distal tip outer layer; and/or a wall thickness of the distal tip outer layer is greater than a wall thickness of the distal section outer layer.

In yet another embodiment, a may comprise a shaft having variable flexibility along a length thereof, the shaft including: a multilayered proximal section; a multilayered mid-section that is more flexible than the multilayered proximal section; a multilayered distal section that is more flexible than the multilayered mid-section, the multilayered distal section including: a distal section outer layer; a dual-layer coil having an inner coil layer and an outer layer coil; a single-layer braid; and an inner liner; and a distal tip including: a distal tip outer layer; a single-layer coil having a distal closed-gap pitch, a proximal open-gap pitch, and a middle open-gap pitch greater than the proximal pitch, wherein the single-layer coil terminates proximally of a distalmost end of the distal tip; and the inner liner, wherein a distal-most end of the single-layer braid abuts the proximal end of the single-layer coil at an abutment, wherein the outer layer coil of the dual-layer coil extends over the abutment between the single-layer braid and the proximal end of the single-layer coil, and the inner layer coil of the dual-layer coil terminates at the abutment between the single-layer braid and the proximal end of the single-layer coil, and wherein, in a first configuration, a central longitudinal axis of the distal tip extends along a straight line, while, in a second configuration, the central longitudinal axis of the distal tip is curved.

In some embodiments, one or more of the following may also apply: an outer diameter of the distal tip is tapered toward the distal end of the distal tip; the dual-layer coil is formed of helical hollow strands of wire, wherein the helical hollow strands of wire have an elliptical cross-sectional shape; the multilayered proximal section includes an outer layer formed of a polymer, the dual-layer coil comprising the helical hollow strands of wire, the single-layer braid, and the inner liner; the multilayered mid-section includes an outer layer that includes a polymer that is more flexible than the polymer of the outer layer of the proximal section, and wherein the multilayered mid-section further includes the dual-layer coil comprising the helical hollow strands of wire, the single-layer braid, and the inner liner; the distal section outer layer includes a polymer that is more flexible than the polymer of the mid-section outer layer; and/or the distal tip outer layer includes a polymer having a wall thickness that is greater than a wall thickness of the polymer of the distal section outer layer.

In still another embodiment, a microcatheter may comprise a shaft having variable flexibility along a length thereof, the shaft including: a proximal section including a solid core push wire and an outer layer; a plurality of distal sections including: a first multilayered distal section having a guidewire port at a proximal end; a second multilayered distal section extending from the first multilayered distal section, the second distal multilayered section being more flexible than the first multilayered distal section; a third multilayered distal section extending from the second multilayered distal section, the third multilayered distal section being more flexible than the second multilayered distal section; and a fourth multilayered distal section extending from the third multilayered distal section, the fourth multilayered distal section being more flexible than the third multilayered distal section; and a distal tip including a variable pitch coil having distal closed-gap pitch, a proximal open-gap pitch, and a middle open-gap pitch greater than the proximal pitch.

In some embodiments, one or more of the following may also apply: the outer layer of the proximal section is formed of a polyolefin heat shrink tubing; a diameter of the push wire of the proximal section tapers distally from 0.023" to 0.010"; the distal tip section includes a shape profile, wherein the shape profile includes any one of a straight line, a line with a 45° bend, a line with a 90° bend, a line with a 180° bend, a shepherd's hook, or an abbreviated shepherd's hook; and/or the distal tip section is formed into a shape of a shepherd's hook having a first curve in a first direction, and a second curve in a second direction that is different from the first direction, wherein the second curve extends from a distal end of the first curve.

In another embodiment, a balloon catheter may comprise a shaft extending between a proximal end and a distal end, the shaft including: an inner shaft portion extending from the proximal end, through a balloon, to a distal tip, the inner shaft portion having: an inner liner; a metallic support middle layer; and an outer layer; and an outer shaft extending from the proximal end to the balloon.

In some embodiments, one or more of the following may also apply: the outer shaft portion has a first flexibility at the proximal end and a second flexibility at the distal end, wherein the second flexibility is greater than the first flexibility; the inner liner comprises a polymer, the metallic support middle layer is a coil, and the outer layer comprises a thermoplastic elastomer; the inner liner includes etched polytetrafluoroethylene (PTFE), the coil includes spring temper 304v stainless steel, and the thermoplastic elastomer includes PEBAX® 3533; a portion of the inner shaft portion extends distally beyond a distal waist of the balloon to form the distal tip; the balloon catheter may further comprise at least one marker band provided radially between the inner shaft portion and the balloon at one or more positions; the at least one marker band is a radiopaque marker band; and/or the at least one marker band abuts a distal terminus of the coil of the middle layer.

In yet another embodiment, a balloon catheter may comprise a balloon; and a shaft, including: an outer shaft portion, wherein a proximal neck of the balloon is coupled to a distal end of the outer portion; and a multilayered inner shaft portion extending through the balloon to a distal tip, wherein a distal neck of the balloon is coupled to the multilayered inner shaft portion, the multilayered inner shaft portion having: an inner liner; a metallic support middle layer; and an outer layer; wherein each of the outer shaft portion and the inner shaft portion extend between a proximal end of the shaft and a distal end of the shaft.

In some embodiments, one or more of the following may also apply: the inner liner comprises a polymer, the metallic support middle layer is a coil, and the outer layer comprises a thermoplastic elastomer; the inner liner includes etched polytetrafluoroethylene (PTFE), the coil includes spring temper 304v stainless steel, and the thermoplastic elastomer includes PEBAX® 3533; a portion of the inner shaft portion extends distally beyond the distal neck of the balloon to form the distal tip; the balloon catheter may further comprise at least one marker band provided radially between the inner shaft portion and the balloon at one or more positions; the at least one marker band is a radiopaque marker band; and/or the at least one marker band abuts a distal terminus of the coil of the middle layer.

In still another embodiment, a balloon catheter may comprise a catheter shaft outer portion; a catheter shaft inner portion disposed radially within the outer portion and defining a guidewire lumen extending therethrough, an annular space between the outer portion and the inner portion defining an inflation lumen; a distal tip section, wherein, in a curved configuration, the distal tip section includes at least a first curve in a first direction and a second curve in a second direction different than the first direction; and a balloon in fluid communication with the inflation lumen, wherein a proximal neck of the balloon is coupled to the outer portion and a distal neck of the balloon is coupled to the inner portion.

In some embodiments, one or more of the following may also apply: the outer portion includes a series of increasing flexible polymer tubes from a proximal end of the outer portion to a distal end of the outer portion; the balloon catheter further comprises at least one radiopaque marker provided on the inner portion adjacent to at least one of a proximal end and a distal end of the balloon; the first curve has a radius of approximately 7.5 mm to 15 mm and an arc length of approximately 35° to 55°, wherein the second curve has a radius of approximately 2 mm to 3 mm and an arc length of approximately 170° to 190°; and/or, in the curved configuration, the distal tip section includes a third curve extending from a distal end of the second curve.

In another embodiment, a balloon catheter may comprise a shaft including: a tubular proximal shaft section; a tubular mid-shaft section extending distally of the proximal shaft section; a core wire extending from the proximal shaft section and into the mid-shaft section; and a multi-lumen tubular distal shaft section extending from the mid-shaft section, a junction between the distal shaft section and the mid-shaft section forming a guidewire port, the distal shaft section including a balloon positioned thereon, wherein the junction between the mid-shaft section and the distal shaft section is configured to burst at a pressure that is lower than a burst pressure of the balloon.

In some embodiments, one or more of the following may also apply: the junction further includes a thermal bond; the thermal bond forms a seal; the balloon has a nominally rated inflation pressure and the junction is configured to burst between 1 ATM and 4 ATM above the nominally rated inflation pressure; the distal shaft section includes an inner portion and an outer portion; the outer portion includes a first polymer, and the inner portion includes an inner polymeric liner, a metallic middle layer, and an outer polymeric layer; the distal shaft section further includes a tack bond provided between the outer portion and the inner portion to thereby limit longitudinal movement between the outer portion and the inner portion; and/or the tack bond is configured to transmit longitudinal push forces between the outer portion and the inner portion.

In yet another embodiment, a balloon catheter may comprise a shaft including: a tubular proximal shaft section; a tubular mid-shaft section extending distally of the proximal shaft section; a core wire coupled to the proximal shaft section and extending from the proximal shaft section and into the mid-shaft section; and a multi-lumen tubular distal shaft section extending from the mid-shaft section, a junction between the distal shaft section and the mid-shaft section forming a guidewire port, the distal shaft section including: a distal outer portion extending from the guidewire port to a balloon, wherein a proximal neck of the balloon is coupled to a distal end of the distal outer portion; and a multilayered inner portion extending from the guidewire port, through the balloon, to a distal tip, wherein a distal neck of the balloon is coupled to the inner portion, and the multilayered inner portion having: an inner liner; a metallic support middle layer; and an outer layer.

In some embodiments, one or more of the following may also apply: the junction between the mid-shaft section and the distal shaft section is configured to burst at a pressure that is lower than a burst pressure of the balloon; the junction forms a fluid seal; the balloon has a nominally rated inflation pressure and the junction is configured to burst between 1 ATM and 4 ATM above the nominally rated inflation pressure; the distal outer portion includes a first polymer, the inner liner of the multilayered inner portion includes PTFE, the metallic support layer of the inner portion includes a stainless steel coil, and the outer layer of the inner portion includes a second polymer; the distal shaft section further includes a tack bond provided between the distal outer portion and the multilayered inner portion to thereby limit longitudinal movement between the distal outer portion and the multilayered inner portion; and/or the tack bond is configured to transmit longitudinal push forces between the outer portion and the inner portion.

In still another embodiment, a balloon catheter may comprise a shaft including: a proximal shaft section; a mid-shaft section extending distally of the proximal shaft section; and a distal shaft section extending from the mid-shaft section, a junction between the distal shaft section and the mid-shaft section forming a guidewire port, the junction including a seal, the distal shaft section including: a distal outer portion extending from the guidewire port to a balloon, wherein a proximal neck of the balloon is coupled to a distal end of the distal outer portion; and a multilayered inner portion extending from the guidewire port, through the balloon, to a distal tip, wherein a distal neck of the balloon is coupled to the inner portion, and the multilayered inner portion having: an inner liner; a metallic support middle layer; and an outer layer, wherein the junction between the mid-shaft section and the distal shaft section is configured to burst at a pressure that is lower than a burst pressure of the balloon, and wherein the balloon has a nominally rated inflation pressure and the junction is configured to burst between 1 ATM and 4 ATM above the nominally rated inflation pressure.

In some embodiments, one or more of the following may also apply: the distal outer portion includes a first polymer, the inner liner includes PTFE, the metallic support layer includes a stainless steel coil, and the outer layer includes a second polymer; the distal shaft section further includes a tack bond provided between the distal outer portion and the multilayered inner portion, the tack bond being thermally formed to thereby limit longitudinal movement between the distal outer portion and the multilayered inner portion; the tack bond is configured to transmit longitudinal push forces between the outer portion and the inner portion; and/or the proximal neck of the balloon is thermally bonded to the distal outer portion of the distal shaft section and the distal neck of the balloon is thermally bonded to the multilayered inner portion of the distal shaft section.

BRIEF DESCRIPTION OF THE DRAWINGS

FIGS. 15 and 15A-15F are schematic drawings of a balloon access and support catheter for use in the method described with reference to FIGS. 1-14;

FIGS. 16, 16A, and 16B are schematic drawings of a neuro access and support catheter for use in the method described with reference to FIGS. 1-14;

FIGS. 16D-16I are schematic drawings of an alternative rapid exchange neuro access and support catheter;

FIGS. 17 and 17A-17E are schematic drawings of an over-the-wire aiming microcatheter for use in the method described with reference to FIGS. 1-14;

FIGS. 18A-18F are schematic drawings of various curves for use on the aiming microcatheter;

FIGS. 19 and 19A are schematic drawings of a rapid exchange aiming microcatheter for use in the method described with reference to FIGS. 1-14;

FIGS. 20 and 20A-20C are schematic drawings of a rapid exchange micro balloon catheter for use in the method described with reference to FIGS. 1-14;

FIG. 21A is a schematic side sectional view of an alternative microcatheter;

FIG. 21B is a more detailed schematic side sectional view of the main proximal shaft of the microcatheter shown in FIG. 21A;

FIG. 21C is a more detailed schematic side sectional view of the distal tip of the microcatheter shown in FIG. 21A;

FIG. 21D is a more detailed schematic side sectional view of the transition between the main shaft and distal tip of the microcatheter shown in FIG. 21A;

FIGS. 23A-23H are schematic side views of various tip shapes for use with the microcatheter shown in FIG. 21A;

FIG. 24D is a more detailed schematic side sectional view of the balloon, inner and tip assembly of the balloon catheter shown in FIG. 24A;

FIG. 24E is a schematic side sectional view of an alternative inner of the balloon catheter shown in FIG. 24A;

FIG. 25A is a schematic side sectional view of a guidewire;

FIG. 25B is a more detailed schematic side sectional view of the distal portion of the guidewire shown in FIG. 25A;

FIG. 35A is a schematic side sectional view of a distal portion of an innerless over-the-wire balloon catheter for use in the oculofacial approach;

FIG. 35B is a schematic side sectional view of a proximal portion of the innerless over-the-wire balloon catheter shown in FIG. 35A;

FIG. 35C is a schematic side sectional view of a distal portion of a guidewire for use with the innerless over-the-wire balloon catheter shown in FIG. 35A;

FIG. 35D is a cross-sectional view taken along line B-B in FIG. 35C;

FIG. 35E is a more detailed view of the distal portion of the innerless over-the-wire balloon catheter shown in FIG. 35A;

FIG. 35F is a cross-sectional view taken along line A-A in FIG. 35E;

DETAILED DESCRIPTION

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. Relative terms, such as, "substantially" and "generally," are used to indicate a possible variation of ±10% of a stated or understood value.

The devices, systems and methods described herein are intended to provide improved access and treatment of vascular disease in arteries supplying blood to the eye. Such vascular targets may include the ICA near the OA, the ostium of the OA as it branches off the ICA, or any part of the OA including the short limb, angle A or the long limb as described by Hayreh, for example. The improved devices may include a guidewire (GW), a neuro access and support catheter (NASC), a balloon access and support catheter (BASC), an aiming microcatheter (AMC), a micro balloon catheter (MBC), a diagnostic catheter (DC), an aiming intermediate catheter, an aiming intermediate catheter sheath and a guide sheath, for example. These devices may be used alone or in various combinations.

EXAMPLE METHOD

Each of the devices described herein may be configured to work cooperatively to reach the OA from an access site in the femoral artery. The diameters and lengths may be adjusted to accommodate different access sites such as the radial, brachial, cervical or common carotid arteries. Less known or heretofore unknown access sites may also be used, such as access from the supra-orbital, supra-trochlear, superficial temporal or occipital arteries. These alternative access sites are described in more detail hereinafter. For purposes of illustration, not necessarily limitation, the following description refers to the femoral access approach.

Figure 1:
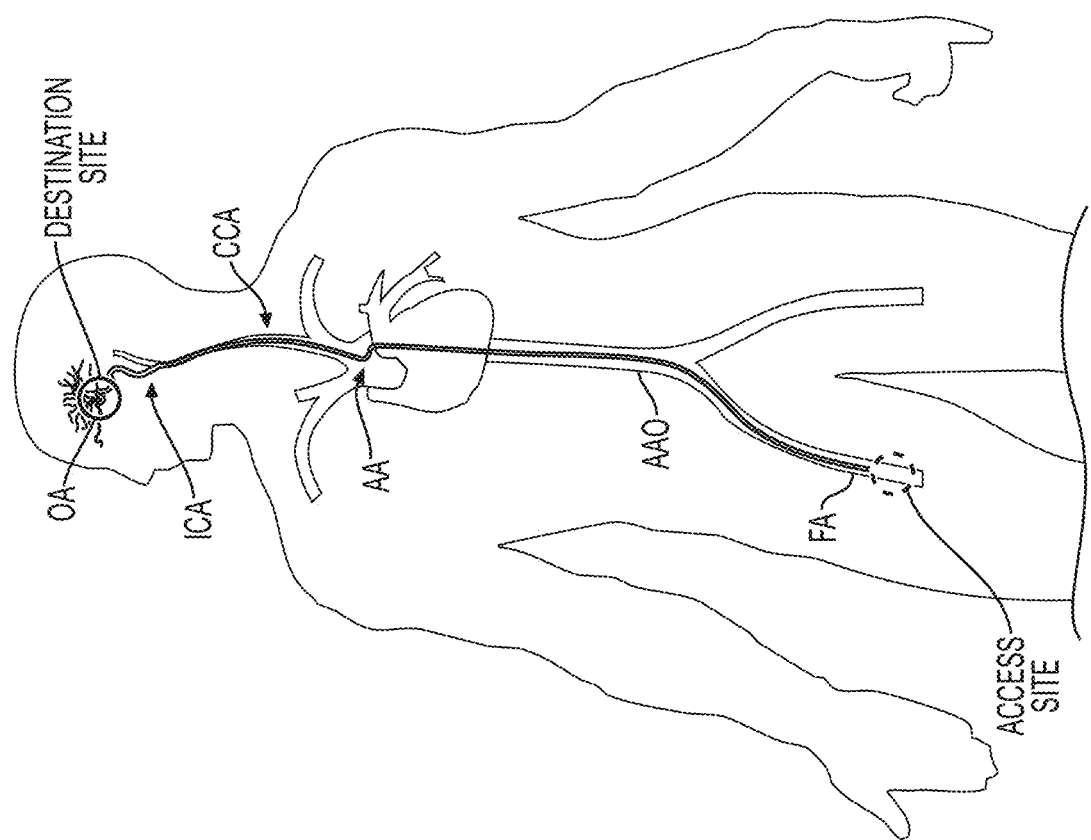

With reference to FIG. 1, a femoral approach may involve percutaneous access into the femoral artery (FA), advancement through the ascending aorta (AAo), selective cannulation of the right or left common carotid artery (CCA) depending on which eye (right or left) is to be treated, and advancement through the internal carotid artery (ICA) to the ophthalmic artery (OA).

Figure 2:
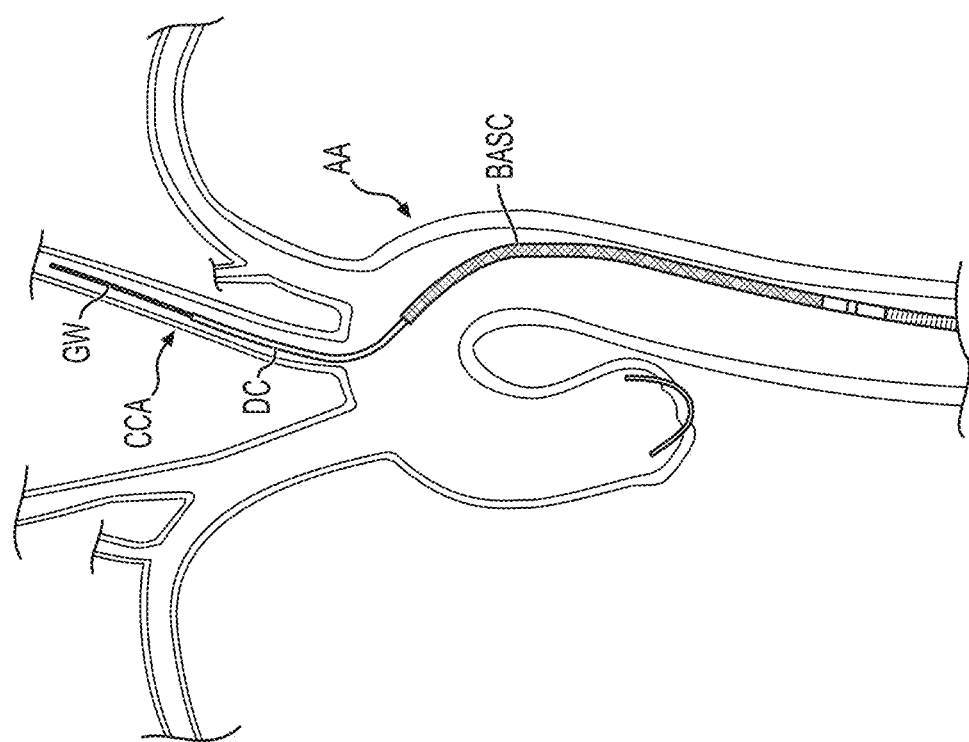
FIGS. 1-14 are schematic illustrations of a method of access and treatment of the OA.

With reference to FIG. 2, after percutaneous access into the FA, the BASC (alternatively the NASC) with the DC and 0.035" GW pre-loaded therein may be advanced up the FA, AAo and into the AA, using the desired shape (e.g., Simmons 1, Simmons 2, or Headhunter 1, depending on anatomical geometry) of the DC to selectively cannulate the CCA of choice (right or left).

Figure 3:
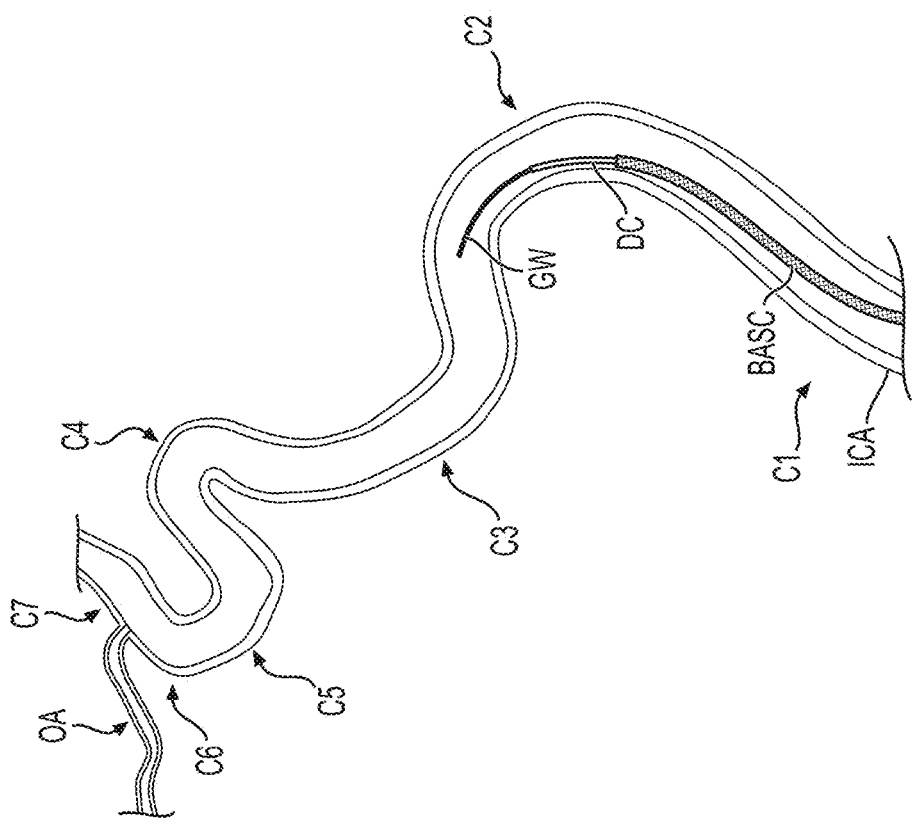

With reference to FIG. 3, the BASC, DC and GW may be advanced into the ICA. The ICA may be characterized by segments, where C1 is the cervical segment, C2 is the petrous segment, C3 is the lacerum segment, C4 is the cavernous segment, C5 is the clinoid segment, C6 is the ophthalmic segment and C7 is the communicating segment. In this example, the BASC, DC and GW are advanced together until they reach at least C1 and up to C4.

Figure 4:
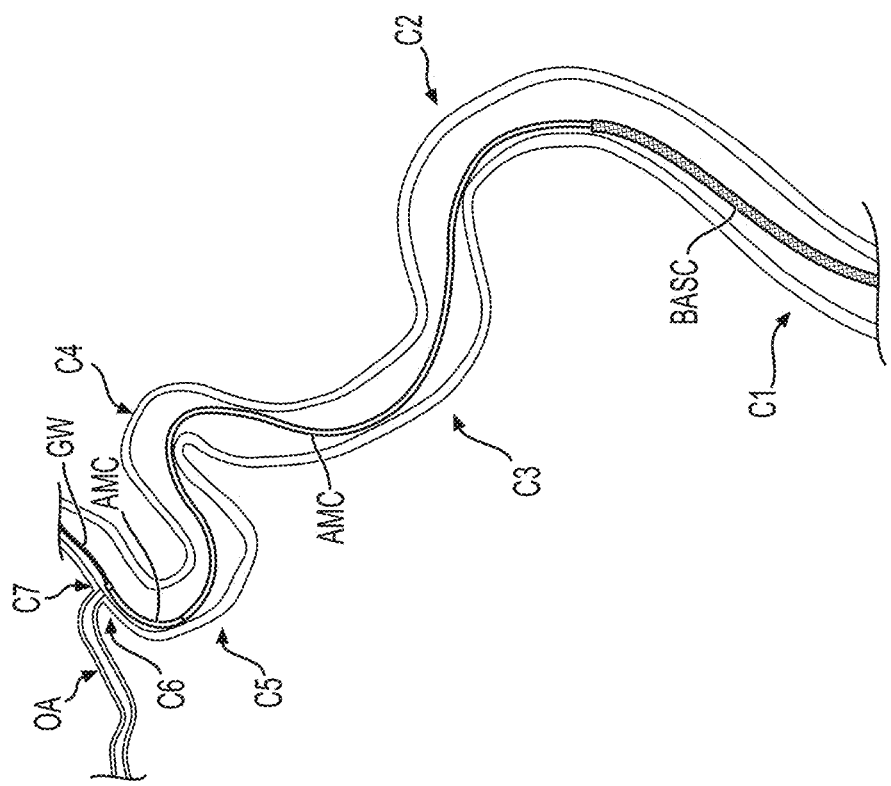

With reference to FIG. 4, the DC and 0.035" GW may be removed from the BASC. The AMC over an 0.014" GW may be advanced through the BASC until the GW is positioned beyond C6 and the distal portion of the AMC is positioned in C6.

Figure 5:
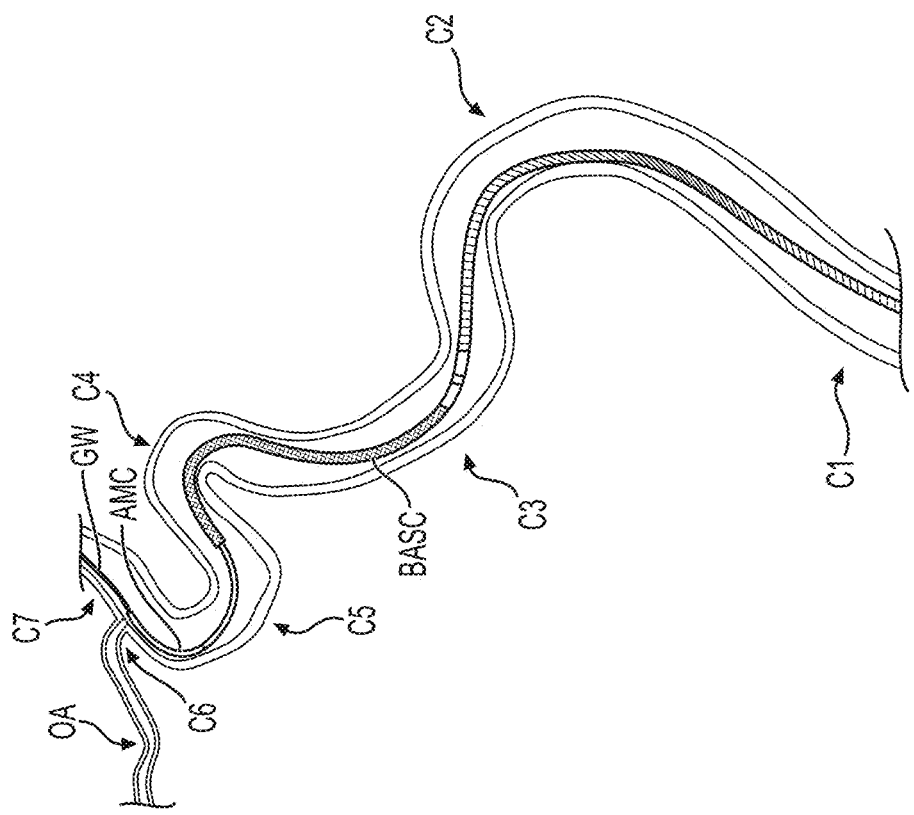

With reference to FIG. 5, the BASC may be advanced over the AMC until the distal end of the BASC is positioned in C4 or C5. The inside diameter of the BASC may be closely matched to the outside diameter of the AMC to mitigate dislodgement of emboli in the ICA by edge effects of the BASC.

Figure 6:
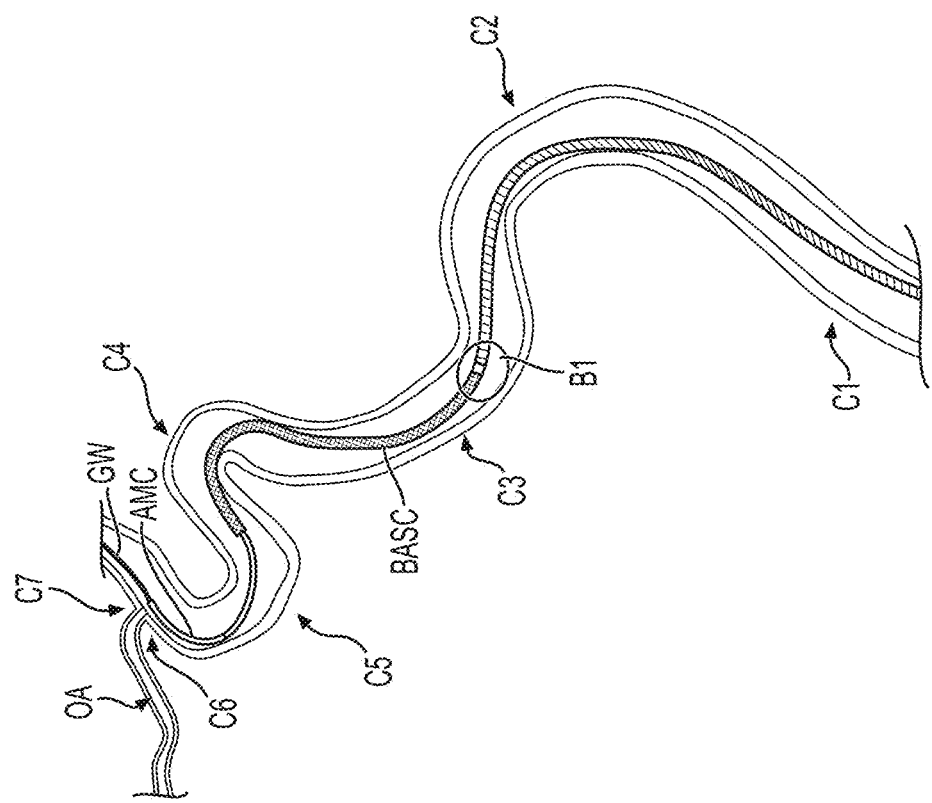

With reference to FIG. 6, note that the balloon B1 on the BASC may be positioned approximately 6-10 cm proximal of the distal end of the BASC. Thus, with the distal end of the BASC positioned in C4 or C5 to support the AMC and GW for cannulation of the OA, the balloon B1 may be inflated more proximally in the ICA such as in segments C1, C2 or C3. Segments C1-C3 tend to have less disease as compared to segments C4-C6, therefore inflating the balloon B1 in this region reduces the likelihood of embolic dislodgement while still providing distal support of the AMC in segments C4-C6. The balloon B1, while inflated, may serve to cause flow cessation in the ICA and intraprocedural aspiration through the BASC to further mitigate the likelihood of a distal embolic event.

Figure 7:
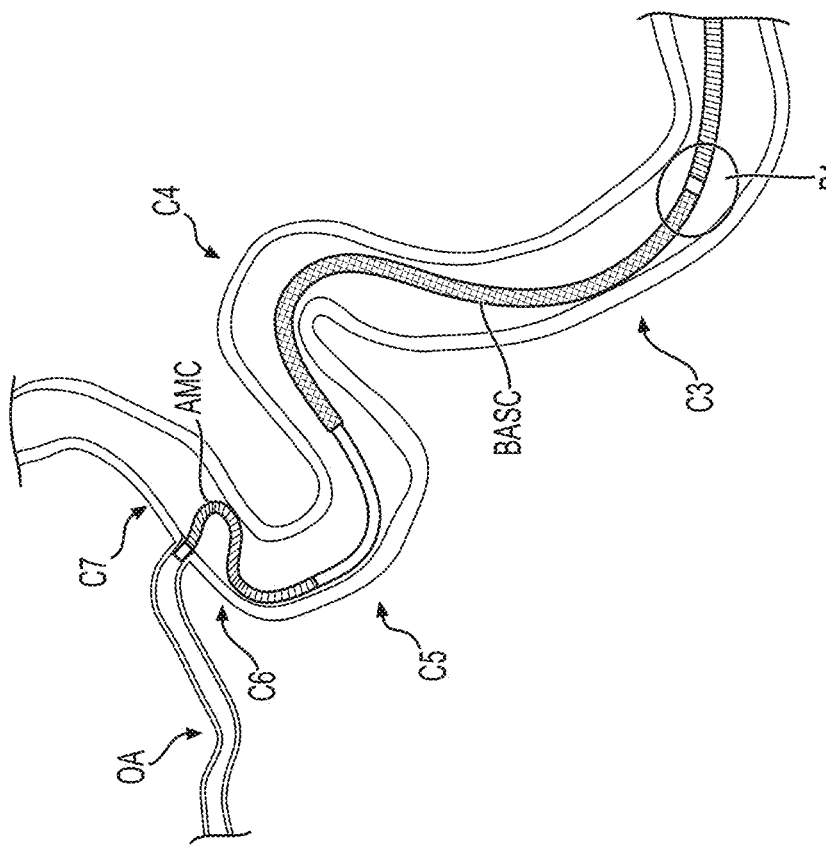

As seen in FIG. 7, while the balloon B1 is inflated in C1-C3, the distal end of the AMC is in C6-C7 and the distal end of the GW extends beyond the distal end of the AMC as shown in FIG. 7, the system is positioned for cannulation of the OA. As will be described in more detail hereinafter, the AMC may have a distal curvature that may be substantially straighter when the GW extends therethrough as seen in FIG. 7.

Figure 8:
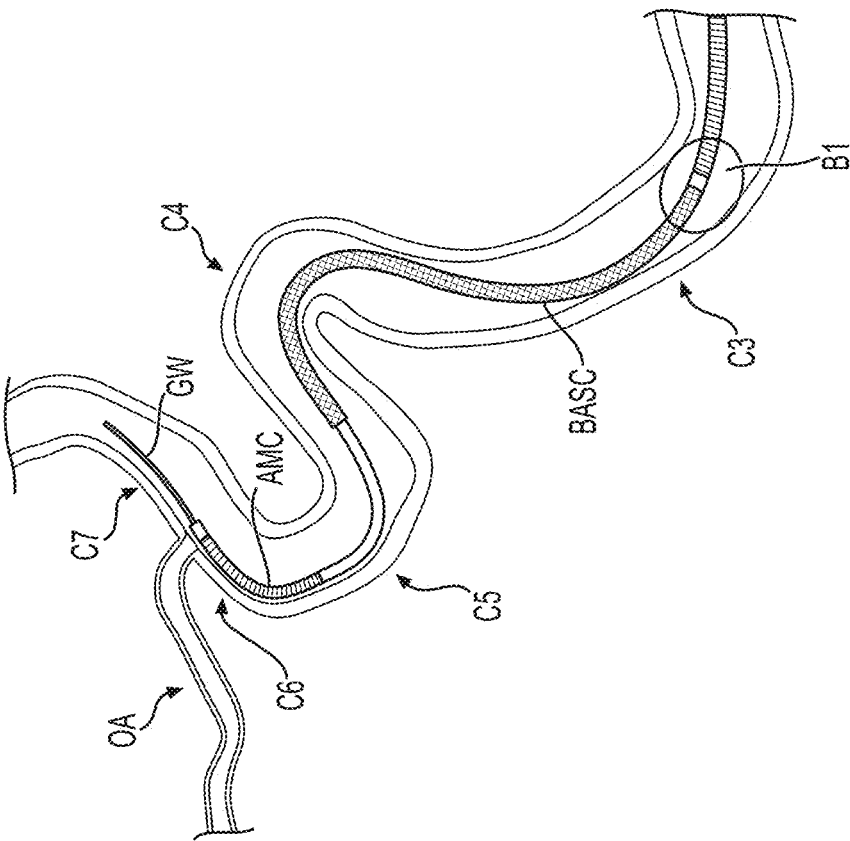

With reference to FIG. 8, the distal curvature of the AMC assumes its relaxed state (e.g., similar to a Sheppard's hook) when the GW is retracted in the AMC proximal of the curvature. The distal curvature of the AMC may be configured such that it follows the outside contour of C5-C6, the inside curvature of C6 and extends across the ICA lumen such that the distal end of the AMC naturally rests in the ostium of the OA as shown in FIG. 8. This may be referred to as a "microcatheter first technique", which is different than conventional cannulation techniques that use the GW to cannulate first and then the microcatheter is advanced over the GW. The superior torque response and curve retention of the AMC, together with its atraumatic tip, allow the AMC to be used to safely and reliably cannulate the OA while the GW is retracted proximally in the AMC (proximal of the curved tip of the AMC).

Figure 9:
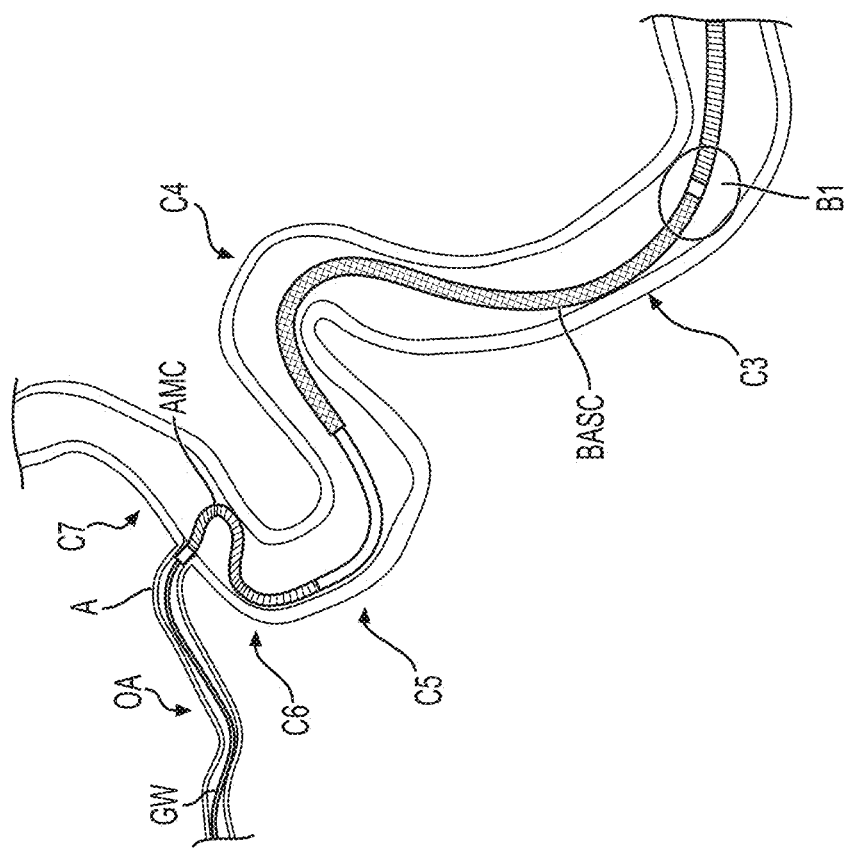

With reference to FIG. 9, after successful cannulation of the OA ostium with the AMC, the GW may be advanced in the AMC to extend into the OA, such as into the short limb, angle alpha ("A"), or into the long limb beyond angle A. Positioning the GW beyond angle A provides additional purchase of the GW to subsequently support the MBC as it cannulates the OA.

Figure 10:
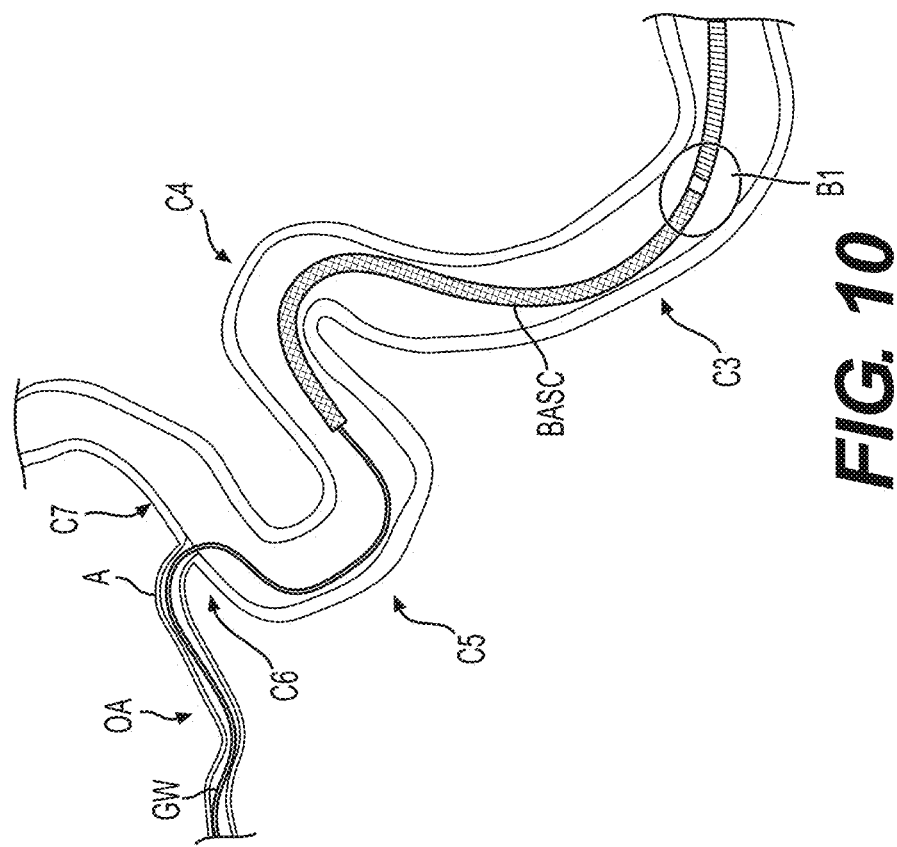

With reference to FIG. 10, once the GW is deep seated in the OA such as beyond angle A, the AMC may be removed leaving the GW and BASC in place.

Figure 11:
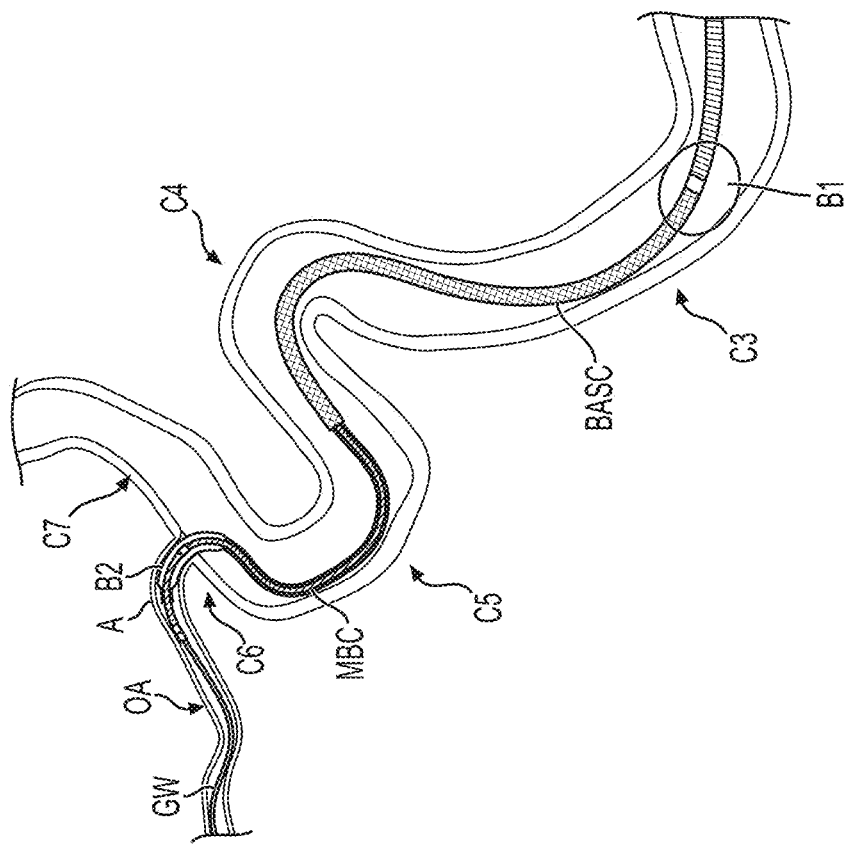
Figure 12:
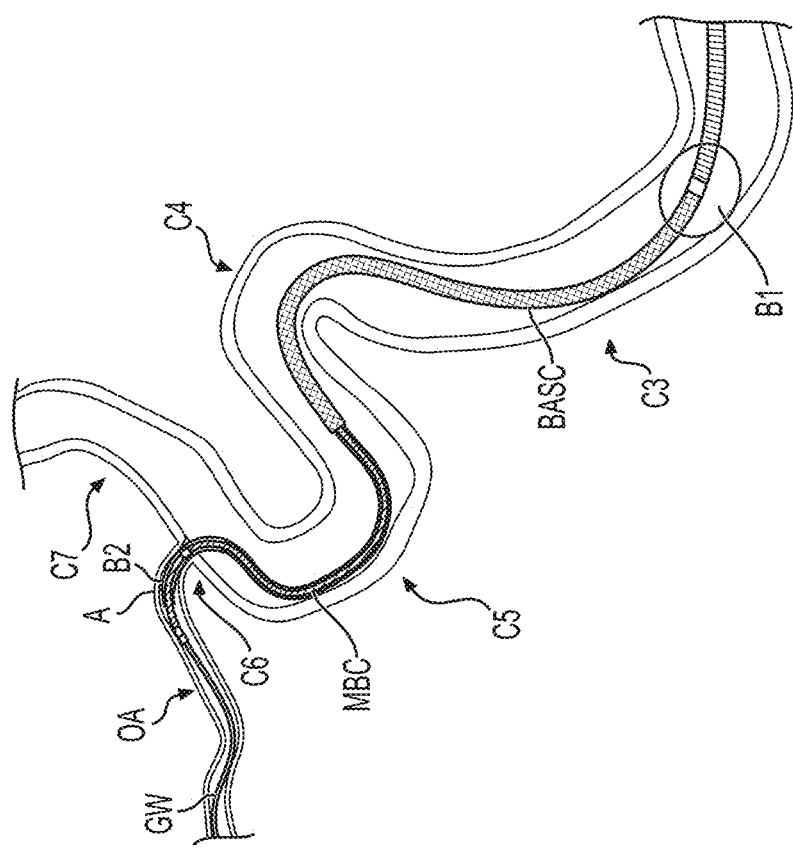

With reference to FIGS. 11 and 12, the MBC may be advanced over the GW inside the BASC until the balloon B2 of the MBC is positioned in the OA, OA ostium or bridges the OA ostium from inside the ICA into the OA short limb adjacent angle A. Cadaver studies performed by the inventors have demonstrated that the natural funnel shape of the OA ostium is absent in people with eye disorders such as AMD, thus the OA ostium may be a target for balloon dilation to restore the natural funnel shape. The balloon B2 may be positioned in the OA proximal of anterior clinoid process, specifically the opening of the optic canal in the anterior clinoid process to avoid dilating the OA against bony structure adjacent the optic nerve. The distance of the OA origin from the ICA to the opening of optical canal in anterior clinoid process is typically about 5 mm, which roughly corresponds to the OA just beyond angle A. As such, note that the balloon B2 is in the short limb proximal of angle A to avoid dilation of angle A and to avoid dilating the OA in the optical canal, and note that the balloon B2 is partially in the OA and partially in the ICA to effectively dilate the OA ostium. Once in the desired position such as the position shown in FIG. 11, the balloon B2 may be inflated to the desired pressure and duration as shown in FIG. 12 to restore a natural funnel shape to the OA ostium.

Figure 14:
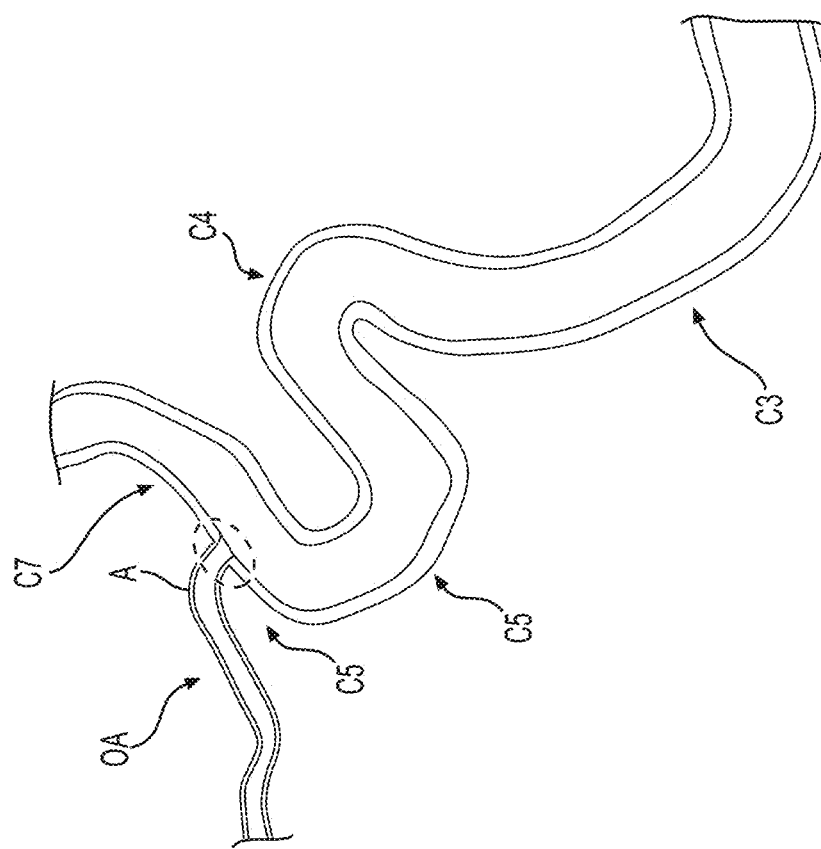
Figure 13:
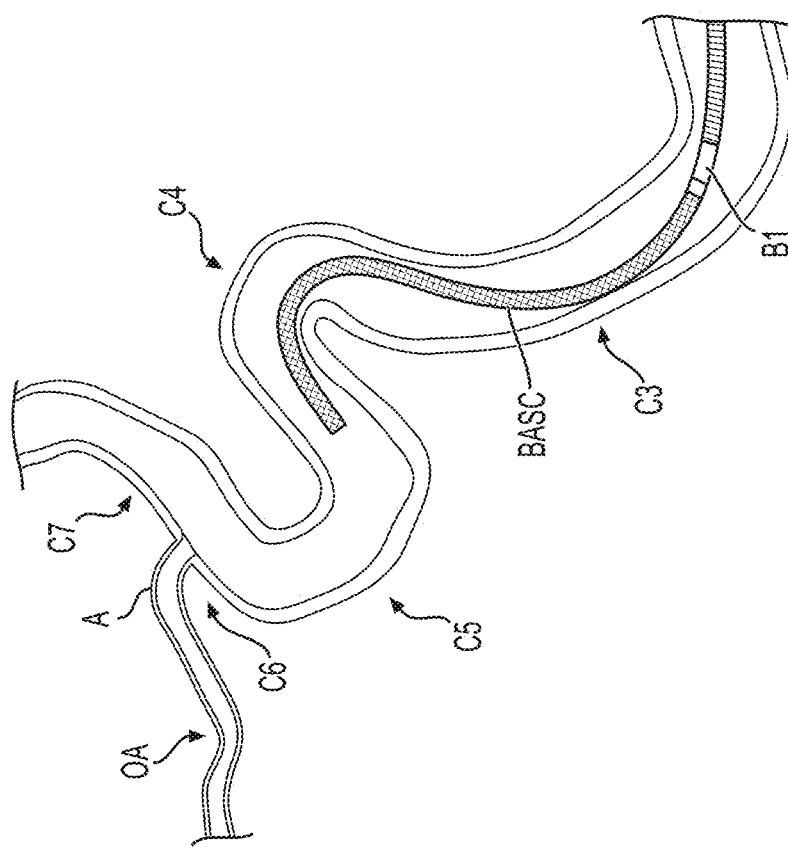

With reference to FIGS. 13 and 14, the balloon B2 may be deflated and the MBC may be removed as shown in FIG. 13. Aspiration through the BASC may be stopped and the balloon B1 may be deflated for subsequent removal as shown in FIG. 14. Thus, this system of devices may be used to restore a natural funnel shape at the OA ostium as shown by the dotted circle in FIG. 14, thereby improving blood flow to the back of the eye and treating the underlying eye disorder.

The following describes the construction of the devices used in the methods illustrated in FIGS. 1-14. These are given by way of example, not limitation, and alternative devices may be used for similar purposes, such as the alternative designs described herein.

Balloon Access and Support Catheter (BASC)

With reference to FIG. 15, the BASC 100 is shown schematically. BASC 100 may include a dual port manifold 102 comprising molded copolyester (e.g., Tritan MX 731) having a through port 104 for passage of fluids and devices through the BASC 100 and an inflation port 106 for inflation and deflation of an occlusion balloon 120. BASC 100 may also include a strain relief 108 comprising a molded thermoplastic elastomer (e.g., PEBAX 3533) to provide stiffness transition from the manifold 102 to the shaft 110. The occlusion balloon 120 may be disposed on a distal portion of the shaft 110, and a distal extension 114 may extend therefrom. Aspirations holes (not shown) may extend through the wall of the distal extension 114 about 1 mm-10 mm distal of the balloon to provide additional aspiration. A radiopaque marker band 112 may be disposed under a distal aspect of the balloon 120. The BASC 100, including the elongate shaft 110, occlusion balloon 120 and distal extension 114, may have an overall length of about 115 cm, a minimum inside diameter of about 0.058" and a maximum outside diameter of about 0.084". The distal extension 114 may have a length of about 8.0 cm such that the occlusion balloon 120 is positioned proximal of the distal extremity of the BASC 100.

With reference to FIG. 15A which is a detailed view of circle A shown in FIG. 15, and FIG. 15B which is a cross-sectional view taken along line B-B in FIG. 15A, the elongate shaft 110 may include and inner 130 defining a through lumen 116. The inner 130 may be disposed inside an outer 140 defining an annular inflation lumen 118 therebetween. The occlusion balloon 120 may comprise a thermoplastic polyurethane (e.g., Tecothane AR-62A) having a proximal end connected to a distal portion of the outer 140 and a distal end connected to a distal portion of the inner 130. The distal and proximal ends of the balloon 120 may be thermally bonded to the inner 130 and outer 140, respectively. The distal extension 114 may comprise a continuation of the inner 130, absent the outer 140, beyond the distal end of the balloon 120. The inflatable portion of the balloon 120 may have a length of about 8 mm and an inflated diameter of about 4-10 mm. The distal end of the outer 140 may terminate at a midpoint under the balloon 120, and a tack bond 150 may connect the distal end of the outer 140 to the inner 130 leaving a crescent-shaped inflation lumen 118 gap of about 0.005". The tack bond 150 may extend a minimum of $\frac{1}{3}^{rd}$ of the circumference of the interface between the inner 130 and outer 140.

With reference to FIG. 15C, the inner 130 is shown schematically in more detail. The inner 130 may comprise a multi-layered tube with gradually increasing zones of flexibility in the distal direction. For example, the inner 130 may include a proximal support section 132 having a length of about 100 cm and an outside diameter of about 0.067" comprising an inner PTFE liner (e.g., PTFE with PEBAX top coat; 0.058" inside diameter; 0.00075" PTFE wall thickness), a wire braid middle layer (e.g., 16 carriers of 0.0015" diameter 304v/300 KPSI stainless steel paired wire at 55 picks per inch) and a polyamide outer layer (e.g., Grilamid L20 or Vestamid Care 21 ML; with a wall thickness inclusive of braid of 0.003" to 0.005", preferably 0.004"). Extending from the proximal support section 132, the inner 130 may further include a proximal transition section 134 having a length of about 5.0 cm and an outside diameter of about 0.067" comprising the same layers as proximal support section 132 except the outer layer may comprise a thermoplastic elastomer (e.g., PEBAX 7233; with a wall thickness inclusive of braid of 0.003" to 0.005", preferably 0.004"). Extending from the proximal transition section 134, the inner 130 may further include a distal transition section 136 having a length of about 5.0 cm and an outside diameter of about 0.067" comprising the same layers as proximal transition section 134 except the outer layer may comprise a softer thermoplastic elastomer (e.g., PEBAX 5533; with a wall thickness inclusive of braid of 0.003" to 0.005", preferably 0.004"). Extending from the distal transition section 136, the inner 130 may further include a distal section 138 having a length of about 9.0 cm and an outside diameter of about 0.067" comprising the same inner liner layer, a mid-layer of pattern-cut super-elastic metal tube (e.g., laser cut NiTi tube, polished; 0.00175" to 0.0025" wall thickness) and an outer layer of thermoplastic polyurethane (e.g., Techothane AR-62A; with a wall thickness inclusive of NiTi tube of 0.003").

With reference to FIG. 15E which is a partial cross-sectional view taken along line E-E in FIG. 15C, the junction between the distal transition section 136 and the distal section 138 is shown in more detail. The inner PTFE liner 131 extends across this junction, with the braid 133 abutting the pattern-cut super-elastic metal tube 135, and the thermoplastic elastomer outer layer 137 abutting the thermoplastic polyurethane 139. A short bridging layer of PET (not shown) may extend across the braid 133 and the pattern-cut super-elastic metal tube 135 under the outer layers 137 and 139. The radiopaque marker band 112 (e.g., 90/10 PtIr; approximately 0.9 mm length) may be disposed over the braid 133 and the pattern-cut super-elastic metal tube 135 and encapsulated by the outer thermoplastic polyurethane layer 139.

With reference to FIG. 15D which is a partial cross-sectional view taken along line D-D in FIG. 15C, the distal tip of distal extension 138 is shown in more detail. The inner PTFE liner 131 extends through to the distal end along with the outer thermoplastic polyurethane layer 139. The pattern-cut super-elastic metal tube 135 terminates proximal of the distal end and is abutted by another radiopaque marker band 113 (e.g., 90/10 PtIr; approximately 0.5 mm length and 0.001" to 0.0015" wall thickness) positioned approximately 0.5 mm mm proximal of the distal end and encapsulated by the outer thermoplastic polyurethane layer 139 to form an atraumatic tip.

With reference to FIG. 15F, the outer 140 is shown in more detail. Like the inner 130, the outer 140 may comprise a multi-layered tube with gradually increasing zones of flexibility in the distal direction. For example, the outer 140 may include a proximal section 142 having a length of about 100 cm and an outside diameter of about 0.073" comprising an inner PTFE liner (e.g., PTFE with PEBAX top coat; 0.072" inside diameter; 0.00075 wall thickness), a wire braid middle layer (e.g., 16 carriers of 0.0015" diameter round wire (or 0.001"×0.003" flat wire) made of 304v/300 KPSI stainless steel, paired and braided at 50 picks per inch) and a thermoplastic polyamide outer layer (e.g., Grilamid L20; with a wall thickness inclusive of braid of 0.003" to 0.005", preferably 0.004"). Extending from the proximal section 142, the outer 140 may further include a transition section 144 having a length of about 5.0 cm and an outside diameter of about 0.083" comprising the same layers as proximal section 142 except the outer layer may comprise a thermoplastic elastomer (e.g., PEBAX 7233; with a wall thickness inclusive of braid of 0.003" to 0.005", preferably 0.004"). Extending from the transition section 144, the outer may further include a distal section 146 having a length of about 5.0 cm and an outside diameter of about 0.083" comprising the same layers as transition section 144 except the outer layer may comprise a softer thermoplastic elastomer (e.g., PEBAX 5533; with a wall thickness inclusive of braid of 0.003" to 0.005", preferably 0.004"). The braid layer may terminate at the end of the end of the distal section 146 to define a distal extension 148 extending about 5.0 mm to 7.0 mm therefrom that includes the same layers as distal section 146 but excludes the braid and PTFE layers. A short tube 147 (e.g., PET; 2 mm to 5 mm length, 0.0004" wall thickness) may be placed over the distal end of the braid layer at the junction between the distal section 146 and distal extension 148 to prevent the braid from protruding post reflow. The various layers may be thermally re-flowed together using FEP heat shrink and cyanoacrylate adhesive where necessary to tack the various components.

When the BASC 100 is fully advanced as shown in FIG. 5, the proximal section 142 may extend through the FA, AAo and AA to the CC, and the transition section 144 may extend from the CC to C1 of the ICA. The balloon 120 may be positioned in C1-C3 of the ICA, and the distal extension 114 may extend through C1 to C5 of the ICA (depending on the position of the balloon 120), with the distal end residing in C3 to C5 of the ICA.

Neuro Access and Support Catheter (NASC)

Figure 16:
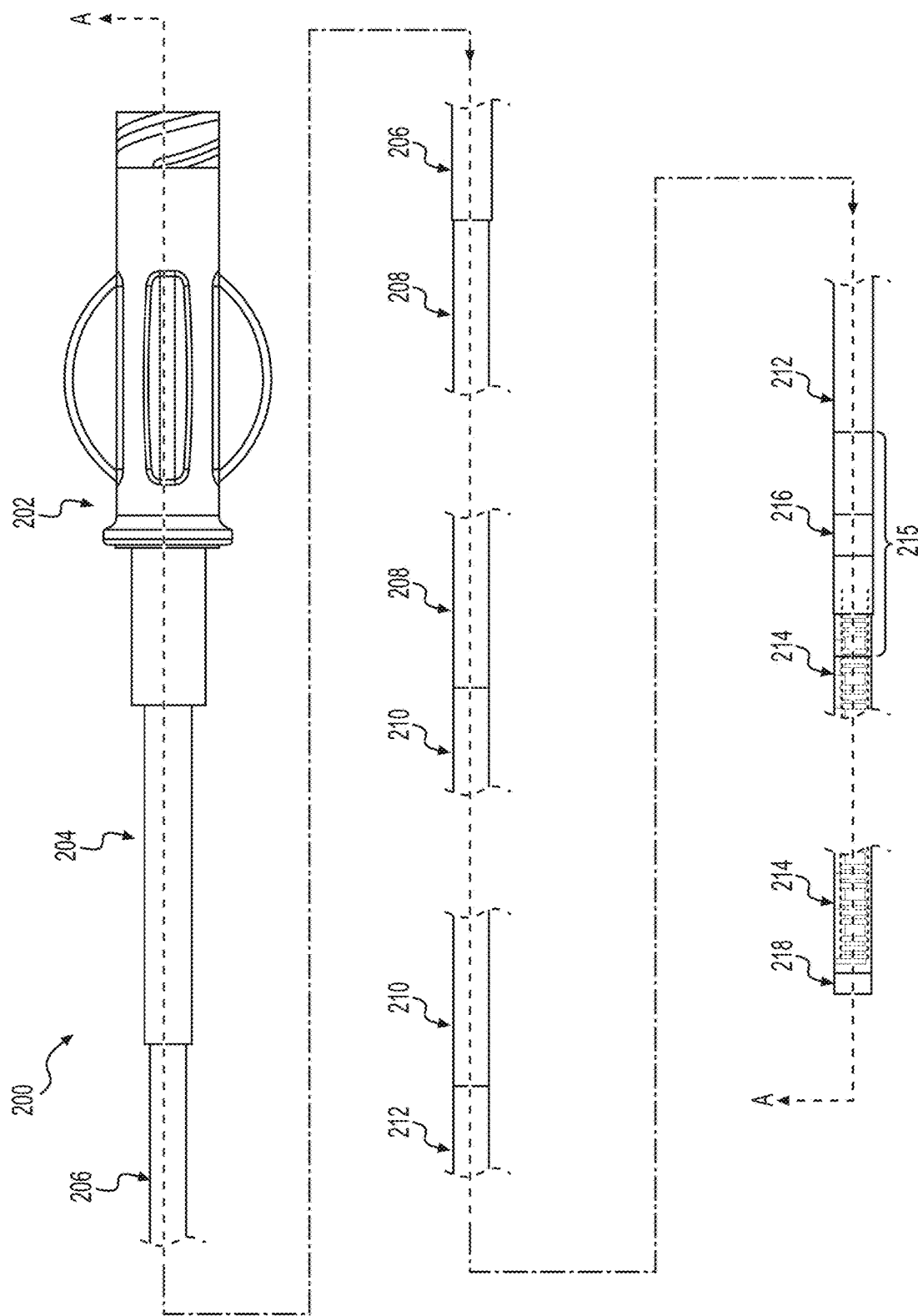

With reference to FIG. 16, the NASC 200 is shown schematically. NASC 200 may include a single port hub 202 comprising molded PET (e.g. Tritan MX 731) and a polyolefin heat shrink strain relief 204 connected to the proximal end of a tubular shaft. The tubular shaft may comprise multilayered materials with gradually increasing flexibility in the distal direction over an overall length of about 125 cm with an inside diameter of about 0.059 in. The shaft may include a first proximal support section 206 about 94 cm long with an outside diameter of about 0.081" which may comprise layers of thermoplastic elastomer (e.g., PEBAX 63D; 0.002-0.004" wall thickness) over polyamide (e.g., Grilamid L20; 0.005-0.007" wall thickness) over stainless steel braid (e.g., 16 carrier×0.002" diameter paired wires at 50 picks per inch diamond pattern) over an inner liner of PTFE (e.g., 0.00075" wall thickness, 0.059" inside diameter). From the first proximal support section 206, a second proximal support section 208 extends about 6.0 cm long with an outside diameter of about 0.075" and may comprise the same layers as first proximal support layer 206 excluding the outermost thermoplastic layer. From the second proximal support section 208, a third proximal support section 210 extends about 5.0 cm long with an outside diameter of about 0.073" and may comprise the same layers as second proximal support section 208 except the outermost polyamide layer is replaced by a thermoplastic elastomer layer (e.g., e.g., PEBAX 72D; 0.004-0.006" wall thickness). From the third proximal support section 210, a proximal transition section 212 extends about 3.0 cm long with an outside diameter of about 0.073" and may comprise the same layers as third proximal support section 210 except the outermost thermoplastic elastomer layer may comprise a softer thermoplastic elastomer (e.g., e.g., PEBAX 55D; 0.003-0.005" wall thickness). From the proximal transition section 212, a distal transition section 215 extends about 4.0 cm long with an outside diameter of about 0.072" and may comprise an outer layer of thermoplastic polyurethane (e.g., Pellethane 80E; 0.003-0.005" wall thickness) and an inner liner of PTFE (e.g., 0.00075" wall thickness, 0.059" inside diameter). Between the outer and inner layers of distal transition section 215, the braid of proximal transition section 212 continues for about 3 cm and transitions to about 1 cm of the coil of distal section 214, with about 1 mm of overlap. In the distal transition section 215, a PET heat shrink 216 may be placed under the thermoplastic polyurethane layer and over the junction where the braid covers the coil to bridge the sections together. The distal section 214 extends about 13.5 cm long with an outside diameter of about 0.068" and may comprise an outer layer of thermoplastic polyurethane (e.g., Tecothane AR-62A; 0.002-0.004" wall thickness) over a coiled, super-elastic nickel titanium wire (e.g., 0.0015-0.0020" diameter Nitinol wire coiled at 0.006" pitch) over an inner liner of PTFE (e.g., 0.00075" wall thickness, 0.059" inside diameter). From the second distal section 214, a distal tip 218 extends about 1.5 mm long with an outside diameter of about 0.069" which may comprise the same thermoplastic polyurethane outer layer used in the second distal section 114 over a radiopaque marker band (e.g., 90/10 Pt—Ir; 0.5 mm long) abutting the distal end of the pattern-cut super-elastic tube over the same PTFE inner liner. The various layers may be thermally re-flowed together using FEP heat shrink and cyanoacrylate adhesive where necessary to tack the various components.

FIG. 16A, which is a longitudinal cross-section of the NASC 200 taken along line A-A in FIG. 16, and FIG. 16B, which is a detailed view of the distal section 214 and distal tip 218 taken along circle B in FIG. 16A, show the layers of the NASC 200 in greater detail, particularly the distal layers. Specifically, as best seen in FIG. 16B, the distal section 214 includes an inner PTFE liner 222 and an outer thermoplastic polyurethane 228. A radiopaque marker band 224 is encapsulated between inner and outer layers, with the inner layer 222 terminating under the marker band 224 and the outer layer 228 continuing to form the distal tip section 218. The proximal end of the marker band abuts or covers the distal end of a super-elastic coil 226 that is also encapsulated between the inner and outer layers. Optionally, a longitudinal member (not shown) such as a polyester suture may be positioned between the inner layer 222 and coil 226 and extend to the marker band 224 to increase the tensile strength of the distal section 214.

As mentioned previously, the NASC 200 may be used instead of the BASC 100 as described with reference to FIGS. 1-14. When the NASC 200 is fully advanced as shown in FIG. 5, first proximal support section 206 may extend through the FA, AAo and AA to the CC, and the second proximal support section 208 may extend from the CC to C1 of the ICA. The third proximal support section 210 and the proximal transition section 212 may extend through C2 and C3 of the ICA, and the distal section 214 may extend through C4 and C5 of the ICA, with the distal tip 218 residing in C5 of the ICA.

Figure 16C:
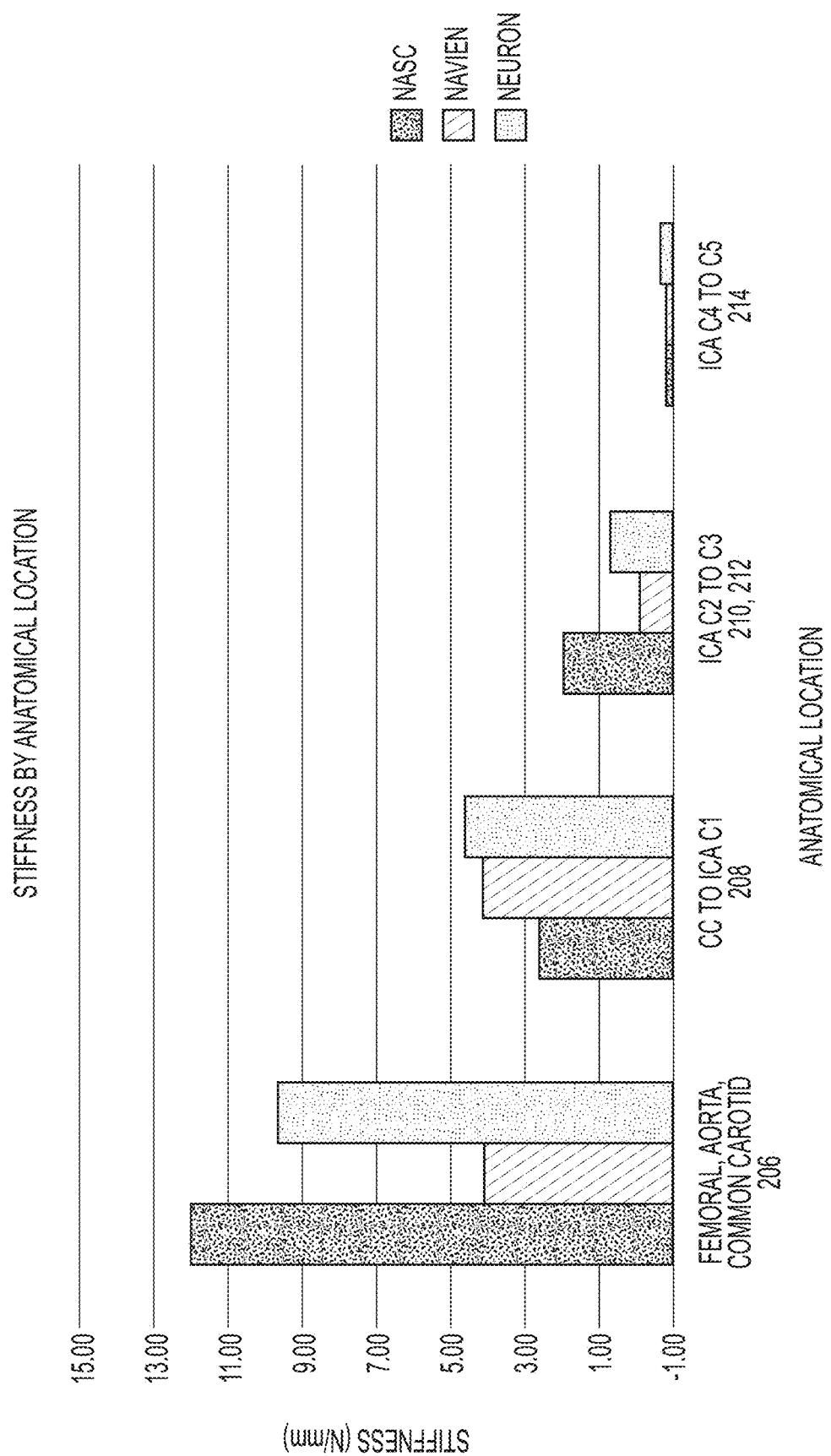
FIG. 16C is a chart showing a stiffness profile of a neuro access and support catheter according to an embodiment, and stiffness profiles of existing devices.

The stiffness of each of sections 206, 208, 210, 212 and 214 may be configured to provide the desired performance as a function of the anatomical locations described above. Based on a 3-point bend test according to ASTM Standard F2606, the first proximal support section 206 may have a stiffness of about 4.0-9.0 N/mm, or preferably 7.0-8.0 N/mm, which provides a balance of efficient power transfer to sections 208, 210, 212 and 214 while avoiding prolapse in the AA. The second proximal support section 208 may have a stiffness of about 1.5-4.0 or preferably 2.0-3.0 N/mm in order to provide a balance of flexibility in the ICA and supporting devices extending therethrough while avoiding back-out of distal sections 212 and 214. The third proximal support section 210 and the proximal transition section 212 may have a stiffness of about 1.0-3.0 N/mm or preferably 1.5-2.5 N/mm in order to provide a balance of flexibility and support, as well as a more gradual stiffness transition to the distal section 214. The distal section 214 may have a stiffness of about 0.15-0.50 or preferably 0.2-0.4 N/mm in order to maintain support and power transfer up to C5. An example of the stiffness profile of the NASC 200 compared to two prior art devices (Navien made by ev3; Neuron made by Pnenumbra) is shown in FIG. 16C.

Rapid Exchange (RX) Neuro Access and Support Catheter (NASC)

Figure 16D:
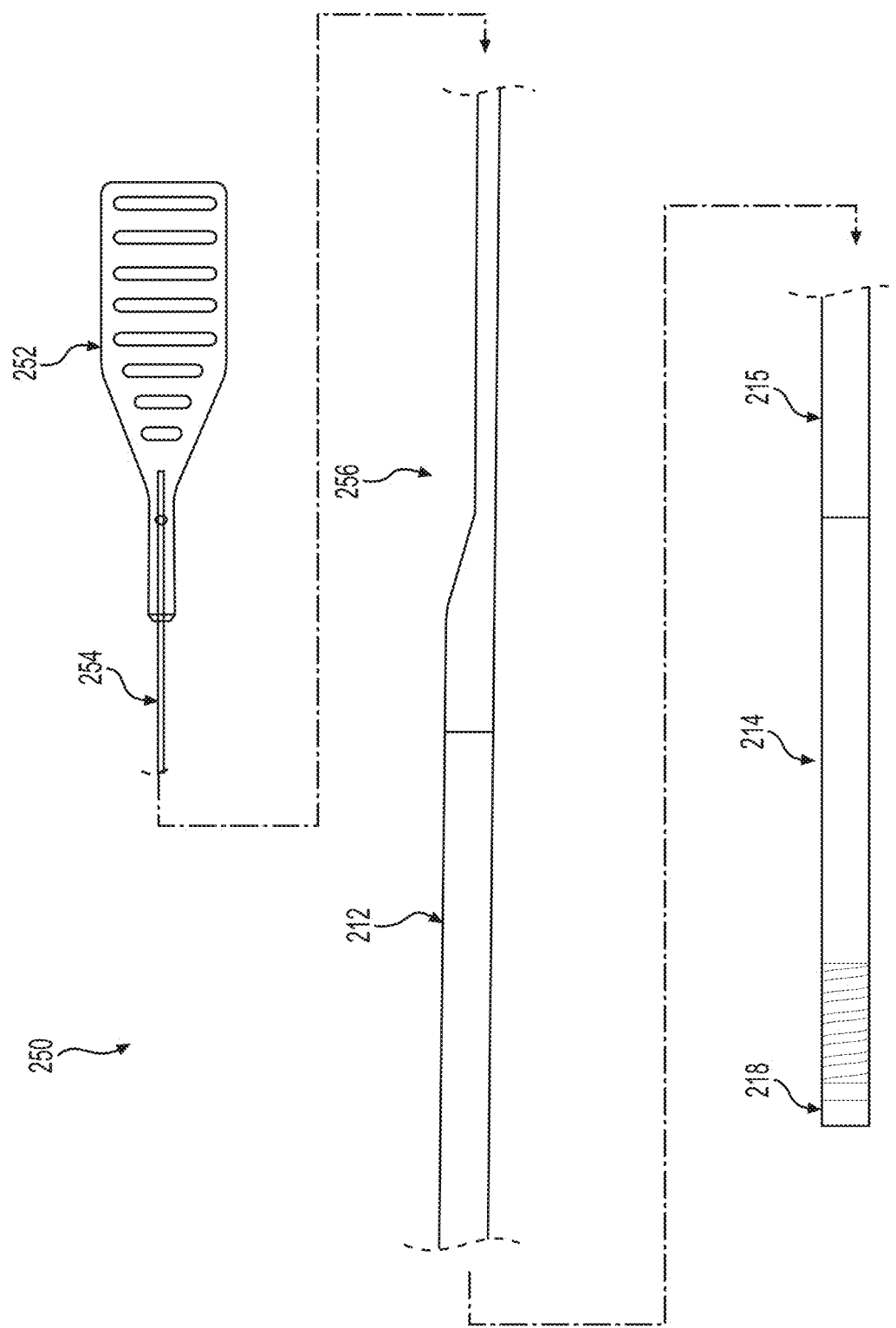

With reference to FIG. 16D, a RX NASC 250 is shown schematically. RX NASC 250 is similar the NASC 200 but in a rapid exchange configuration. In general, the RX NASC 250 substitutes the proximal shaft sections of the NASC 200 with a wire 254 (e.g., 304v ultra spring temper stainless steel) and tab 252, while the distal shaft sections of the RX NASC 250 may be the same or similar, in terms of construction and materials, to the proximal transition section 212, distal transition section 215, distal section 214 and distal tip 218 of the NASC 200. The distal end of the wire 254 may be connected to a junction 256 which, in turn, may be connected to the proximal end of the proximal transition section 212. The junction 256 may comprise a single layer of thermoplastic elastomer (e.g., PEBAX 72D; 3.39" long, 0.004"-0.005" wall thickness; no PTFE liner). The wire 254 may be bonded to the junction 256 by thermally reflowing the polymer layer over the wire 254.

With reference to FIGS. 16E and 16F, where FIG. 16E is a schematic side view and FIG. 16F is a schematic top view, a port in junction 256 may be formed by two skive cuts defining proximal step 262 and distal step 264. The wire 254 may extend through the proximal step 262 and distal step 264, stopping short of the proximal transition section 212 to avoid compromising the luminal opening into the proximal transition section 212. By way of example, the skive cuts may be made at an angle of 15 degrees and may be spaced about 1.0" apart, with a distal cut depth of about 60% of the overall diameter, and a proximal cut depth of about 80% of the overall diameter, where the overall diameter depends on the size of the catheter desired.

By way of example, not limitation: a 4 French RX NASC 250 may have an inside diameter of 0.045" and an outside diameter of 0.055"; a 5 French RX NASC 250 may have an inside diameter of 0.059" and an outside diameter of 0.069"; a 6 French RX NASC 250 may have an inside diameter of 0.073" and an outside diameter of 0.083"; and a 7 French RX NASC 250 may have an inside diameter of 0.086" and an outside diameter of 0.095".

With reference to FIGS. 16G-16I, cross-sectional views of the wire 254 are shown schematically. By way of example, the cross-section of the wire 254 may have a rounded rectangular shape (FIG. 16G), a rounded D shape (FIG. 16H) or a rounded crescent shape (FIG. 16I). The wire may have a cross-sectional dimension of 0.008" by 0.020" for smaller diameter catheters or 0.012" by 0.035" for larger diameter catheters, for example.

The RX NASC 250 provides a number of advantages over conventional intermediate catheters. The following advantages are given by way of example, not limitation.

First, using a proximal wire 254 eliminates a proximal tubular shaft and thus provides improved infusion and aspiration. In other words, the absence of a proximal tubular shaft leaves the entire (larger) lumen of guide sheath available for infusion/aspiration. Further, a close distal fit between the RX NASC and the guide sheath ensures that a majority of the aspiration happens at the distal tip of the RX NASC 250.

Second, a shorter overlap length between the tubular sections of RX NASC 250 with guide sheath allows the RX NASC 250 to be up-sized without up-sizing the guide sheath. In other words, the RX NASC 250 can be larger and therefore tighter fitting to guide sheath without introducing drag/friction and without compromising flushing. For example, a conventional 5F intermediate catheter is often used with a 6F guide sheath to provide a relatively large annular gap (e.g., 0.008" gap) to allow flushing and minimize drag between the devices. While a 6F conventional intermediate catheter can be used with a 6F guide sheath, the resulting annular gap is relatively small (e.g., 0.002" gap) that introduces drag and compromises flushing. A 6F RX NASC 250 can be used with a 6F guide sheath without introducing excessive drag or compromising flushing; less drag translates to better catheter movement and an upsized intermediate catheter provides a larger working ID for procedures requiring larger devices.

Third, the RX NASC 250 has a rapid exchange configuration by virtue of its side port at junction 256, and thus may be introduced over a conventional length guidewire as opposed to an exchange length guidewire.

Fourth, the wire 254 of the RX NASC 250 eliminates a separate flush port. Because the RX NASC 250 uses a wire 254 in place of a proximal tubular section that would otherwise require a separate hub and hemostasis adapter for flushing, the RX NASC 250 may be flushed via the guide sheath flush port. Essentially, two catheters can be flushed simultaneously through a single y-adapter, and the RX NASC 250 is compatible with 3 port hemostasis adapters.

Fifth, the wire 254 of the RX NASC may be made in one size to fit a variety of conditions. Conventional intermediate catheters come is various lengths (e.g. 115, 120, 125, 130 cm lengths) to be compatible with different guide sheaths and different procedures. Having one size wire 254 sufficiently long to be compatible with all guide sheaths and other devices eliminates the need to stock multiple lengths of intermediate catheters and thereby reduces hospital inventory.

Sixth, the unique configuration of the RX NASC 250 may be used in other applications, such as coronary and peripheral procedures.

Over-the-Wire (OTW) Aiming Microcatheter (AMC)

Figure 17:
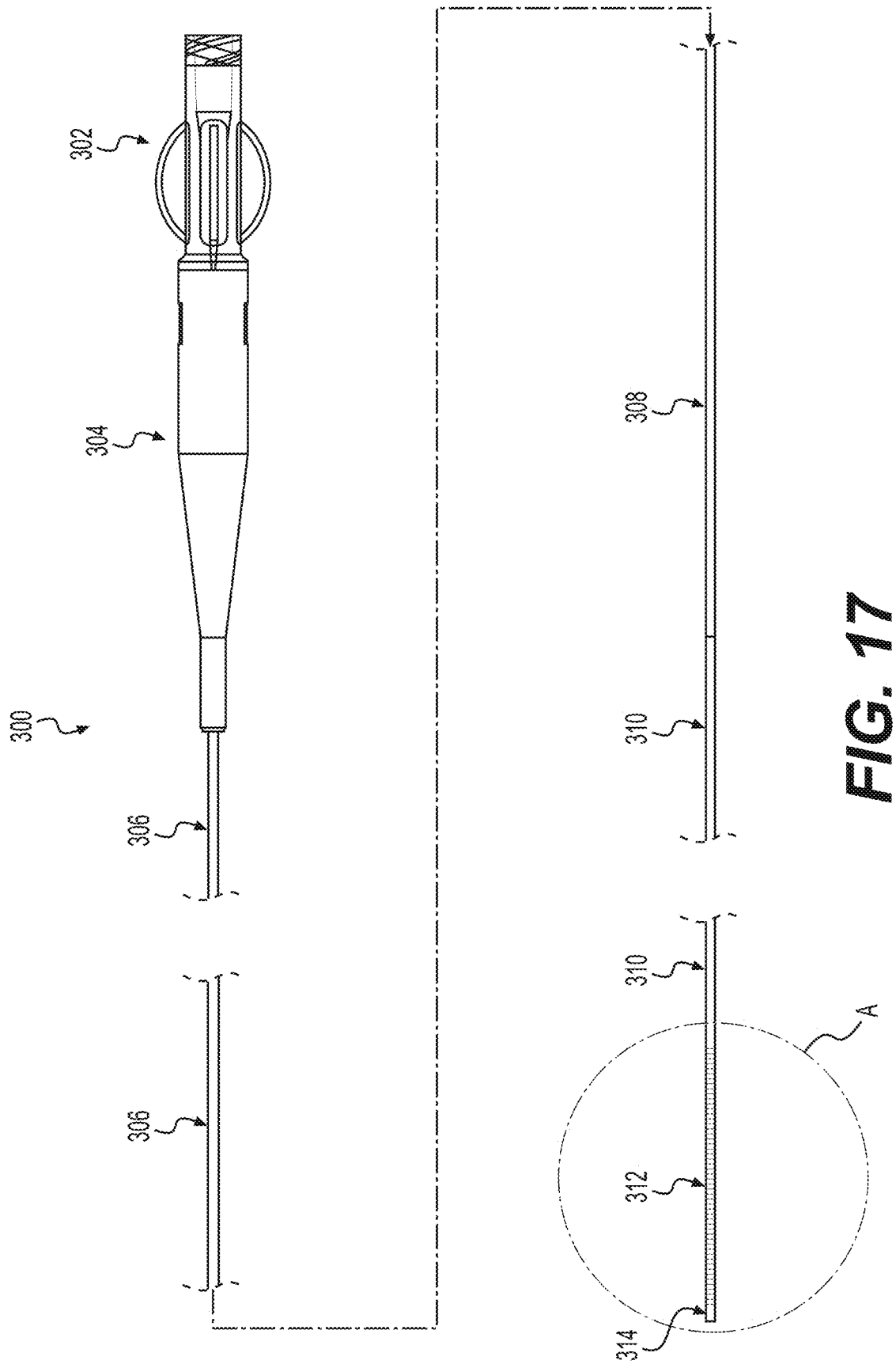

With reference to FIG. 17, the OTW AMC 300 is shown schematically. OTW AMC 300 may include a single port hub 302 comprising molded PET (e.g. Tritan MX 731) and a molded thermoplastic elastomer (e.g., PEBAX 3533) strain relief 304 connected to the proximal end of a tubular shaft. The tubular shaft may comprise multilayered materials with gradually increasing flexibility in the distal direction over an overall length of about 150 cm with an inside diameter of about 0.0165 in. to accommodate 0.010" and 0.014" guidewires.

The shaft may include a proximal section 306 about 80 cm long with an outside diameter of about 0.034" which may comprise layers of thermoplastic elastomer (e.g., PEBAX 7233; approximately 0.003" wall thickness) over a dual layer coil over a single layer braid (e.g., spring temper 304v stainless steel; 16 carrier of 0.0005"×0.0025" ribbon at 175 picks per inch, diamond pattern) over an inner liner (e.g., PTFE, 0.00075" wall thickness; 0.019" inside diameter stretched down over a mandrel having a diameter of 0.0165"). The dual layer coil may comprise helical hollow strand 304v stainless steel wire, with the first layer comprising 18 carriers of 0.0012" diameter wires wound in a right-hand direction and the second layer comprising 18 carriers of 0.0014" diameter wires wound in a left-hand direction, wherein the wound wire layers have 0.0075"-0.0080" spaced gaps. The first and second layers may be swaged down to an overall thickness of about 0.0012", wherein the swaging process causes the round wires to become elliptical in cross-section.

From the proximal section 306, a mid-section 308 extends about 40.0 cm long with an outside diameter of about 0.034" and may comprise the same layers as proximal section 306 except the outer layer may comprise a softer thermoplastic elastomer (e.g., PEBAX 5533; approximately 0.003" wall thickness). From the mid-section 308, a distal section 310 extends about 30.0 cm long with an outside diameter of about 0.034" and may comprise the same layers as mid-section 308 except the outer layer may comprise an even softer thermoplastic elastomer (e.g., PEBAX 3533; approximately 0.003" wall thickness).

From the distal section 310, a distal tip section 312 extends about 1.5 cm with an outside diameter that tapers from 0.034" to 0.0295" and with a minimum inside diameter of 0.016". The distal tip section 312 may comprise an outer layer of thermoplastic elastomer (e.g., PEBAX 3533; approximately 0.002" wall thickness) over a single layer coil 316 over the same inner liner (e.g., PTFE, 0.00075" wall thickness, 0.019" inside diameter). As seen in FIG. 17D, the coil 316 may comprise 92% Platinum 8% Tungsten wire of 0.0025" diameter wound with a variable pitch. The pitch may vary from 0.0035" for the proximal 0.275", 0.0070" for the middle 0.275" and 0.0025" (closed gap) for the distal 0.020" to act as a radiopaque marker band. Alternatively, the coil may comprise 304v spring temper stainless steel 0.001"×0.005" ribbon wound with a constant pitch of 0.0085" with a radiopaque marker band swaged on its distal end. The distal tip section 312 may include a 1 mm long distal bumper tip 314 comprising a continuation of the inner and outer layers without the coil (i.e., the coil and/or marker band terminate 1 mm shy of the distal end).

Figure 17A:
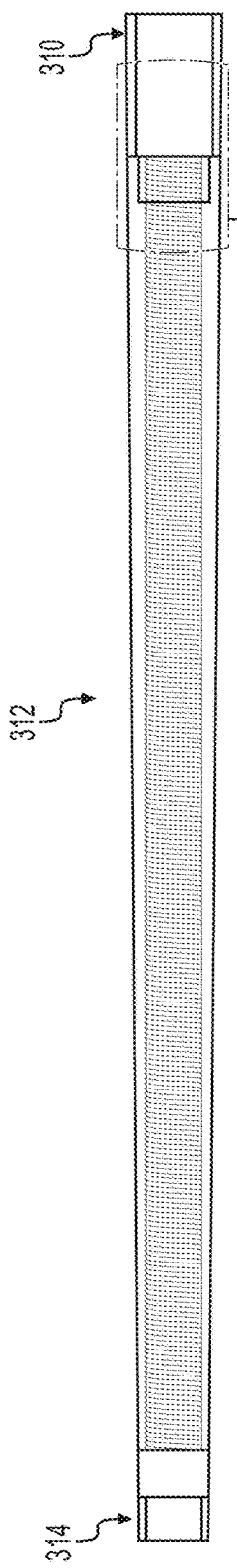
Figure 17B:
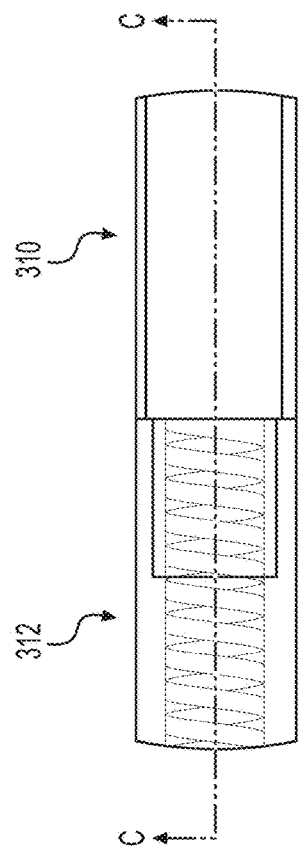
Figure 17C:
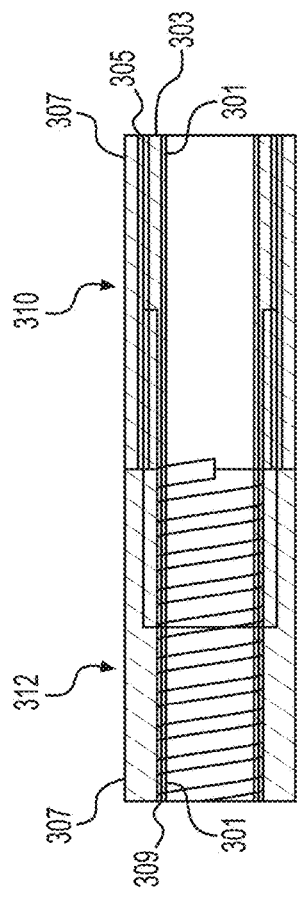

With reference to FIG. 17A which is a detailed view taken along circle A in FIG. 17, FIG. 17B which is a detailed view taken along box B in FIG. 17A, and FIG. 17C which is a cross-sectional view taken along line C-C in FIG. 17B, further detail of the junction between distal section 310 and the distal tip section 312 is shown. With specific reference to FIG. 17C, the inner liner 301 of the distal section continues through both the distal section 310 and the distal tip section 312. The braid 303 terminates at the distal end of the distal section 310 and abuts the proximal end of the coil 309 of the distal tip section 312. Where the distal end of the braid 303 abuts the proximal end of the coil 309, one of the layers (e.g., inner layer) of the dual layer coil 305 may terminate and the other layer (e.g., outer layer) may extend across the abutment to provide a smooth transition, as shown in FIG. 17E. The outer layer 307 encapsulates the coil layers 305 and 309 of both sections 310 and 312.

With reference to FIGS. 18A-18H, which are schematic illustrations of the distal tip section 312 of the OTW AMC 300, the distal tip section 312 may be formed into a variety of different shapes. For example, the distal tip section 312 may be straight 330 as shown in FIG. 18A, or may have a 45 degree bend 332 as shown in FIG. 18B, a 90 degree bend 334 as shown in FIG. 18C, or a 180 degree bend 336 as shown in FIG. 18D. Alternatively, more complex shapes may be employed. For example, the distal tip section 312 may have a shepherd's hook shape 338 as shown in FIG. 18E, or an abbreviated shepherd's hook shape 340 (where the end does not curve out) as shown in FIG. 18F. Other shapes may be used depending on the specific anatomy being navigated.

For purposes of accessing the OA via the ICA, particularly when the OA take-off angle from the ICA is at a right angle or a slightly rearward angle, the shepherd's hook 338 shown in FIG. 18E may have an overall length L of approximately 10-15 mm and preferably about 12 mm; a primary curve 342 radius R1 of approximately 7.5-15 mm and preferably about 10 mm (to approximate one half the inside diameter of the ICA); and an arc length of approximately 35-55 degrees, preferably about 45 degrees; a secondary curve 344 radius R2 of approximately 2-3 mm and preferably about 2 mm (to approximate the inside diameter of the ICA) and an arc length of about 170 to 190 degrees and preferably 180 degrees; and a tertiary curve 346 radius R3 1.0 mm and an arc length of about 15 to 30 degrees. This configuration enables the distal tip 314 to cannulate the OA and the outside surface of the secondary curve rests against the opposite wall of the ICA. The tertiary curve 346 may be eliminated to form an abbreviated shepherd's hook shape 340 as shown in FIG. 18F in the event the OA take-off angle is more rearward. The primary, secondary and tertiary curves may be co-planar.

These shapes maybe pre-formed by the manufacturer or formed by the physician during use utilizing heat-set techniques known in the art. A unique heat-set technique discovered by the inventors may be employed to improve shape retention. The technique involves placing the distal tip section 312 over an annealed stainless-steel mandrel pre-formed to the desired shape (e.g., abbreviated shepherd's hook). Alternatively, the distal tip section 312 may be placed into a groove in a metal forming plate, where the groove pattern corresponds to the desired shape. While on the pre-formed mandrel on in the groove of the forming plate, the distal tip section 312 is then exposed to heat (e.g., airflow) at or above the mechanical relaxation point of the polymers. Since PTFE has the higher mechanical relaxation temperature of the polymers used, the target temperature may be selected to achieve mechanical relaxation of the rigid amorphous fraction (RAF) phase of PTFE, corresponding to a temperature range of approximately 210 to 250 degrees F. In this example, the distal tip section 312 is then exposed to airflow at 210 to 230 degrees F. for 5 to 8 minutes. Immediately after heating, and while still on the pre-formed mandrel on in the groove of the forming plate, the distal tip section 312 is cooled below ambient temperature to lock in the desired shape. In this example, the distal tip section 312 is quenched in an ice bath approximating 32 to 45 degrees F. for 5 to 8 minutes.

Rapid Exchange (RX) Aiming Microcatheter (AMC)

Figure 19:
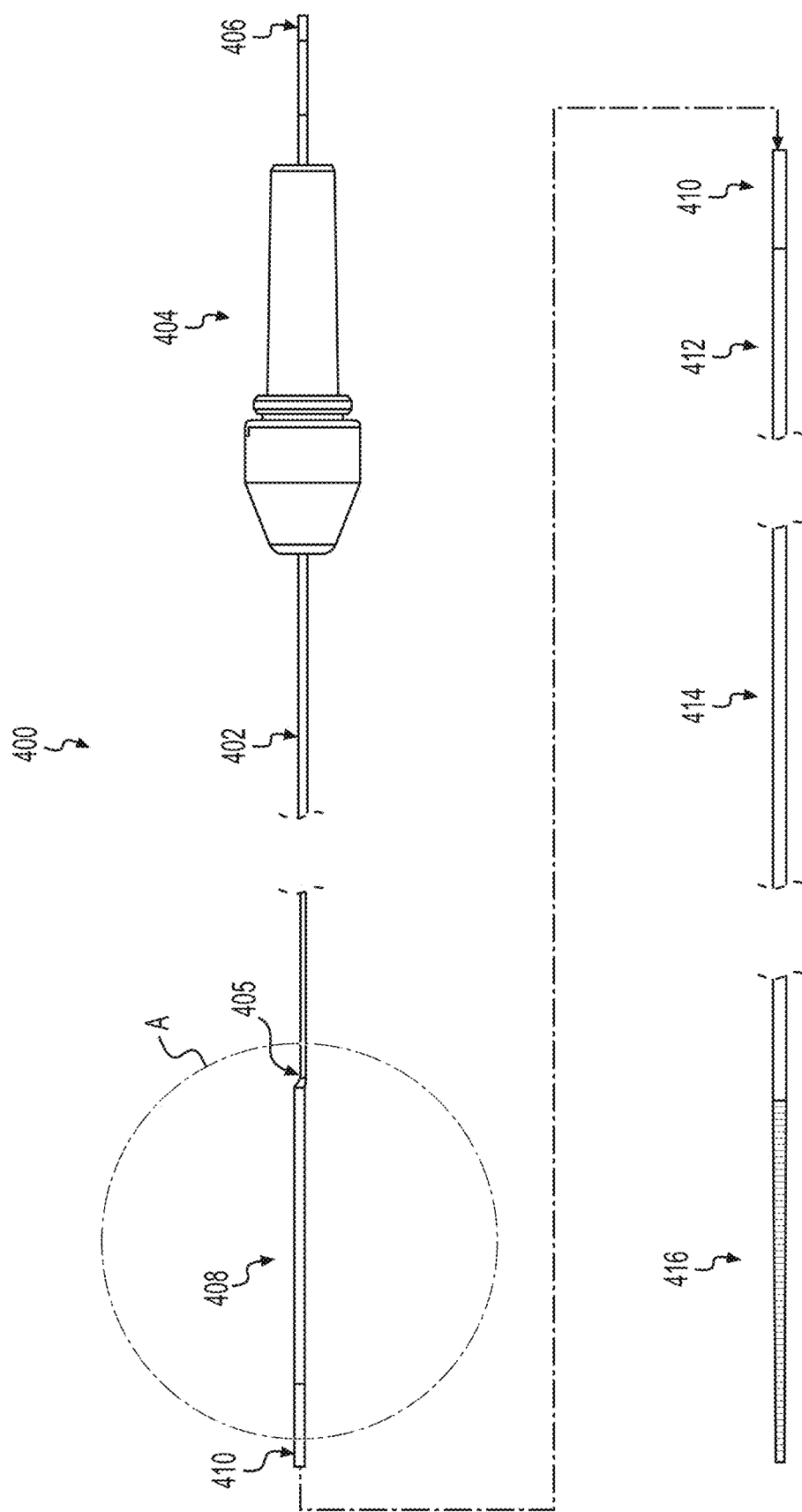

With reference to FIG. 19, the RX AMC 400 is shown schematically. The RX AMC 400 is similar in function as OTW AMC 300 described previously but is designed to facilitate exchange over a conventional length (e.g., 150 cm) guidewire without the need for an exchange length (e.g., 300 cm) guidewire making it easier and faster for the physician. Whereas the guidewire exits the proximal end of the OTW AMC 300, the guidewire exits a side port 405 in the RX AMC 400 located closer to the distal end, thus enabling the rapid exchange functionality. Because the guidewire exit port 405 is located closer to the distal end, the proximal shaft portion 402 of the RX AMC 400 does not need to accommodate a guidewire, and thus may comprise a solid core push wire (e.g., 304v stainless steel, spring temper) having an overall length of about 100 cm. A torque device 404 may be disposed on the push wire 402 to manipulate the RX AMC 400 when in use. The proximal end of the push wire 402 may be covered with polyolefin heat shrink tubing to render it blunt. The push wire may have an outside diameter of 0.023" for the proximal 90 cm, followed by a taper down to 0.010" over the next 10 cm. The distal 1 cm or so may be stamped into a cupped ribbon having a width of 0.023" and a thickness of 0.003" for insertion and attachment to the first distal shaft section 408.

Distal tubular shaft sections 408, 410, 412, 414 and 416 may comprise multilayered materials with gradually increasing flexibility in the distal direction over an overall length of about 53 cm with an inside diameter of about 0.0165 in. to accommodate 0.010" and 0.014" guidewires. First distal section 408, the proximal end of which defines the guidewire port 405, may have a length of about 3 cm and an outside diameter of 0.034" comprising the following layers: polyester heat shrink (e.g., PET; inside diameter 0.055"; wall thickness 0.0005") over a dual layer coil over a single layer braid over an inner liner. The dual layer coil, single layer braid and inner liner may comprise the same materials and construction as described with reference to the OTW AMC 300.

Extending from the first distal section 408, second distal section 410 may have a length of about 5 cm and an outside diameter of about 0.034" comprising the same layers as first distal section 408 except the outer layer may comprise a thermoplastic elastomer (e.g., PEBAX 7233; approximately 0.003" wall thickness). Extending from the second distal section 410, third distal section 412 may have a length of about 15 cm and an outside diameter of about 0.034" comprising the same layers as second distal section 410 except the outer layer may comprise a softer thermoplastic elastomer (e.g., PEBAX 5533; approximately 0.003" wall thickness). Extending from the third distal section 412, fourth distal section 414 may have a length of about 30 cm and an outside diameter of about 0.034" comprising the same layers as third distal section 412 except the outer layer may comprise an even softer thermoplastic elastomer (e.g., PEBAX 3533; approximately 0.003" wall thickness).

From the fourth distal section 414, a distal tip section 416 extends about 1.5 cm with an outside diameter that tapers from 0.034" to 0.0295" and with a minimum inside diameter of 0.016". The distal tip section 416 may comprise the same materials and construction as described with reference to distal extension 312 of the OTW AMC 300 and may be formed into any of the shapes described with reference to FIGS. 18A-18F.

With reference to FIG. 19A which is a detailed view taken along circle A in FIG. 19, further detail of the junction between push wire 402 and the first distal section 408 is shown schematically. To form this junction, the push wire 402 is loaded under the thermoplastic and reflowed, then covered in PET.

Rapid Exchange (RX) Micro Balloon Catheter (MBC)

Figure 20:
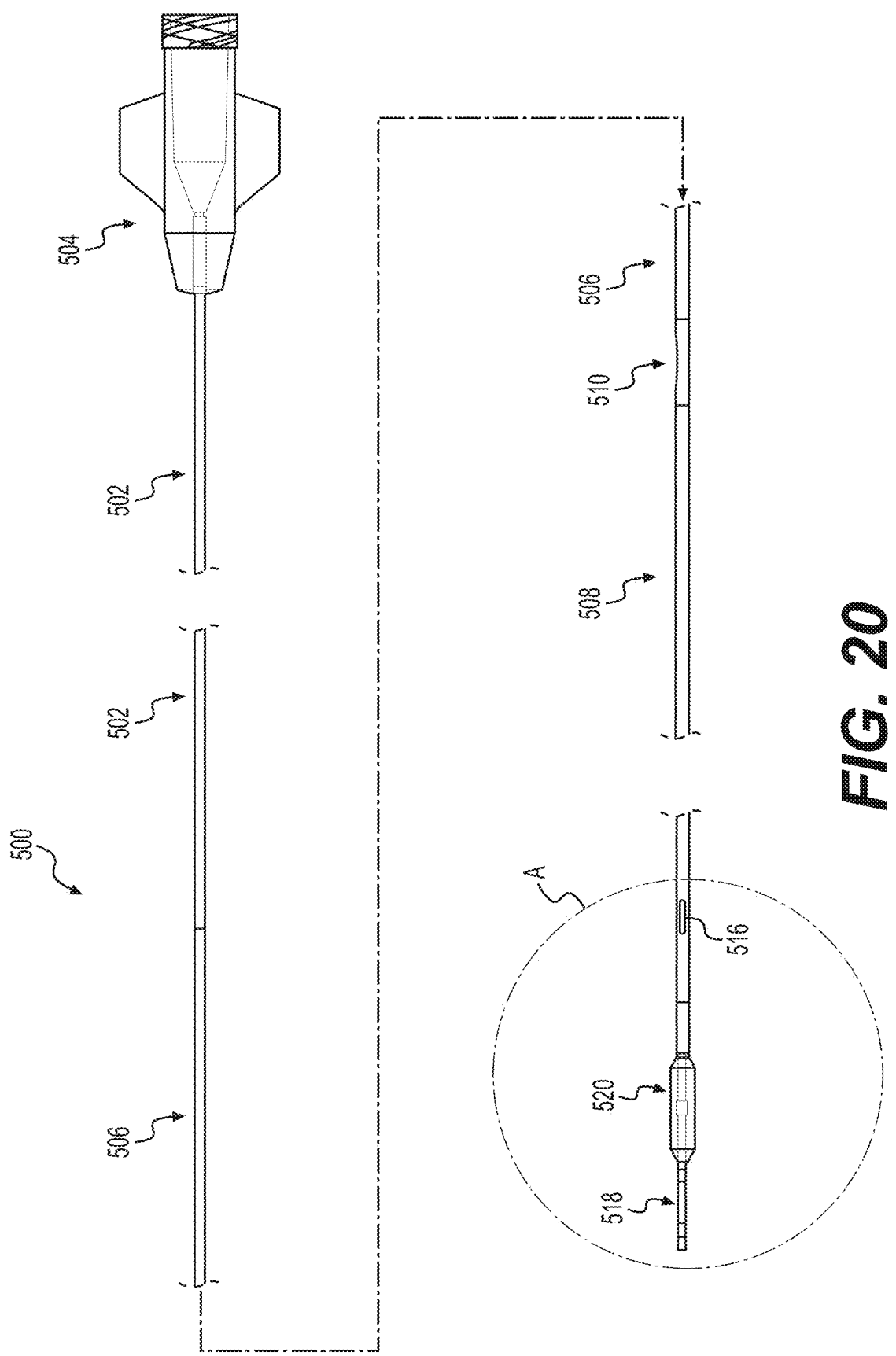

With reference to FIG. 20, the RX MBC 500 is shown schematically. RX MBC is similar to RX AMC 400 in that it is designed to facilitate exchange over a conventional length (e.g., 150 cm) guidewire without the need for an exchange length (e.g., 300 cm) guidewire making it easier and faster for the physician. The guidewire exits a side port 510 in the MBC 500 located closer to the distal end, thus enabling the rapid exchange functionality. Because the guidewire exit port 510 is located closer to the distal end, the proximal shaft section 502 of the MBC 500 does not need to accommodate a guidewire, and thus may comprise a single lumen hypotube (e.g., 304v stainless steel, spring temper, 112.5 cm length, 0.017" ID, 0.023" OD, PTFE coated). The single lumen in the proximal shaft 502 may be used to inflate and deflate the balloon 520 via hub 504 connected to an inflation device (not shown).

A mid-shaft section 506 (e.g., 7233 Pebax, 0.030" ID, 0.003" wall thickness) may extend approximately 17 cm from the proximal shaft 502, with about 10 mm overlapping and thermally bonded to the proximal shaft 502. A core wire (not visible) (spring temper 304v stainless steel) may extend about 18 cm from the proximal shaft 502 inside the mid-shaft 506, with about 5 cm of the proximal end of the core wire extending inside the proximal shaft 502 and secured thereto by an interference fit. The core wire may have a nominal diameter of 0.010" with the proximal 5 cm centerless ground to 0.006" diameter and bent at two 30-degree angles to form the interference fit with the inside surface of the proximal shaft 502. The distal 3 cm of the core wire may be centerless ground to 0.004" diameter to provide a gradual stiffness transition across the guidewire exit port 510.

A distal shaft section 508 may extend approximately 30 cm from the mid-shaft section 506, and the junction between the two may form the guidewire port 510. The distal shaft section 508 may include an inner 514 and a distal outer 512 which are shown in more detail in FIGS. 20A-20C. As shown in those figures, the inner 514 and the distal outer 512 are co-axial. The inner extends from the guidewire port 510, through the balloon 520 to define a distal tip 518. The distal outer 512 extends from the guidewire port 510 to the proximal end of the balloon 520. At the guidewire port 510, the inner 514 exits the distal outer 512, but otherwise extends inside the distal outer 512 and balloon 520.

To form the junction between the mid-shaft 506 and the distal shaft 508, the proximal end of the distal outer 512 may be square-cut with the inner 514 extending slightly proximal thereof. The distal end of the mid-shaft 506 may be skive-cut at a 30 to 45 degree angle and positioned around the distal outer 512 with the inner 514 projecting out therefrom. A round support mandrel may be placed in the inner 514 extending out the proximal end thereof. A crescent-shaped support mandrel may be inserted in the mid-shaft 506 extending out the distal end thereof into the distal outer 512 with the inner 514 resting inside the saddle of the crescent-shape. The junction may be thermally reflowed to create a sealed thermal bond between the components with the inner 514 exiting the outer 512 where the outer 512 and midshaft 506 come together. Optionally, this sealed junction may be configured to burst at a pressure that is lower than the burst pressure of the balloon 520. In this manner, as the inflation pressure exceeds (by, e.g., 1-4 ATM) the nominally rated inflation pressure of the balloon 520 (i.e., the pressure at which the balloon reaches its specified inflated diameter), the sealed junction will burst rather than the balloon 520. When in use, a burst failure of the junction will harmlessly occur inside the guide or intermediate catheter (substantially proximal of the balloon), rather than at the balloon 520 inside the vasculature where a burst is less safe. This is particularly beneficial for a non-compliant balloon (growth rate of 4% to 6% over its working range (nominal to rated burst pressure)).

With reference to FIGS. 20A-20C, the details of the distal portions of the MBC 500 may be seen more clearly. FIG. 20A is a detailed view of circle A shown in FIG. 20; FIG. 20B is a detailed view of circle B shown in FIG. 20A, and FIG. 20C is a longitudinal sectional view taken along line C-C in FIG. 20B. The distal outer 512 may comprise a thermoplastic elastomer (e.g., Pebax 5533 or 7233, 0.030" ID, 0.003" wall thickness). The inner 514 may comprise a multilayered construction with an inner liner 542 (e.g., etched PTFE, 0.00075" wall), a coil middle layer 544 (e.g., spring temper 304v stainless steel, 0.001"×0.005" flat wire, 0.0085" pitch, 0.019" ID, 20 cm length) and a thermoplastic elastomer outer layer 546 (e.g., Pebax 3533 0.029" ID, 0.0015" wall). The layers 542, 544 and 546 may be thermally reflowed to bond each layer together. A tack bond 516 (e.g., 2 mm length, less than $\frac{1}{3}^{rd}$ circumference) between the outer 512 and inner 514 may be thermally formed to limit longitudinal movement therebetween and transmit longitudinal push forces.

The distal end of the distal outer 512 may be thermally bonded to the proximal waist 52 of the balloon 520. The distal waist 524 of the balloon 520 may be thermally bonded to a distal portion of the inner 514, with approximately 5 mm to 7 mm of the inner 514 extending beyond the distal waist 524 of the balloon 520 to form a distal tip section 518. A radiopaque marker band 530 (e.g., PtIr 90/10, 0.5 mm to 1.0 mm long) may be placed over the inner 514 under the balloon 520 at one or more desired locations such as the proximal, middle or distal aspects of the inflatable portions of the balloon 520. Similarly, a radiopaque marker band 532 may be placed around the distal tip section 518 of the inner 514. The distal marker band 532 may abut a distal terminus of the coil layer 544 of the inner 514 to define an atraumatic distal tip (e.g., 1 mm length) free of the coil layer 544. Optionally, the distal terminus of the coil 544 may be annealed to prevent fraying. Additionally or alternatively, the marker band 532 may be swaged over the distal terminus of the coil 544. As mentioned elsewhere herein, the extended distal tip section 518 acts like the tip of a microcatheter to facilitate advancement over a guidewire around tight turns without causing guidewire back-out for cannulation of the OA, for example.

Over-the-Wire (OTW) Micro Balloon Catheter (MBC)

Figure 20D:
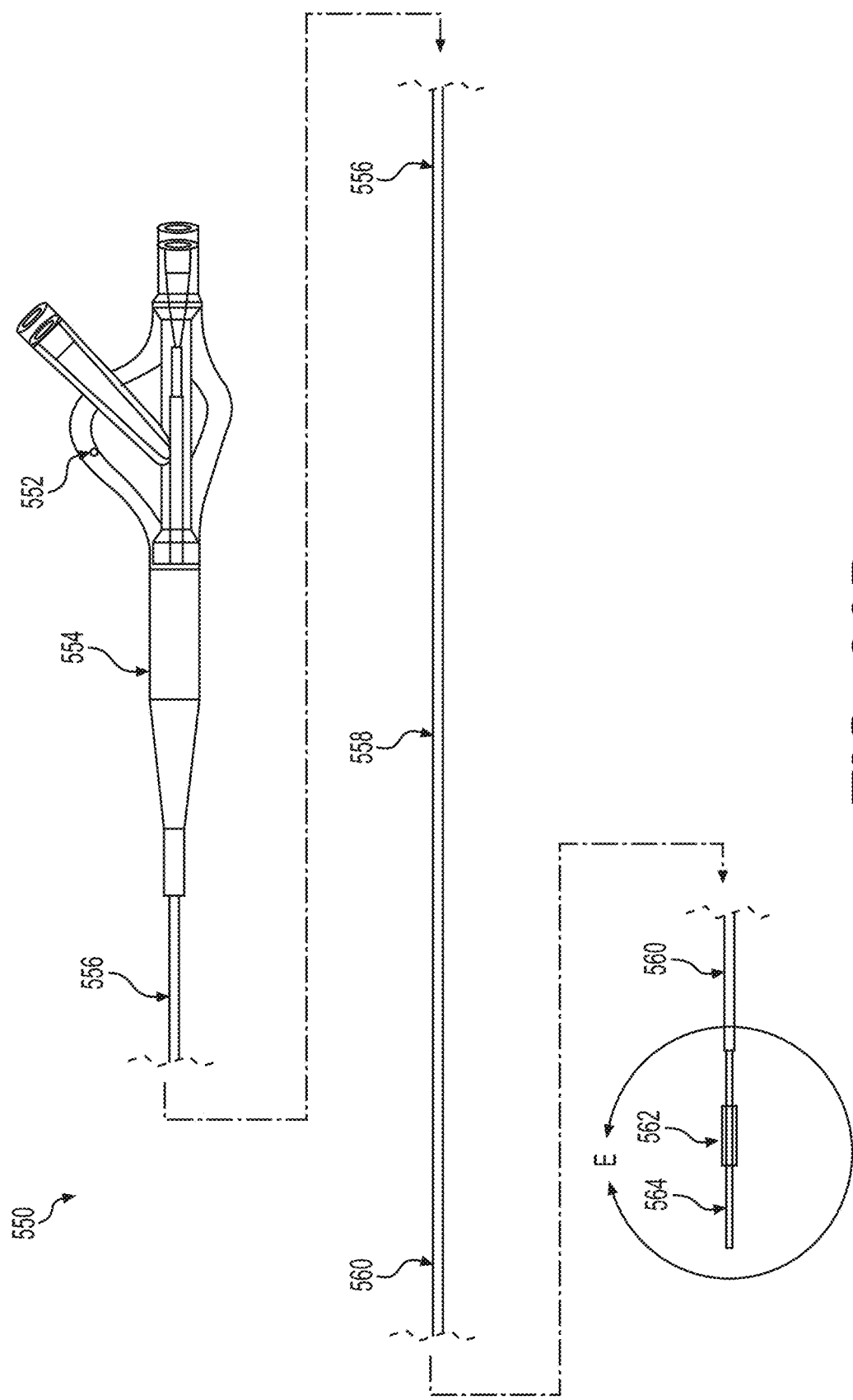
FIGS. 20D-20E are schematic drawings of an alternative over-the-wire micro balloon catheter.
Figure 20E:
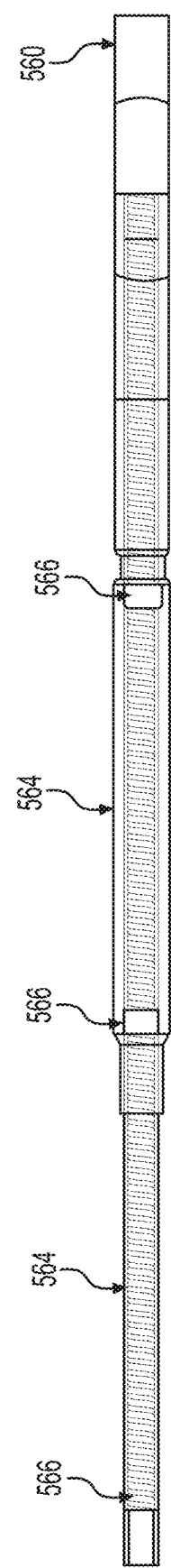

With reference to FIGS. 20D and 20E, an OTW MBC 550 is shown schematically. The OTW MBC 550 is similar to the RX MBC 500 shown in FIG. 20, except that the OTW MBC 550 has a full-length guidewire lumen, thus it is referred to as an over-the-wire (OTW) configuration. This configuration of the OTW MBC 550, in contrast to the rapid exchange configuration of the RX MBC 500, provides a lumen (i.e., guidewire lumen) that extends the full length of the device, thus it may be used not only for advancement over a guidewire, but it may also be used for infusion, aspiration and guidewire exchange once the OTW MBC 550 is disposed intravascularly. Further, due to the microcatheter-like construction of the OTW MBC 550 with a shapeable distal tip, it may be used like the OTW AMC 300 to steer and cannulate a desired target vessel, and because it is torquable, it may be rotated back-and-forth while being advanced to improve its ability to cross tight restrictions. Thus, the OTW MBC 550 serves the dual purposes of a microcatheter (e.g., OTW AMC 300 or RX AMC 400) and a balloon catheter (e.g., RX MBC 500) and thereby eliminates the need to exchange the microcatheter for the balloon catheter once the target vessel (e.g. OA) has been cannulated.

The OTW MBC 550 may include a manifold 552 with inflation and guidewire ports. Extending from the manifold 552, a strain relief 554 may be provided for connection the catheter shaft, starting with proximal shaft section 556. The catheter shaft, including proximal shaft section 556, midshaft section 558 and distal shaft section 560, may comprise an inner disposed in an outer, wherein the inner defines a guidewire lumen and the annular space between the inner and outer defines an inflation lumen for a balloon 562. The distal end of the outer may be connected to a proximal waist of the balloon 562, while the inner extends through the balloon 562 to define a distal tip section 564, with the distal waist of the balloon 562 connected to the inner approximately 8-12 mm proximal of the distal end of the distal tip section 564. The distal tip section 564 may be shaped as described with reference to FIGS. 18A-18F.

The inner may comprise the same or similar construction as the OTW AMC 300, thus providing microcatheter-like performance. The outer may comprise a series of increasingly flexible polymer tubes from proximal to distal. For example, the outer of the proximal shaft section 556 may comprise a relatively stiff polymer (e.g., Pebax 7233, 75 cm length, 0.030-0.034" OD, 0.003 wall thickness), transitioning to the mid-shaft section 558 comprising a relatively flexible polymer (e.g., Pebax 5533, 40 cm length, 0.030-0.034" OD, 0.003 wall thickness), and ending in the distal shaft section 560 comprising an even more flexible polymer (e.g., Pebax 3533, 30 cm length, 0.030-0.034" OD, 0.003 wall thickness). The balloon 562 may comprise the same material as balloon 520 with the proximal waist sized to fit inside the outer of the distal shaft section 560. Radiopaque marker bands 566 may be provided on the inner adjacent the proximal and distal ends of the body of the balloon 564, in addition to the distal aspect of the distal tip section 564.

Alternative Microcatheter

With reference to FIG. 21A, an alternative aiming microcatheter 610 is shown schematically in longitudinal cross-section. The microcatheter 610 may include an elongate shaft 612 having a proximal or main shaft portion 611 and a distal tip section 613a with a bumper tip 613b. A lumen extends through the entire elongated shaft and the hub 614. The overall length of the proximal shaft section 611 may be approximately 150 cm to 160 cm with a 10-15 mm distal section 613a. The proximal shaft section 611 may have an outside diameter of approximately 0.030-0.036 inches to fit within the aiming catheter (described later). The distal shaft section 613a may have an outside diameter of approximately 0.029 inches to fit within the ophthalmic artery. The inside diameter of the elongate shaft 612 may be approximately 0.0125 inches to accommodate a 0.010-inch guidewire, or 0.015-0.016 inches to accommodate a 0.014-inch guidewire. The elongate shaft 612 may have a hydrophilic coating along its distal 70 cm, for example. The elongate shaft 612 may be formed of variable durometer polymers along its length to impart increased flexibility in the distal direction, with embedded metallic braid and coils and a PTFE liner as will be described in more detail.

Figure 22A:
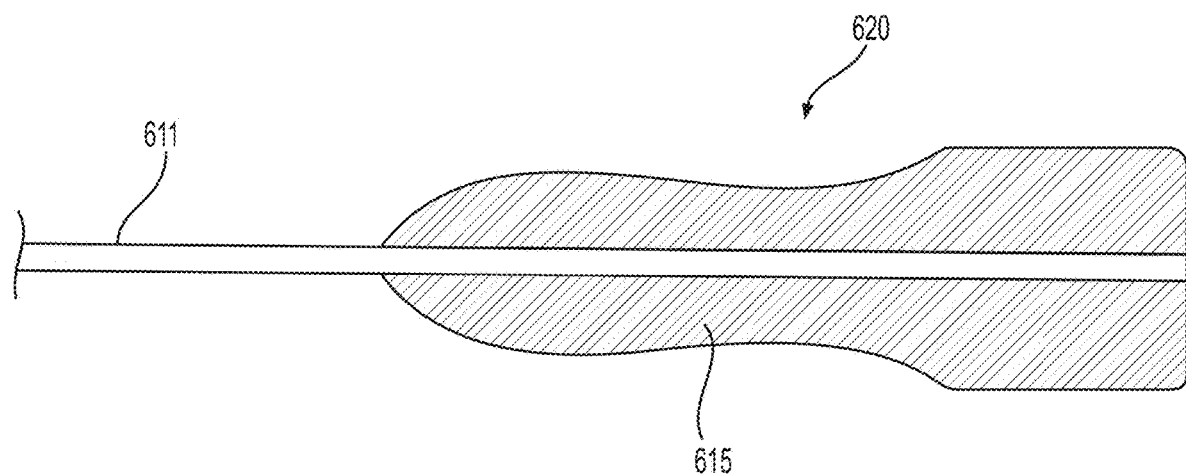
FIG. 22A is a schematic side sectional view of an alternative strain relief for use with the microcatheter shown in FIG. 21A.

The proximal end of the microcatheter 610 may include a hub 614 connected thereto and a strain relief 615. The strain relief 615 may be tapered from the hub 614 to the proximal shaft 611 as shown in FIG. 21A or may be shaped ergonomically as shown in FIG. 22A to facilitate rolling between fingers to change the direction of the curved distal tip.

Figure 22B:
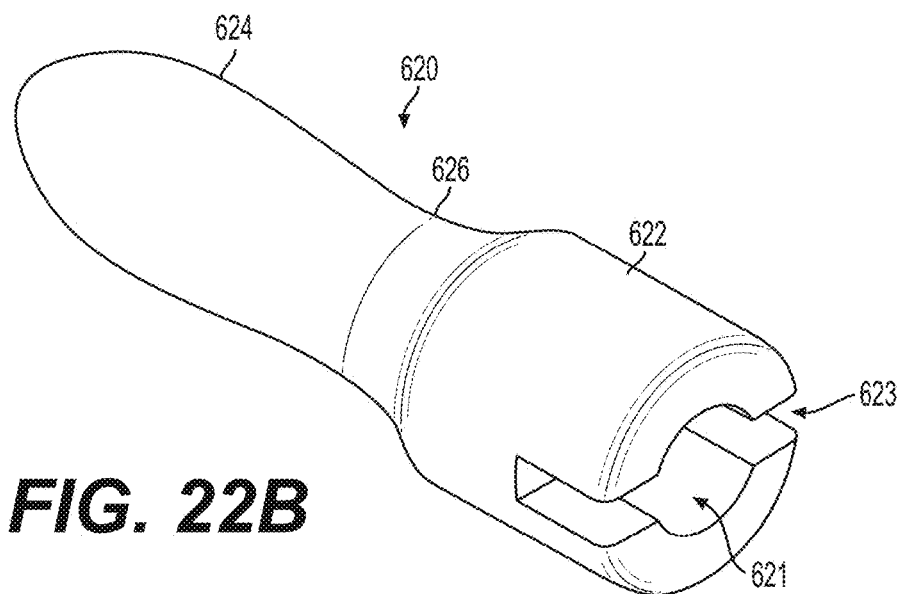
FIG. 22B is a perspective view of a torque handle for use with the microcatheter shown in FIG. 21A.
Figure 22C:
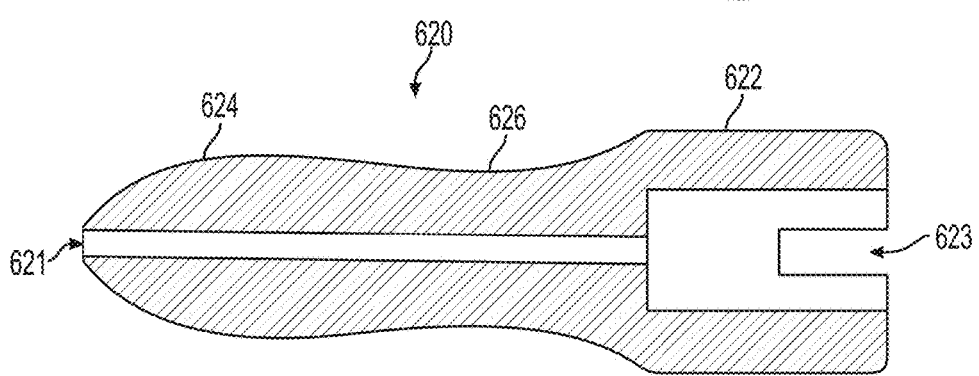
FIG. 22C is a side cross-sectional view of the torque handle shown in FIG. 22B.

A torque handle 620 may be placed over the main shaft 611, the strain relief 615 and/or hub 614 as shown in FIGS. 22B and 22C. The handle 620 may include relatively larger proximal portion 622 and bulbous distal portion 624 to accommodate rolling by first and second fingers, and a recessed portion 626 to accommodate rolling by a thumb, for example. The handle 620 may include a through lumen 621 to accommodate the main shaft 611 of the microcatheter 610, in addition to a proximal slot 623 to accommodate wings of the hub 614, thereby facilitating torque transmission from the fingers/thumb to the hub 614 and then to the microcatheter 610 for purposes of steering a curved tip. This torque handle 620 may engage the hub in other ways, such as snapping into purpose-built features other than the hub wings.

The distal tip 630 of the microcatheter 610 may be straight or may be curve-shaped as shown in FIGS. 23A-23F. The distal tip 630 may be formed to have an anatomically relevant shape such as a 45-degree bend, a 90-degree bend, a 180-degree bend, a shepherd's hook shape, or an abbreviated shepherd's hook shape (where the end does not curve out), for example. Other shapes may be used depending on the specific anatomy being navigated. These shapes maybe pre-formed by the manufacturer or by the physician during use, utilizing heat-set techniques known in the art. As shown in FIG. 23G, for purposes of accessing the ophthalmic artery via the internal carotid artery, particularly when the ophthalmic artery take-off from the internal carotid artery is at a right angle or slightly rearward, the shepherd's hook may have an overall length of approximately 1 cm, with a primary curve 632 height of about 2.5 mm (to approximate one half the inside diameter of the internal carotid artery) and an arc length of about 45 to 90 degrees; a secondary curve 634 height of about 5.0 mm (to approximate the inside diameter of the internal carotid artery) and an arc length of about 60 to 120 degrees; and a tertiary curve 636 height of about 2.0 mm and an arc length of about 15 to 30 degrees such that the distal end cannulates the ophthalmic artery and the outside surface of the secondary curve rests against the opposite wall of the internal carotid artery. The tertiary curve 636 may be eliminated as shown in FIG. 23H in the event the ophthalmic artery take-off is in a more rearward direction.

With reference to FIG. 21B, the proximal or main shaft section 611 is shown schematically in more detail. The inside of the main shaft section 611 may comprise a liner 616a of PTFE having an inside diameter of 0.0165 inches and a wall thickness of 0.0075 inches, for example. The liner 616a may be stretched to 0.0130 inches inside diameter with a wall thickness of 0.0005 inches, for example. The outside surface of the liner may be etched for adhesion of subsequent layers. The main shaft section 611 may further include a braided support layer 617a over the liner 616a comprising spring-temper stainless steel ribbon sized at 0.0005 inches by 0.0025 inches, braided at 175 picks per inch with a one wire under over two pattern or a 1/1 pattern, optionally with a chase wire, for example. The main shaft section 611 may further include, over the braided support layer 617a, a dual layer coil 618a of helical hollow strand 304v stainless steel wire, where the first layer comprises 18 wires, 0.0012-0.0015 diameter wound to 0.022 outside diameter right hand wind, and where the second layer comprises 18 wires, 0.0014 diameter wound to 0.025 inches outside diameter left-hand wind. The dual layer coil 618a may be pressed such that the round wires become oval in cross-section with a height of about 0.0012 inches. The main shaft section 611 may further include, over the dual layer coil 618a, a polymer jacket 619a comprising various durometer polyether block amide tubing. The durometer may vary from 35D proximally to 72D distally. The polymer jacket 619a may be heat-flowed over the underlying layers.

With reference to FIG. 21C, the distal tip section 613a is shown schematically in more detail. The distal tip section 613a may comprise a continuation of the liner 616b of the main shaft section 611. A variable pitch coil 617b of platinum tungsten having an inside diameter of 0.019 inches wound from 0.0025 inch diameter wire may be placed over the liner 616b. A soft polymer jacket 619b (e.g., 80A or 90A durometer thermoplastic polyurethane or 35D durometer polyether block amide) may encapsulate the coil 617b and liner 616b. The PTFE liner 616b may stop short of the distal end, where are the polymer jacket 619b extends to form a soft distal bumper tip 613b. The distal tip section 613a may include three different regions where the coil has a different pitch. In the distal-most region, the coil may have a relatively tight pitch (e.g., no gap) to render the distal end more radiopaque such that the distal end maybe readily identified under x-ray. By using a radiopaque coil rather than a tubular radiopaque band, the distal tip is rendered more flexible. The middle region may have a relatively looser pitch to impart more flexibility and kink resistance. The proximal-most region may have a looser pitch than the distal-most region but a tighter pitch than the middle region to provide for better torque transmission and to transition the stiffness to the proximal or main shaft section that includes braid.

With reference to FIG. 21D, the transition between the proximal or main shaft section 611 and the distal tip 613a is shown schematically in longitudinal cross-section. In this transition region, the liner 616a, 616b extends from the main shaft section to the distal tip section maintaining the same inside diameter. The braid layer 617a and the dual layer coil 618a of the main shaft section 611 end in the middle of the transition region, where the variable pitch coil 617b of the distal tip section 613a begins. The polymer jacket 619a, 619b, like the liner 616a, 616b, extends from the main shaft section 611 to the distal tip section 613a, but tapers in outside diameter as it crosses the junction and eventually forms the distal bumper tip 613b.

Alternative Balloon Catheter

Figure 24A:
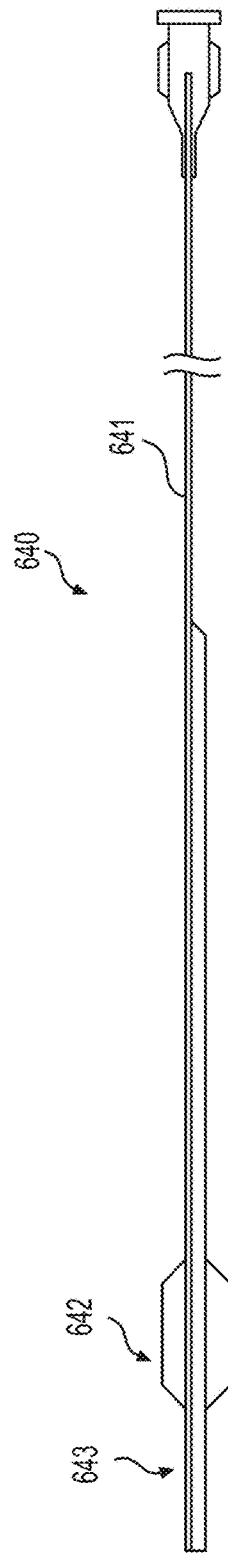
FIG. 24A is a schematic side sectional view of an alternative balloon catheter.

With reference to FIG. 24A, a monorail type over-the-wire balloon dilatation catheter 640 is shown in schematic longitudinal cross-section. The balloon catheter 640 may be used to dilate a restriction in the ophthalmic artery, for example. The balloon catheter 640 may be navigated over a guidewire (not shown) from the femoral artery or radial artery, for example, to the ophthalmic artery. If navigated from the femoral artery, the balloon catheter 640 may have an overall length of approximately 160 cm, for example, and may include a hydrophilic lubricious coating. The balloon 642 may have various diameters such as 1.0 mm, 1.25 mm, 1.5 mm, 1.75 mm or 2.0 mm and various lengths such as 0.5 cm, 1.0 cm or 1.5 cm for purposes of dilating a restriction in the ophthalmic artery.

Figure 24B:
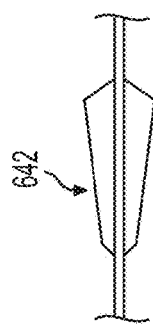
FIG. 24B is a schematic side sectional view of an alternative balloon for use with the balloon catheter shown in FIG. 24A.

As seen in FIG. 24B, the balloon 642 may have a tapered profile to mimic the funnel-shaped geometry of the ophthalmic artery at its origin (ostium) at the internal carotid artery and into the short limb. For example, the balloon 642 may be stepped or tapered from 1.75 or 2.0 mm proximally to 1.25 or 1.5 mm distally, for example. The distal tip 643 may have a length of 1.0 cm-1.5 cm and an outside diameter of approximately 0.015-0.025 inches, for example.

The shaft 641 balloon catheter 640 may include a proximal section comprising a PTFE coated SST hypotube with a proximal hub. The shaft 641 of the balloon catheter 640 may include a mid-section comprising a polymer tube with a tapered core wire extending therein. The proximal ends of the mid-shaft polymer tube and core wire may be boded to the distal end of the hypotube. The distal section of the shaft 641 may comprise two coaxial tubes including an inner to define a guidewire lumen and an outer to define an inflation lumen. The inner extends inside the outer from the distal end of the mid-shaft (proximal guidewire port for monorail design), through the balloon 642 and the distal tip segment (distal guidewire port). The outer extends from the distal end of the mid-shaft to the proximal end of the balloon 642.

The illustrated balloon catheter 640 differs from conventional designs in several aspects, including the distal tip segment 643 that provides a stiffness transition zone between the distal end of the guidewire (when inside the guidewire lumen and extending into the target artery) and the distal waist of the balloon 642 where it is bonded over the inner. When in use, the bare distal portion of the guidewire is much more flexible than the distal waist of the balloon where it is bonded over the inner with the guidewire inside. Because the take-off angle of the ophthalmic artery can be very sharp (right angle or rearward facing), conventional balloon catheter designs tend to cause the guidewire to lose purchase in the ophthalmic artery and slip out as the balloon catheter is advanced over the wire and into the ophthalmic artery. The flexible distal tip segment 643 of the illustrated balloon catheter 640 provides a transition in flexibility: from the bare distal guidewire, to the distal tip segment with the guidewire therein, to the distal balloon waist where it is bonded to the inner with the guidewire therein.

Thus, the balloon catheter 640 has a microcatheter-like supported distal tip segment 643 to facilitate flexibility from the guidewire to the balloon 642, thereby facilitating placement of the tip 643 and balloon 642 into the ophthalmic artery. In order to optimize this flexibility, a coiled structure with variable pitch as described previously maybe employed. Among other advantages, the coil structure provides for flexibility transition, kink resistance, radiopacity and limited stiff sections (that conventional radiopaque marker bands tend to cause). The distal tip segment 643 of the balloon catheter 640 may be shaped as described with reference to the curves 630 of the microcatheter 610. Thus, the balloon catheter 640 may function like a microcatheter, providing steering capability.

In general, the distal tip segment 643 maybe lined with either thin walled polyimide or PTFE, with a polymer skim coat thereover to promote subsequent adhesion of a polymer jacket thereover. The inside diameter maybe 0.013 inches for a 0.010-inch guidewire, tapered down to 0.011 inches near the distal end, for example. Alternatively, the inside diameter maybe 0.017 inches for a 0.014-inch guidewire, tapered down to 0.015 inches near the distal end, for example. The distal outside diameter maybe less than 0.5 mm (0.020 inches) to allow access into the ophthalmic artery, particularly if the ophthalmic artery has a restriction in its ostium.

Figure 24C:
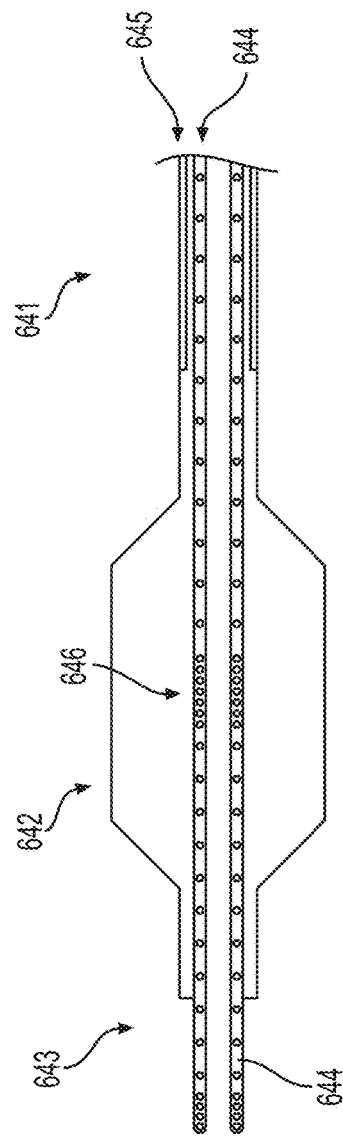
FIG. 24C is a more detailed schematic side sectional view of the balloon assembly of the balloon catheter shown in FIG. 24A.

With reference to FIG. 24C, the balloon 642 and tip 643 assembly is shown in more detail. The balloon 642 and tip 643 assembly may include a coil supported inner subassembly 644 that will be described in more detail. The balloon 642 itself may be available in different sizes as described previously. In this example, the platinum-tungsten coil in the inner 644 may have a variable pitch with a wide pitch proximally to impart flexibility, a narrow pitch in the center 646 to impart radiopacity, a wide pitch distally to impart flexibility, and a narrow pitch at the very distal tip to impart radiopacity. With this arrangement, the center of the balloon as well as the distal end will be clearly visible under x-ray. The outer 645 connected to the proximal and of the balloon 642 may comprise low durometer flexible tubing (e.g., 35D or 55D polyether-block-amide, 80A polyurethane or 90A polyurethane).

Reference to FIGS. 24D and 24E, the distal tip segment 643 is shown in more detail. Again, the distal tip segment 643 may be based on a microcatheter-like design, thus enabling the balloon catheter 640 to be optimized to navigate tortuous anatomy. As shown in FIG. 24D, the distal tip segment may comprise a PTFE liner 647 with a coil 648a and a polymer jacket 649. The coil 648a in the inner 644 may comprise stainless steel flat ribbon wire or round wire wound in a constant or variable pitch to provide flexibility and kink resistance. Radiopaque marker bands 646 comprising short metal tubes of platinum-iridium alloy may be embedded in the inner 644 at desired locations. Alternatively, as shown in FIG. 24E, the coil 648b in the inner 644 may comprise platinum ground wire with variable pitch. A wide pitch coil provides flexibility and kink resistance, and a narrow pitch provides radiopacity where desired. The narrow pitch coil may be used to define radiopaque markers at desired locations such as the center of the balloon and distal end. Alternatively, radiopaque markers may be placed at the proximal and distal ends of the balloon.

Guidewire

With reference to FIGS. 25A and 25B, a guidewire 650 is shown schematically. The guidewire 650 may include a proximal shaft 651 and a distal coil region 652. The guidewire 650 may be used to navigate to the ophthalmic artery from the femoral artery or radial artery. If navigated from the femoral artery, the guidewire 650 may have an overall length of approximately 200-300 cm, for example, and may include a hydrophilic lubricious coating over the distal 100 cm. The proximal portion 651 of the guidewire 650 may have a diameter of 0.014 inches for compatibility with 0.014-inch catheters, or 0.010 inches for compatibility with 0.010-inch catheters. The distal portion 652 of the guidewire 650 may have an outside diameter of 0.008 inches, for example. The proximal portion 651 of the guidewire 650 may comprise a PTFE coated stainless steel wire 656. The distal portion 652 of the guidewire 650 may include coils 654a, 654b having a length of approximately 2.0-6.0 cm over a tapered core wire 653 extension of the proximal wire 656. A polymer jacket 655 may extend over the coiled region 652 and a portion of the proximal shaft 651.

In general, the illustrated guidewire 650 may be optimized for accessing the ophthalmic artery and may be designed to maximize rail support for catheters advanced over the guidewire into the ophthalmic artery, which tends to have a sharp take-off angle from the internal carotid artery. As such, the distal portion 652 of the tapered wire core 653 under the coils 654a, 654b may be much shorter than a typical guidewire. With specific reference to FIG. 25B, the tapered guide wire core 653 may taper from 0.010 inches or 0.014 inches at the proximal end to 0.003 inches over a length of approximately 2.0-6.0 cm such that the distal end of the guidewire 650 that is inserted into the ophthalmic artery would have a wire core diameter of approximately 0.010 inches to 0.014 inches when inserted 2.0-6.0 cm into the ophthalmic artery. In other words, the wire core diameter at the distal end would reach its equivalent diameter at the proximal end after being inserted into the ophthalmic artery 2.0-6.0 cm, corresponding to the short limb thereof. The coiled section 652 may comprise an internal coil 654a and an external coil 654b. The internal coil 654a may comprise 0.001 inch diameter platinum tungsten alloy wire or SST wire with an inside coil diameter corresponding to the wire core (approximately 0.003-0.004 inches) and a length extending 1.0-3.0 cm from the distal end. The external coil 654b may comprise 0.001-0.002 inch diameter platinum tungsten alloy wire with an inside coil diameter of approximately 0.006 inches and a length extending 2.0-6.0 cm from the distal end. The internal coil 654a, external coil 654b and wire core 653 may be welded or soldered at the distal end to form a rounded tip, and the coils 654a, 654b may be similarly bonded at their proximal end to the tapered wire core 653. A polymer jacket 655 having a wall thickness of 0.0005-0.0010 inches may be placed over the coils 654a, 654b, the tapered core wire 653, and a portion of the proximal wire 656 having a length extending approximately 20.0 cm from the distal end.

Aiming Intermediate Catheter

Figure 26A:
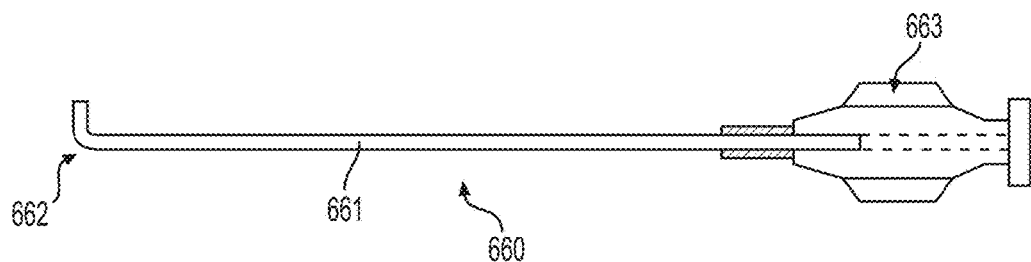
FIG. 26A is a schematic side partially-sectioned view of an aiming intermediate catheter.

With reference to FIG. 26A, a schematic illustration of an aiming intermediate catheter 660 is shown. The aiming intermediate catheter 660 may include a shaft 661, a distal curve 662 and a proximal hub 663. Generally, the inside diameter of the aiming intermediate catheter 660 is configured to accommodate the microcatheter and/or the balloon catheter described previously, with the guidewire described previously disposed therein. An aiming sheath 670 (not shown), as will be described with reference to FIG. 27A, may be slidably disposed over the aiming intermediate catheter 660, and may be advanced or retracted to cover the distal curve 662 of the aiming intermediate catheter 660 to effectively change the shape of the curve 662. The curve 662 may take any of the shapes described with reference to FIGS. 23A-23H, for example. The aiming intermediate catheter 660 may be intended to facilitate navigation to the internal carotid artery with its distal opening pointing to the ophthalmic artery such that devices inserted into and through the aiming intermediate catheter 660 are positioned to cannulate the ophthalmic artery. In addition, the aiming intermediate catheter 660 may be intended to facilitate safe navigation of the aortic arch, selective access of the great vessels (e.g., common carotid) from a femoral or radial approach, selective cannulation of the internal carotid at the carotid bifurcation, or selective cannulation other vessels in the brain.

As seen in FIG. 26A, the aiming intermediate catheter 660 may have an overall length of approximately 130 to 145 cm to facilitate navigation from the femoral artery to the ophthalmic artery. The tubular shaft 661 of the aiming intermediate catheter 660 may have an outside diameter of approximately 0.049 inches to 0.052 inches and an inside diameter of approximately 0.038 inches. A catheter hub 663 and a strain relief may be adhesively secured to the proximal end of the catheter shaft 661. A hydrophilic coating may be applied to the working length of the catheter shaft 661.

Figure 26B:
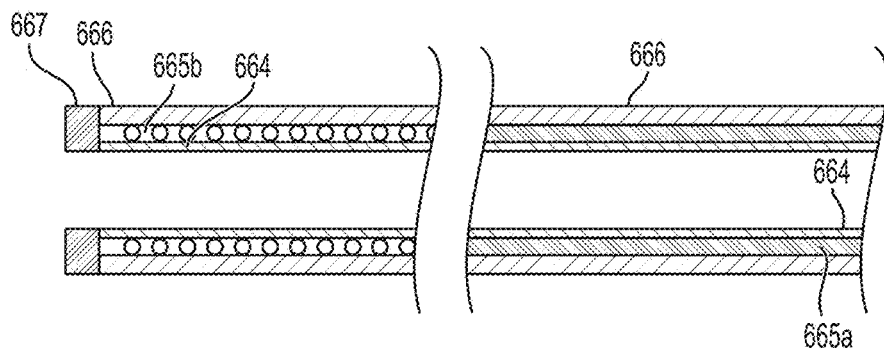
FIG. 26B is a more detailed schematic side sectional view of the distal portion of the aiming intermediate catheter shown in FIG. 26A.

As seen in FIG. 26B, which shows a longitudinal cross-section of the shaft 661, the proximal and of the catheter shaft 661 may comprise a 0.00075 inch thick PTFE liner 664 over which a stainless steel braided 665a is secured with a polymer thermoplastic jacket 666 surrounding the braid 665a. The braid 665a may comprise a diamond pattern with 80-125 picks per inch and a length of 120-135 cm, using ultra-spring temper or HYTEN 304V stainless steel wire. The polymer jacket 666 may comprise multiple sections of progressively flexible polymer such as 72D polyether-block-amide, 55D polyether-block-amide, 90AE polyurethane and 80AE polyurethane (from proximal to distal). The distal 3-6 cm of the catheter shaft 661 corresponding to the curve 662 may comprise a continuation of the PTFE liner 664, over which a pattern-cut, NiTi super-elastic alloy hypotube 665b may be secured. A continuation of the polymer thermoplastic jacket 666 of the proximal shaft may continue over the distal shaft and extend slightly beyond the distal end of the PTFE liner 664 and pattern-cut NiTi hypotube 665b to form a soft polymer tip 667. The distal end of the NiTi hypotube 665b may be plated with radiopaque material or a radiopaque marker band may be disposed thereon to facilitate visualization under x-ray.

Figure 26C:
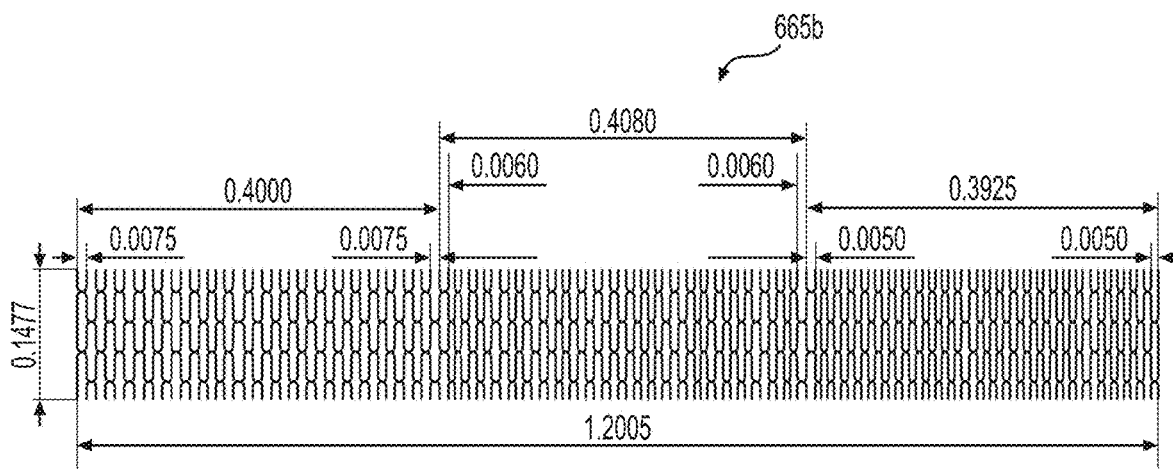
FIG. 26C is a detailed view of the cut pattern used for the NiTi tube in the aiming intermediate catheter shown in FIG. 26A.

An example of a cut pattern of the NiTi super-elastic alloy hypotube 665b is shown in FIG. 26C, where all dimensions are shown in inches. As illustrated, the proximal end is at right and the distal end is at left, and the hypotube is shown splayed out flat rather than tubular. The wall thickness of the hypotube may be 0.002-0.003 inches and the strut width may be 0.0025 inches. The pattern may have 3 zones that are progressively more flexible from proximal to distal by reducing the amount of material proximal to distal (e.g., increasing size of cuts, using a more sparse cut pattern, or using a different cut pattern in each section). In this example, the graduated flexibility is provided by increasing the longitudinal spacing between struts from 0.005, to 0.006 to 0.0075 inches.

The shape of the distal curve 662 of the aiming catheter may be imparted by pre-forming the NiTi hypotube before assembly, and then by heat setting the final assembly such that the polymer jacket 666 and PTFE liner 664 assume the same shape as the NiTi hypotube 665b. I.e., Using the same disposition or shape in which the NiTi was originally formed to maximize shape retention. The super-elastic NiTi hypotube 665b may be made using the following process. The desired pattern may be laser cut into the NiTi hypotube and subsequently bead blasted to remove slag or dross from the laser cutting. The cut NiTi hypotube may be placed in a forming fixture have the desired shape. The forming fixture may be a fixture that retains that outer diameter of the hypotube, a mandrel inside the hypotube, or a combination of the two. While in the forming fixture, the cut NiTi hypotube may be annealed at 300 C for 3 minutes in heated oven or salt bath, then heat set for 6-10 minutes at 500-510 C. The NiTi hypotube is then removed from heat source and immediately quenched in room temperature water. The heat set laser cut NiTi hypotube may be electropolished or chemically etched to remove surface tarnish or discoloration due to heat exposure.

Aiming Catheter Sheath

Figure 27A:
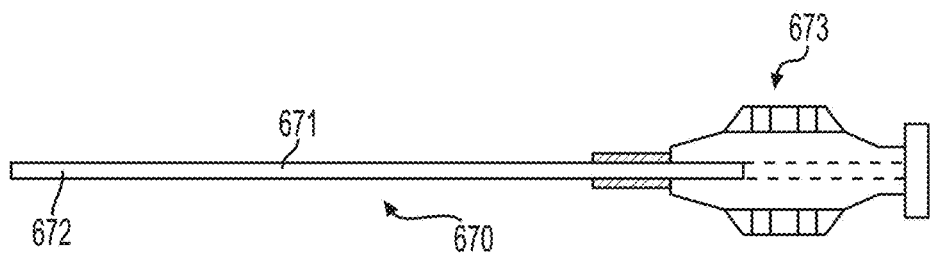
FIG. 27A is a schematic side partially-sectioned view of an aiming catheter sheath.

With reference to FIG. 27A, an aiming catheter sheath 670 is shown schematically. The aiming catheter sheath 670 may be designed to be placed over the aiming intermediate catheter 660 and may be advanced over the curved portion 662 to straighten the curve to varying degrees to obtain different angles of curvature. The aiming catheter sheath 670 may include an elongated shaft 671, 672 having a length of approximately 110 to 125 centimeters, with a proximal hub 673 and strain relief. The outside diameter of the shaft 671, 672 may be 0.068 inches to 0.072 inches, and the inside diameter may be 0.058 inches to 0.059 inches.

Figure 27B:
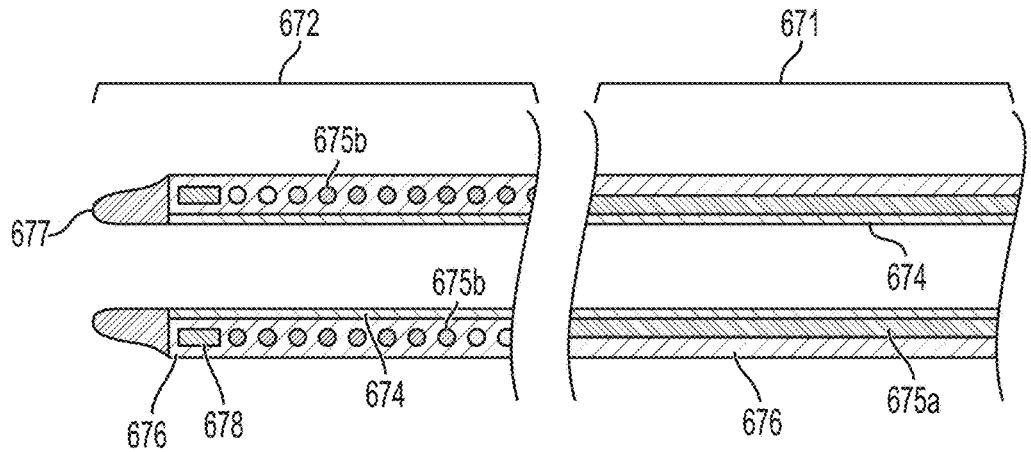
FIG. 27B is a more detailed schematic side sectional view of the proximal and distal shaft portions of the aiming catheter sheath shown in FIG. 27A.

As seen in FIG. 27B which shows a longitudinal cross-section of the proximal shaft 671 and distal shaft 672, the proximal shaft 671 may include a 0.00075 inch thick PTFE liner 674 over which a braid 675a is disposed, covered by a polymer jacket 676. The braid 675a may comprise a diamond pattern with 80-125 picks per inch and a length of 108-114 cm, using ultra-spring temper or HYTEN 304V stainless steel wire. The polymer jacket 676 may comprise multiple sections of progressive flexibility such as 72D polyether-block-amide, 55D polyether-block-amide, 90AE polyurethane and 80AE polyurethane (from proximal to distal). The distal section 672 of the shaft comprising the distal 3.0 cm, for example, may include a continuation of the PTFE liner 674 over which a stainless-steel coil 675b of round or flat wire may be disposed, covered by a continuation of the polymer jacket 676. The coil may comprise 0.002 inch by 0.005 inch flat 304V stainless steel ribbon with variable pitch sections including 0.0075 inch pitch for 1.25-2.5 cm proximal section, 0.010 inch pitch; 5.0-7.5 cm for midsection and 0.012 inch pitch for 1.25-2.5 cm distal section. A radiopaque marker band 678 may be placed over the liner 674 and embedded in the polymer jacket 676 just distal of the coil 675b. The polymer jacket 676 may extend beyond the PTFE liner 674, the coil 675b and the marker band 678 to form a soft distal tip 677.

Figure 27C:
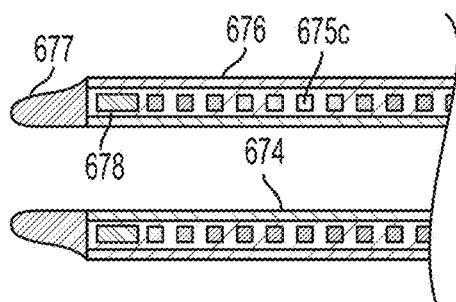
FIG. 27C is a schematic side sectional view of an alternative distal shaft portion of the aiming catheter sheath shown in FIG. 27A.
Figure 27D:
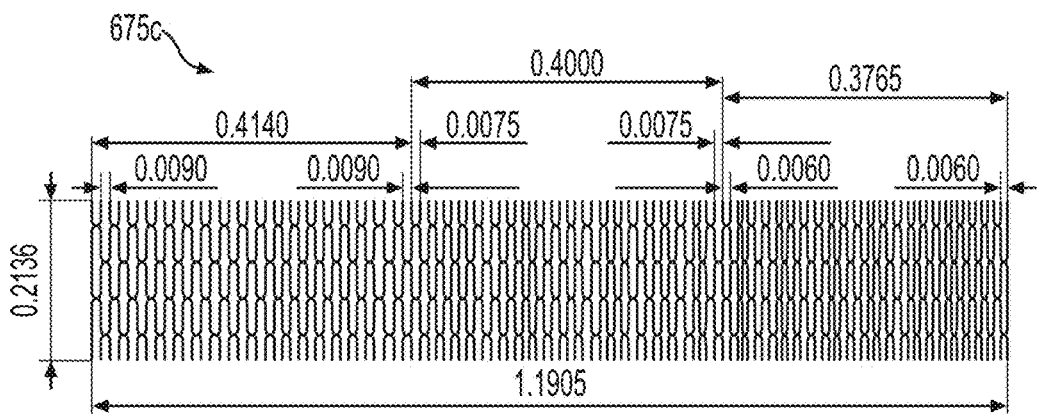
FIG. 27D is a detailed view of the cut pattern used for the NiTi tube in the aiming catheter sheath shown in FIG. 27A.

An alternative distal section design is shown in longitudinal cross-section in FIG. 27C. In this alternative design, the wire coil is replaced with a laser cut NiTi hypotube 675c similar to the same used in the aiming intermediate catheter 660. An example of a cut pattern for use in this alternative design is shown in FIG. 27D. As illustrated, the proximal end is at right and the distal end is at left, and the hypotube is shown splayed out flat rather than tubular. The wall thickness of the hypotube may be 0.003 inches and the strut width may be 0.0025 inches. The pattern may have 3 zones that are progressively more flexible from proximal to distal. In this example, the graduated flexibility is provided by increasing the longitudinal spacing between struts from 0.006, to 0.0075 to 0.009 inches.

Aiming Intermediate Catheter and Sheath System

Figure 28A:
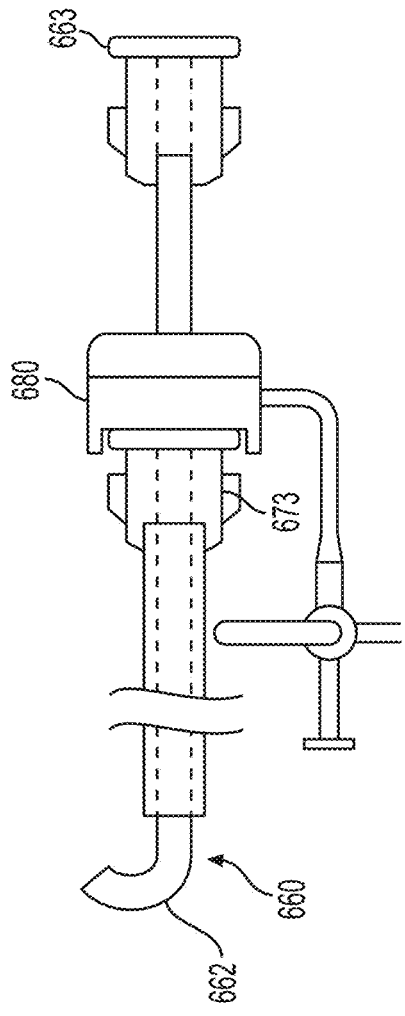
FIGS. 28A and 28B are schematic illustrations of how the aiming catheter and aiming catheter sheath may be used together.
Figure 28B:
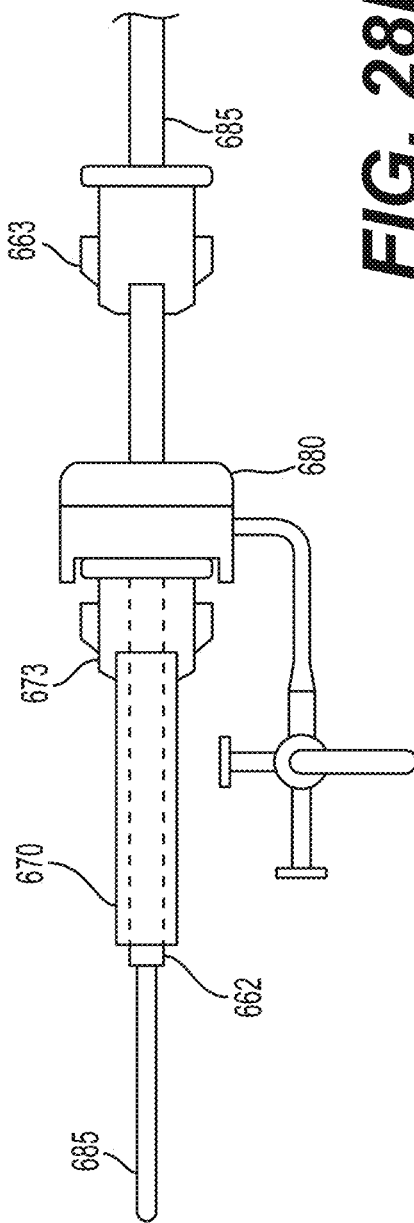

FIGS. 28A and 28B schematically illustrate how the aiming intermediate catheter 660 and the aiming catheter sheath 670 may be used together. As shown in FIG. 28A, the aiming intermediate catheter 660 is disposed in the aiming catheter sheath 670 through a hemostasis valve 680 connected to the proximal hub 673 of the sheath 670. As shown, the sheath 670 may be retracted and or the aiming intermediate catheter 660 may be advanced such that the distal curved portion 662 of the aiming intermediate catheter 660 is disposed distal of the sheath 670 and where the curved portion 662 assumes its preset curvature. The aiming intermediate catheter 660 may be retracted or the sheath 670 may be advanced to adjust the degree of curvature and to point the distal opening of the aiming intermediate catheter 660 in the desired direction such as pointing toward the ophthalmic artery while disposed in the internal carotid artery. The degree of curvature may also be adjusted for purposes of, for example, safe navigation of the aortic arch, selective access of the great vessels (e.g., common carotid) from a femoral or radial approach, selective cannulation of the internal carotid at the carotid bifurcation, or selective cannulation other vessels in the brain. As shown in FIG. 28B, for purposes of advancing the aiming intermediate catheter 660 to the desired location, the aiming intermediate catheter 660, while retracted in the sheath, may be advanced over a 0.035 inch guidewire 685 as a system, for example, through a separate guide sheath or femoral sheath.

Aiming Intermediate Catheter Handle

Figure 29A:
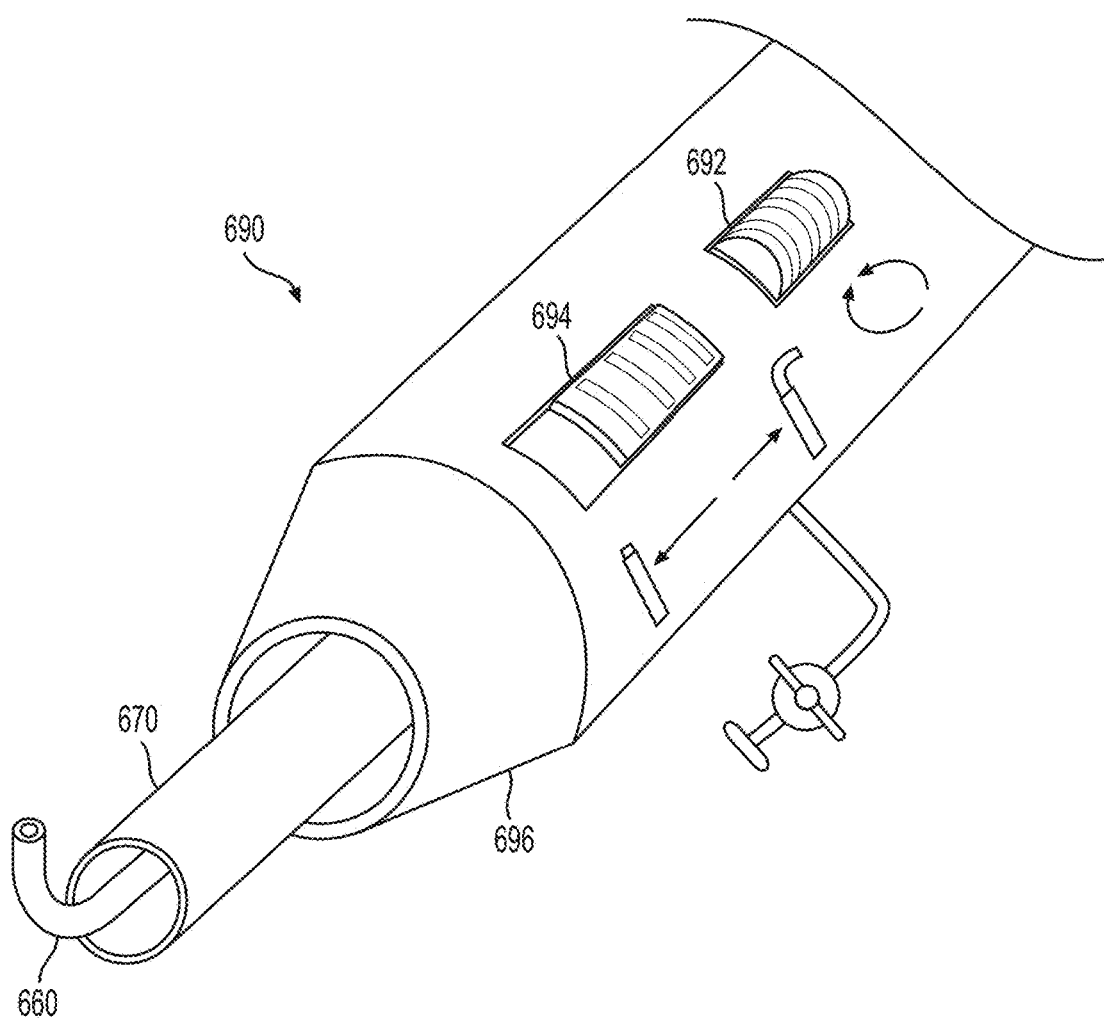
FIGS. 29A and 29B are schematic illustrations of a handle system for use with the aiming catheter and aiming catheter sheath shown in FIGS. 26A and 27A, respectively.
Figure 29B:
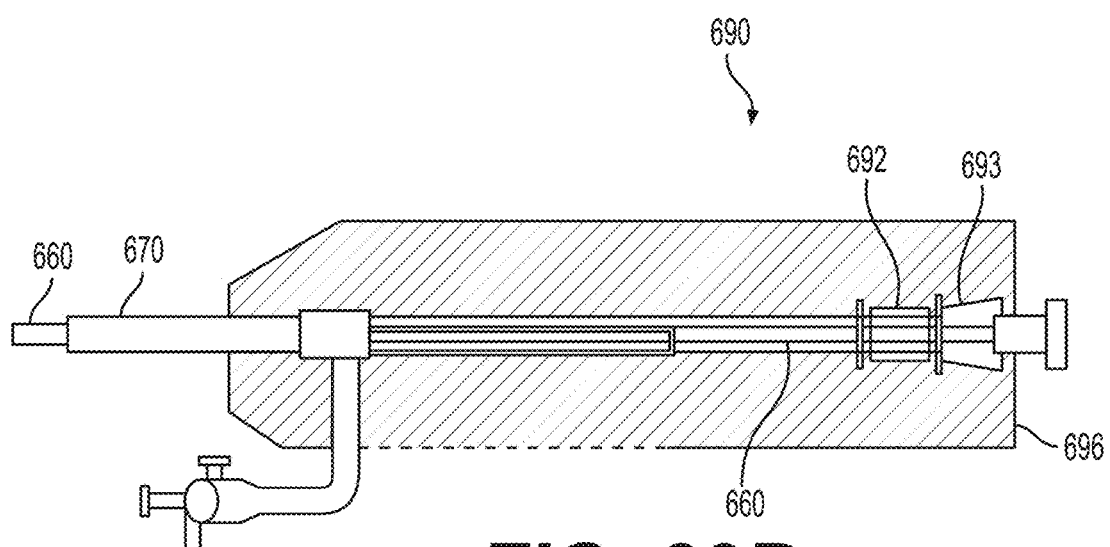

To enable precise axial movement of the aiming intermediate catheter 660 relative to the aiming catheter sheath 670, and thereby enable precise adjustment and locking of the curvature 662, an aiming system handle 690 may be used as shown in FIGS. 29A and 29B. With specific reference to FIG. 29A, the handle 690 may include a rotational knob 692 operably coupled to the aiming intermediate catheter 660 in order to rotate the aiming intermediate catheter 660 and thereby steer the distal curved section 662. The handle 690 may also include a slider (or slider/rotational knob combination) 694 to control axial movement of the aiming catheter sheath 670 relative to the aiming intermediate catheter 660 in order to adjust the degree of curvature of the curved portion 662. The inner workings of the handle 690 may be better appreciated with reference to FIG. 29B. The handle may include a body portion 696 that is fixed axially to the aiming intermediate catheter 660 but allows rotation of the aiming intermediate catheter 660 through the use of a rotator 693. The rotational knob 692 is fixed to the aiming intermediate catheter 660 such that rotation of the knob 692 causes rotation of the aiming intermediate catheter 660 relative to the body portion 696 and sheath 670. The slider 694 is axially movable relative to the handle body 696 but is fixed to the sheath 670 such that pushing or pulling the slider 694 relative to the handle body 696 causes the sheath 670 to be advanced or retracted, respectively, relative to the aiming intermediate catheter 660 such that the curved portion 662 of the aiming intermediate catheter 660 is selectively covered or exposed, respectively. A corollary arrangement may be used alternatively where pushing or pulling the slider 694 relative to the handle body 696 causes the aiming intermediate catheter 660 to be advanced or retracted, respectively, relative to the sheath 670 which remains fixed.

Guide Sheath

Figure 30:
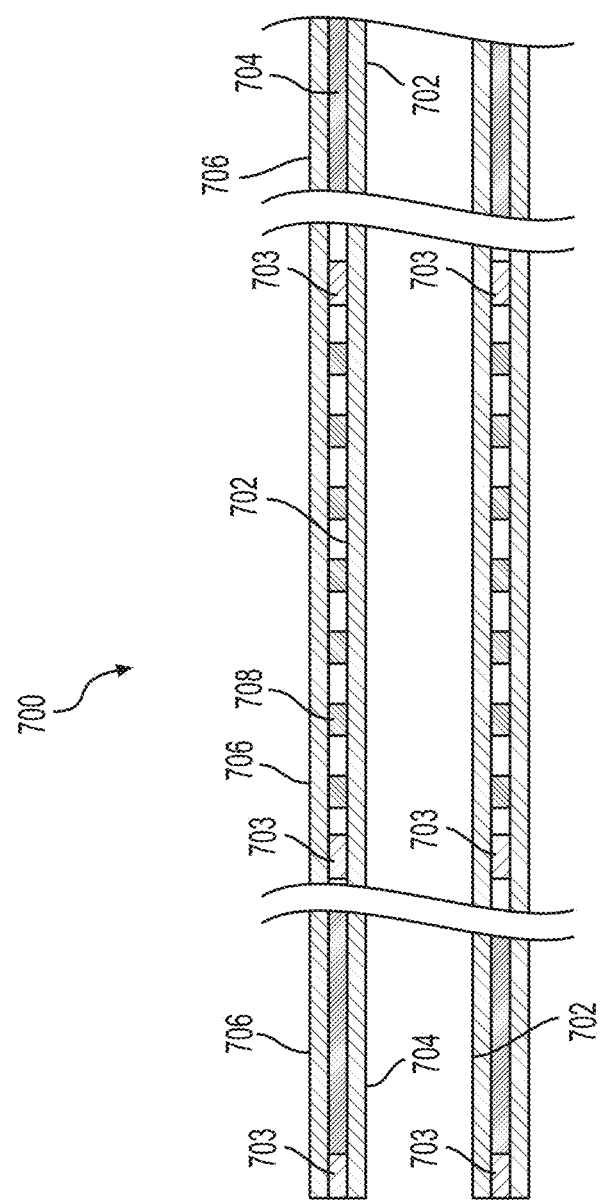
FIG. 30 is a schematic side sectional view of a guide sheath.

FIG. 30 shows a schematic longitudinal cross-section of a guide sheath 700 that includes a distal section (S1) that is very flexible, a middle section (S2) that has extra kink resistance, and a proximal section (S3) that is very pushable. The middle section with extra kink resistance may be particularly useful when navigating from the aorta, through the aortic arch, into the common carotid artery. This zone tends to be very tortuous and can cause conventional guide sheaths to become oval (rather than round) or kink. If the guide sheath becomes oval or kinks, it tends to seize or block devices inserted therein. To prevent the shaft from becoming oval or kinking, the middle section may include a pattern cut NiTi hypotube 708 disposed between a liner 702 and a polymer jacket 706. The proximal and distal sections may include a braid 704 disposed between the liner 702 and the polymer jacket 706. The liner 702 may comprise PTFE tubing with a wall thickness of 0.00075 inches. The polymer jacket 706 may be progressively flexible from proximal to distal, such as 72D nylon 12 on the proximal section, 72D-55D polyether-block-amide on the middle section, and 80AE-90AE polyurethane on the distal section. The proximal section may have a length of approximately 20-40 cm, the middle section may have a length of approximately 30-40 cm, and the distal section may have a length of approximately 20-30 cm. The middle section, when the guide sheath 700 is placed in-vivo, may be positioned in the aortic arch. To facilitate x-ray imaging to confirm that the middle section is in the aortic arch, radiopaque marker bands 703 may be embedded at both ends of the middle section. A marker band 703 may also be embedded at the distal end of the catheter.

Alternative Example Method

Figure 31A:
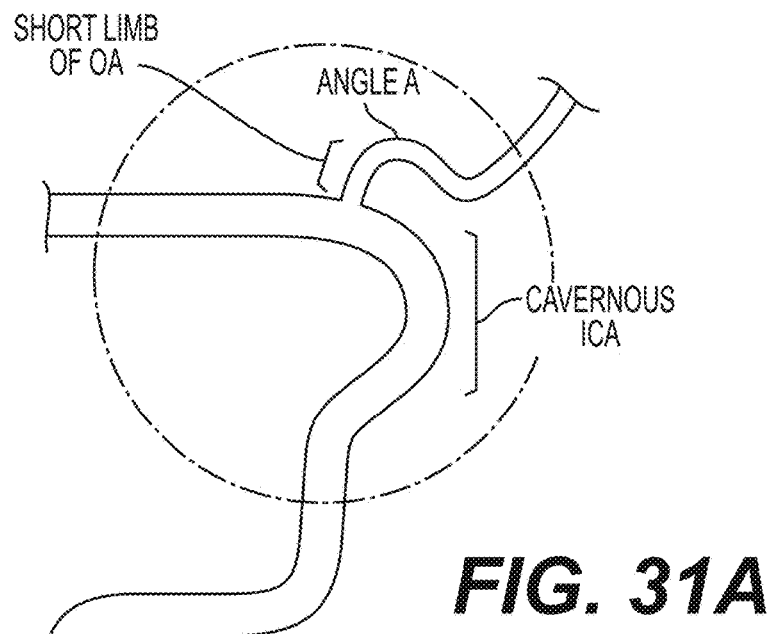
FIGS. 31A and 31B schematically illustrate how the guidewire, microcatheter, aiming catheter, aiming catheter sheath and guide sheath may be used together.
Figure 31B:
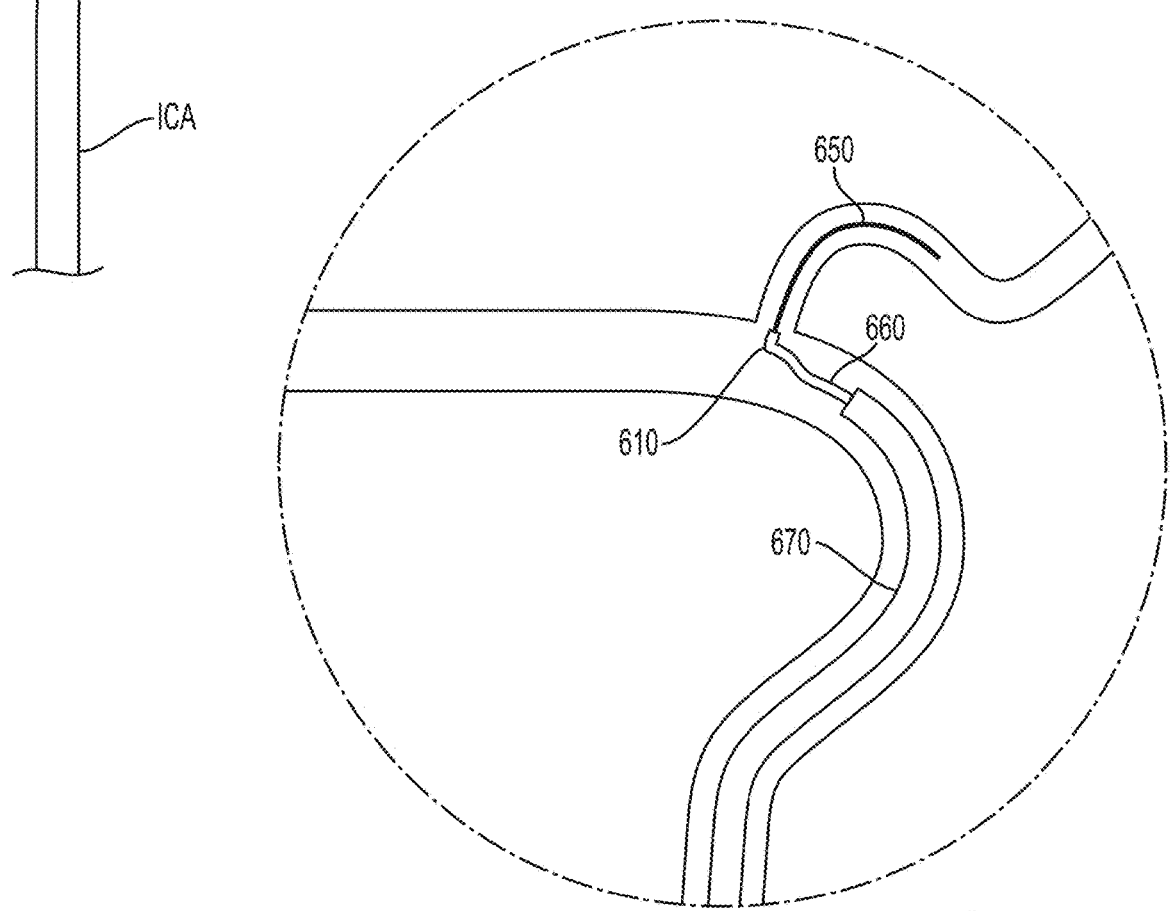

FIGS. 31A and 31B schematically illustrate use of some of the devices described herein with reference to the internal carotid artery (ICA) and the ophthalmic artery (OA). FIG. 31A shows the ICA, cavernous sinus of the ICA, and the OA branching off the ICA at a sharp right or backward facing angle. FIG. 31B shows the OA in more detail, where the OA originates as a funnel-shaped ostium as it branches off the ICA and extends to angle A to define a short limb, which may be the target for therapy. Each of the devices described herein may be configured to work cooperatively to reach the OA from a femoral access approach. The lengths may be adjusted to accommodate different access approaches such as a radial access approach, a cervical access approach, or an oculofacial artery approach, for example. The guide sheath 700 (not shown) may be configured to accommodate the aiming intermediate catheter 660 and aiming catheter sheath 670, which in turn may be configured accommodate the microcatheter 610 or balloon catheter 640 (not shown), which in turn may be configured to accommodate the guidewire 610.

By way of example, the guide sheath 700 (not shown) may be used to provide access from the femoral artery, through the aorta and aortic arch, to the carotid bifurcation over a 0.035 inch guidewire. The aiming intermediate catheter 660 and aiming catheter sheath 670 may be inserted through the guide sheath 700 over a 0.035 inch guide wire, and the curvature 662 of the aiming intermediate catheter 660 may be adjusted (as described previously) to aim its distal opening toward the ostium of the OA. The 0.035 inch guidewire may be removed, and the 0.010 or 0.014 inch guidewire 650 may be inserted into the aiming intermediate catheter 660, either alone or with the microcatheter 610 or the balloon catheter 640 loaded on the guidewire 650. With the aiming intermediate catheter 660 pointed to toward the OA ostium, the guidewire 650 may be inserted into the OA, optionally using a shaped tip of the microcatheter 610 to make fine steering adjustments to the guidewire 650 until it cannulates the OA. Once the guidewire 650 is disposed in the OA, beyond angle A for example, the microcatheter 610 may be inserted into the OA for delivery of drugs or contrast media, for example. Similarly, the balloon catheter 640 may be inserted over the guidewire 650 into the OA to dilate a restriction therein.

Alternative Access Sites

Figure 32A:
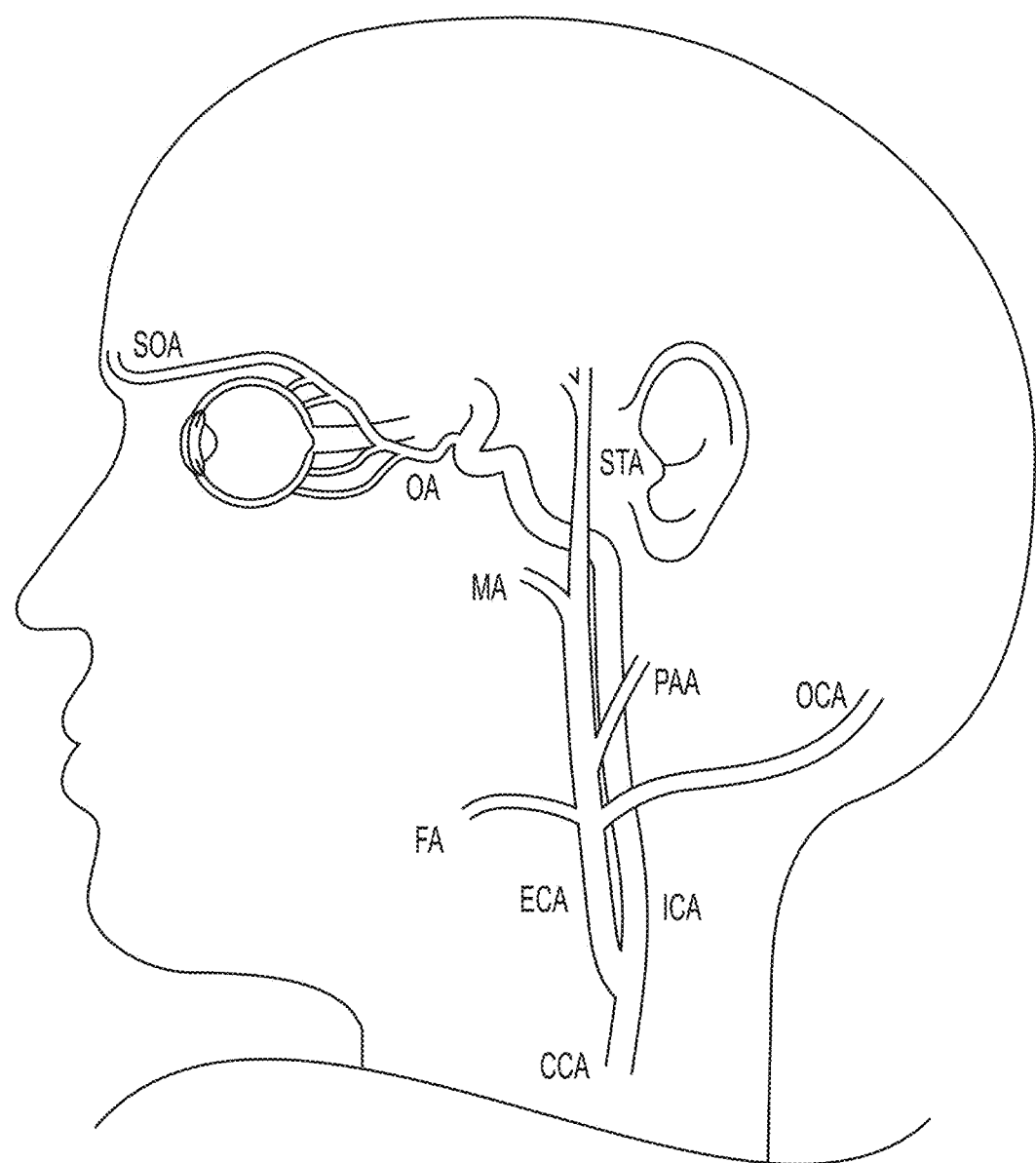
FIGS. 32A-32F schematically illustrate various alternative access sites and associated access and closure accessories.

Each of the devices described herein may be configured to work cooperatively to reach the OA from an access site in the femoral artery. The diameters and lengths may be adjusted to accommodate different access sites such as the radial, brachial, cervical or common carotid arteries. Less known or heretofore unknown access sites may also be used, such as access from the supra-orbital, supra-trochlear, superficial temporal or occipital arteries. With reference to FIG. 32A, some of these less known access sites and related arterial anatomy are shown schematically: common carotid artery (CCA), external carotid artery (ECA), occipital artery (OcA), facial artery (FA), posterior auricular artery (PAA), maxillary artery (MA), superficial temporal artery (STA), supra-orbital artery (SOA), dorsal nasal artery and ophthalmic artery (OA). The supra-trochlear artery (STrA, not shown) is similarly situated to the SOA and may be collectively referred to as oculofacial arteries (a.k.a. frontal or facial arteries).

Figure 32B:
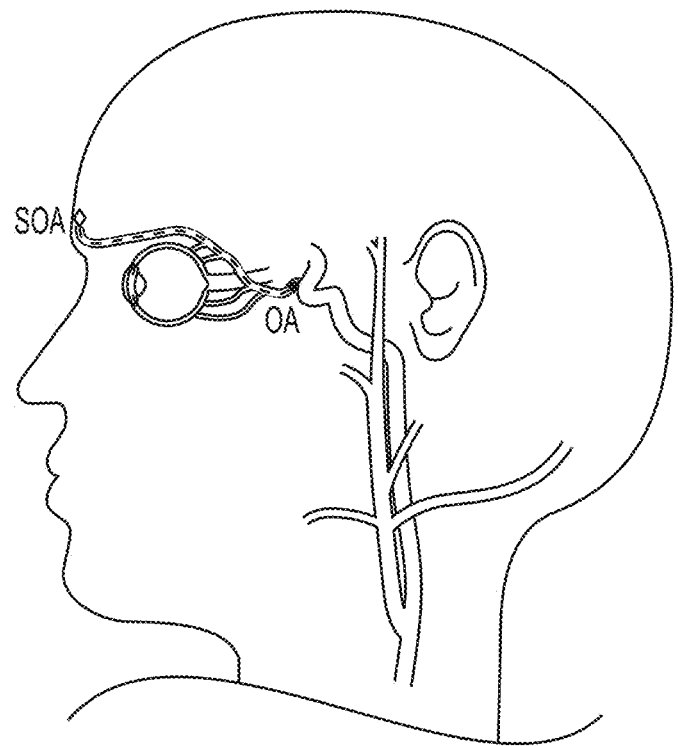
Figure 32C:
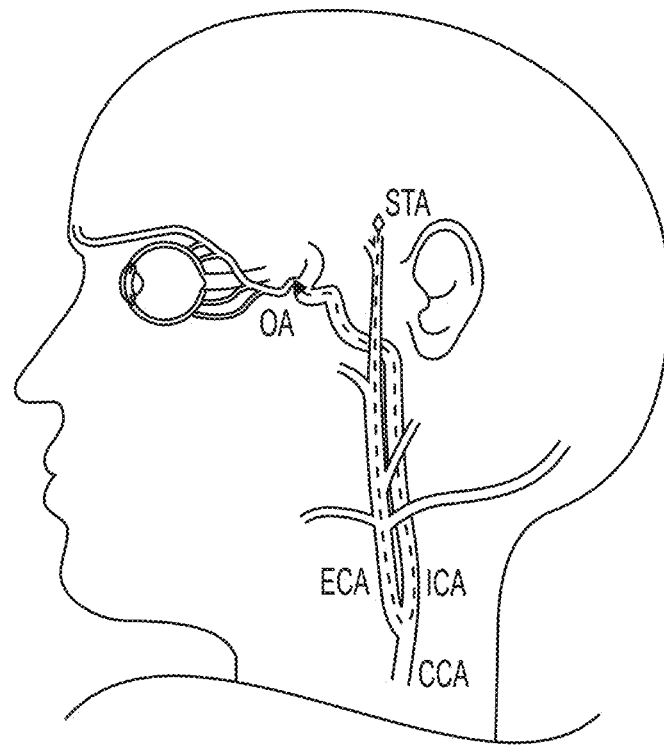
Figure 32D:
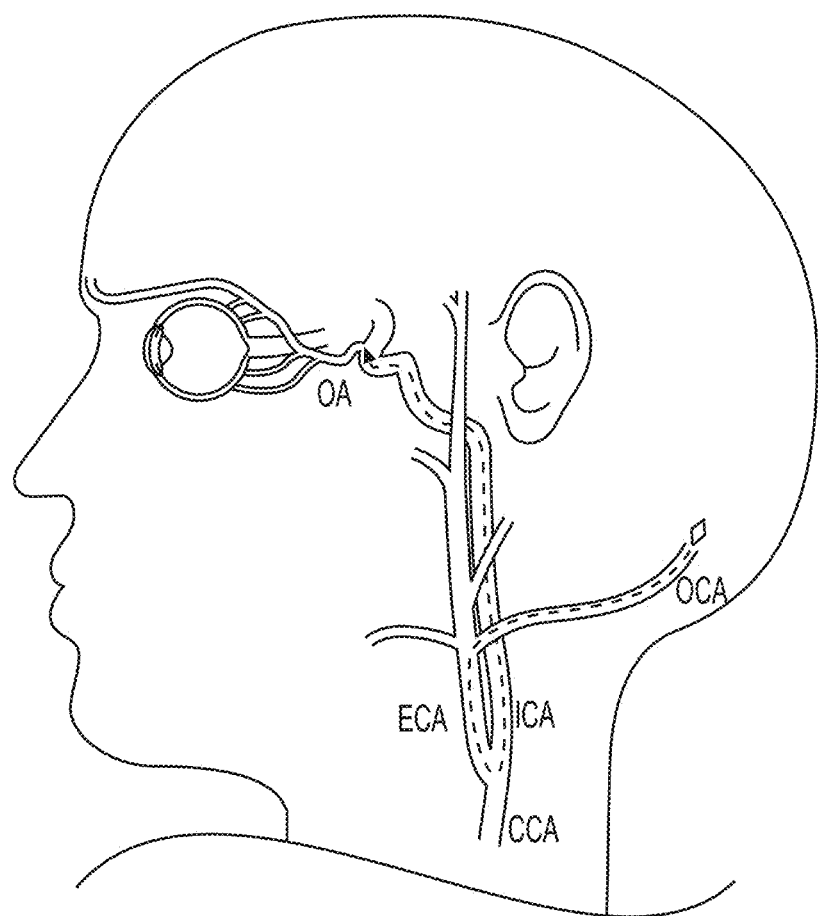

With reference to FIG. 32B, one of the oculofacial arteries such as the STrA or SOA may be accessed adjacent the eyebrow to navigate devices in a retrograde direction directly to the OA as shown by the dotted line. With reference to FIG. 32C, the STA may be accessed adjacent the ear to navigate devices in a retrograde direction down the ECA, around the carotid bifurcation at the CCA, then in an antegrade direction up the ICA to the OA as shown by the dotted line. With reference to FIG. 32D, the OcA may be accessed adjacent the occipital bone to navigate devices in a retrograde direction in the OcA, down the ECA, around the carotid bifurcation at the CCA, then in an antegrade direction up the ICA to the OA as shown by the dotted line. Each of these access sites is relatively superficial allowing identification using digital palpation or transdermal doppler ultrasound, percutaneous access without the need for a cut-down, and relatively simple closure by manual compression or by a compression device wrapped around the head.

Figure 32E:
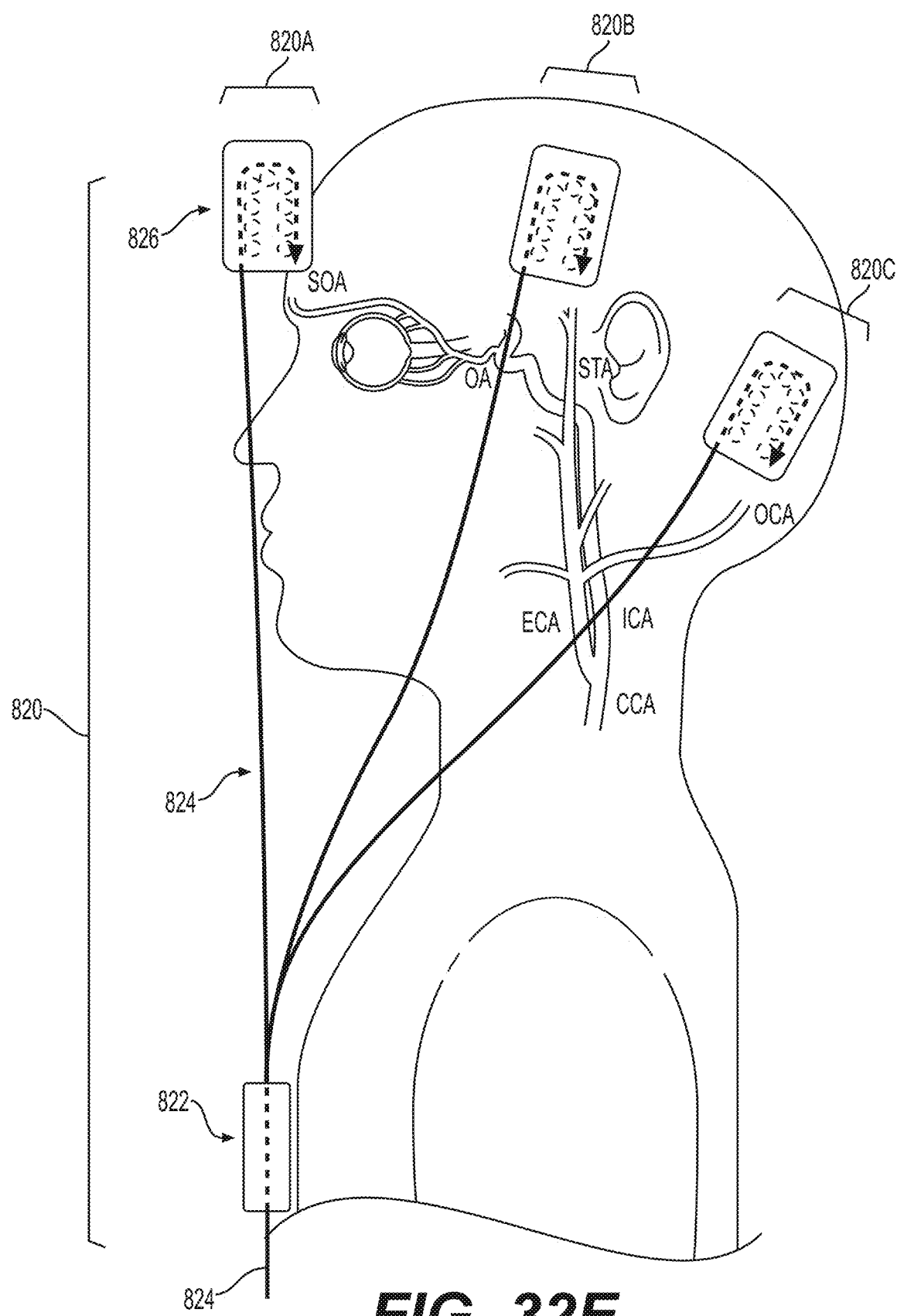

With each of the access sites in the head, it may be desirable to position the treating physician's hands outside the field of radiation used to image the cranial vasculature. As such, and with reference to FIG. 32E, the physician's hands may be placed below the neck, resting on the patient's chest, for example. However, because the vascular access direction is inferior, it may be helpful to employ a reversing system 820 that allows the physician to advance devices in a superior direction and redirect the devices in an inferior direction. The reversing system 820 may be positioned for accessing the SOA or STrA as shown by system 820A, the STA as shown by system 820B or the OcA as shown by system 820C. The reversing system 820 may include a proximal manifold 822, a common conduit 824 and a reversing manifold 826. The proximal manifold 822 may be secured below the patient's neck proximate the chest. The common conduit 824 may comprise a 10F braid reinforced tube, for example. The reversing manifold 826 may include a U-turn conduit, optionally with means to minimize friction such as roller bearings. The reversing manifold 826 may be secured proximate the access site, using a head band, for example. The reversing manifold 826 may incorporate micro motors with elements that could feed or torque a catheter to mimic the physician's hands at the proximal manifold 822.

Figure 32F:
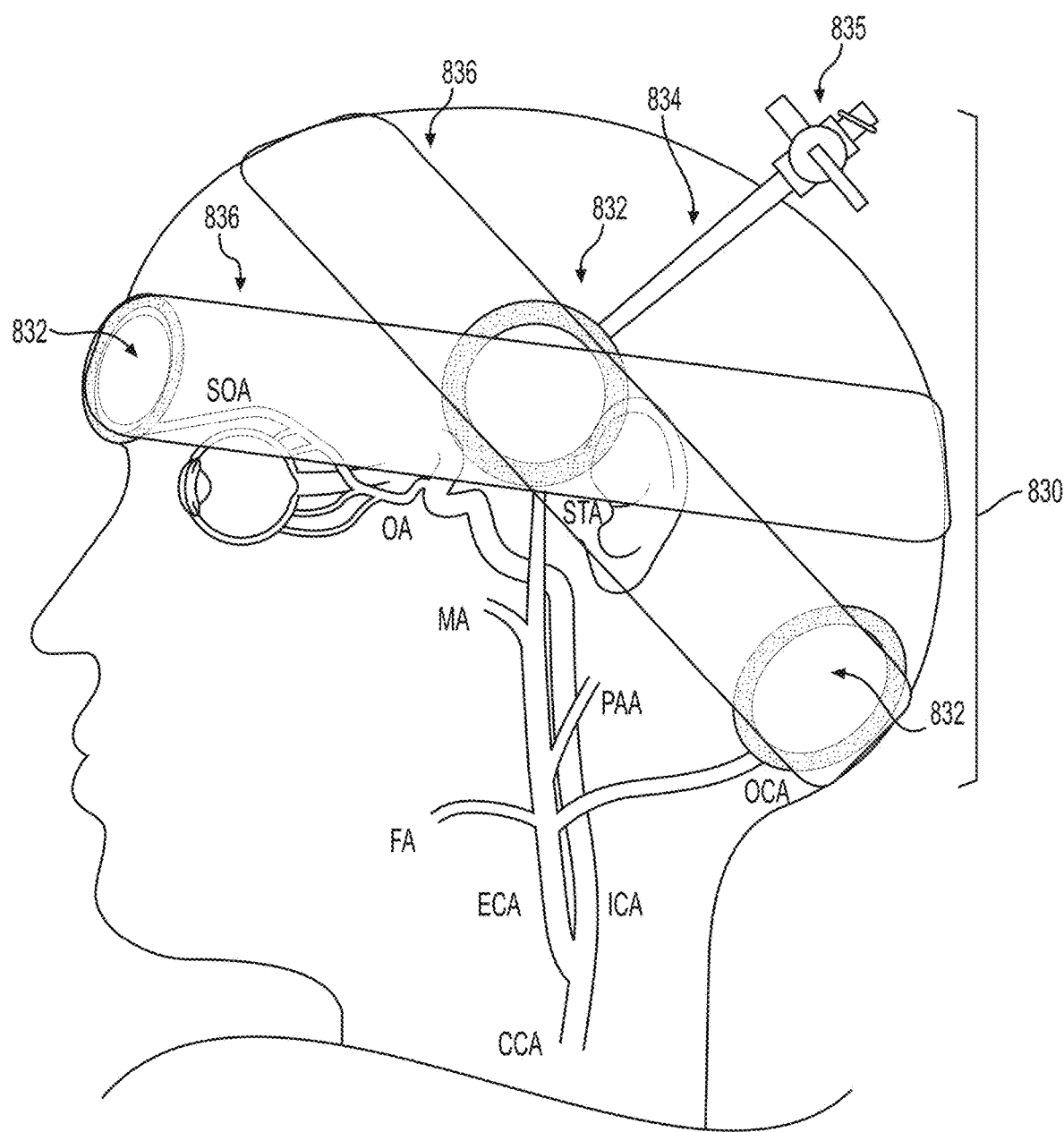

Also, with each of the access sites in the head, it may be desirable to provide an aid in site closure. As a way to automate manual pressure, compression headgear 830 may be used as shown in FIG. 32F. The compression headgear 830 may include a focal pressure applicator 832 and a headband 836. The focal pressure applicator 832 may comprise an inflatable pad connected to a syringe (not shown) by tubing 834 and stop-cock 835. The headband 836 may comprise an elastic strap and may incorporate an adjustment mechanism to loosen or tighten as desired. The compression headgear 830 may be placed to aid in closure of the SOA, the STA or OcA with the focal pressure applicator 832 positioned over the access site and the headband 836 placed diametrically relative thereto as shown.

The access sites in the head, in particular the STA approach, have a number of advantages in terms of speed, performance, safety and closure. With regard to speed, the shorter distance reduces time to reach the target anatomy. With regard to performance, the shorter distance allows for increased suction force and better manipulation of devices. With regard to safety, the shorter distance to the target anatomy avoids navigation of the aortic arch which may be laden with plaque giving rise to embolic and dissection risks. With regard to closure, the proximity of the STA to the skull reduces potential complications. Thus, the access sites in the head may provide benefits to procedures other than dilating the OA. For example, the access sites may be used for cerebrovascular procedures such as in the treatment of acute stroke with mechanical thrombectomy or aspiration devices. In addition, the access sites may be used for coronary procedures such as in the treatment of coronary artery disease with balloon angioplasty devices.

Oculofacial Approach

One of the challenges of the oculofacial approach is the small size of the supra-orbital artery and the supra-trochlear artery, which tend to be approximately 1.0+/−0.25 mm. Compared to a femoral approach where the femoral artery is approximately 7.0+/−0.5 mm at the access site, the oculofacial approach must be performed on a much smaller scale. However, it has several potential advantages. For example, whereas a femoral or radial approach requires navigation through the aortic arch and carotid arteries, the oculofacial approach does not, thus reducing the risk of an embolic event. Also, the oculofacial approach leads directly to the OA and doesn't require selective steering into side branches.

Figure 33A:
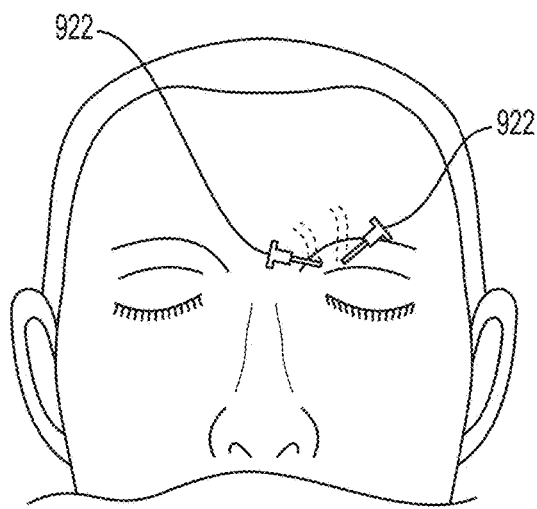
FIGS. 33A and 33B schematically illustrate an oculofacial approach.
Figure 33B:
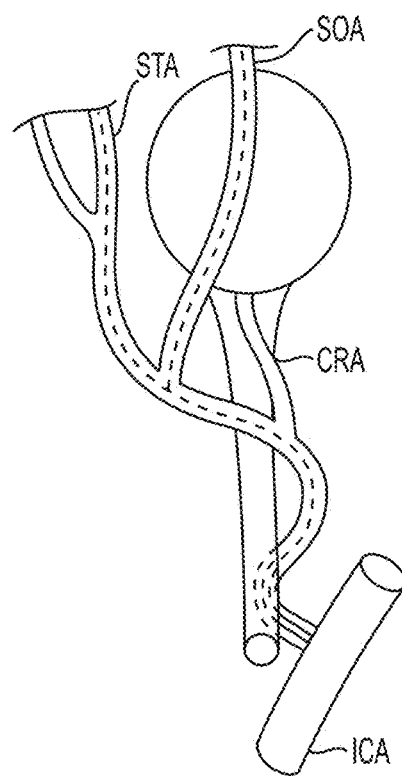
Figure 33C:
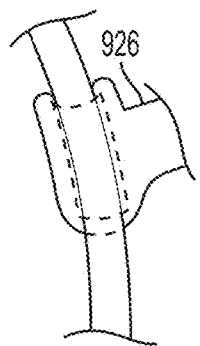
FIG. 33C schematically illustrates a tool to hold an oculofacial artery for cannulation.
Figure 33D:
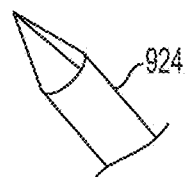
FIG. 33D schematically illustrates a trocar needle for accessing an oculofacial artery.

With reference to FIGS. 323-33D, the oculofacial approach is described in more detail. As seen in FIG. 33A, one or more of the arteries branching distally off of the ophthalmic artery (OA), such as the supra-orbital (SOA) artery or the supra-trochlear (STrA) artery, may be accessed subcutaneously near the eyebrow, and devices may be delivered in a retrograde direction to the OA, OA ostium or internal carotid artery (ICA) as seen in FIG. 33B. This approach may be used for diagnostic purposes such as retrograde injection of contrast media to enable x-ray visualization (e.g., angiography) the OA, OA ostium or ICA. This approach may also be used to establish reverse flow as described in co-pending U.S. patent application Ser. No. 16/583,508. Further, this approach may be used therapeutic purposes such as retrograde insertion of a balloon catheter 640 beyond the central retinal artery (CRA) to dilate the OA, OA ostium or ICA. Such uses of the oculofacial access site may be implemented alone or in combination.

In a percutaneous access technique, the SOA and/or the STrA may be palpated and a needle 924 may be inserted into the artery followed by a guidewire. The needle may be removed from the artery leaving the guidewire in place. An introducer sheath 922 may be placed over the guidewire to maintain access, and the guidewire may be removed to make room for other devices such as a different guidewire, microcatheter or balloon catheter to be inserted. Alternatively, the guidewire may be left in place and a microcatheter or balloon catheter may be inserted over it without the use of an introducer sheath, called a bareback technique. Because the SOA and STrA lead directly to the OA and the calibers of the SOA and STrA are so small, a bareback technique may be preferred (as compared to a femoral or radial approach that make use of introducers, sheaths and catheters for navigation). Under x-ray visualization, a balloon catheter or other therapeutic intravascular device may be advanced beyond the central retinal artery (CRA) to dilate the OA, OA ostium or ICA, for example.

In a cut-down access technique, the SOA and/or the STrA may be exposed through a skin incision. Under direct visualization, access to the SOA and/or the STrA may be accomplished with the aid of a support tool 926 having a handle and a sling in which the artery can rest as shown in FIG. 33C. Using a conventional needle, a scalpel or a trocar needle 924 as seen in FIG. 33D, the SOA and/or the STrA may be accessed. It may be helpful to advance the needle or trocar in one direction (e.g., retrograde) while applying traction in the opposite direction (e.g., antegrade). The bareback technique described before may then be used to advance a balloon catheter or other therapeutic intravascular device beyond the central retinal artery (CRA) to dilate the OA, OA ostium or ICA, for example, under x-ray visualization.

Figure 34A:
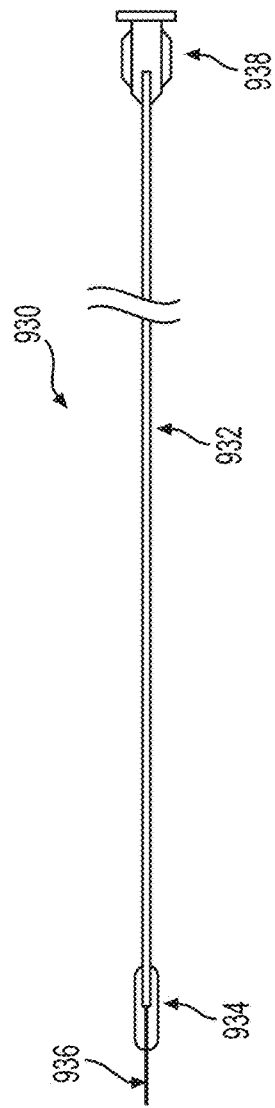
FIG. 34A is a schematic side partially-sectioned view of a fixed-wire balloon catheter for use in the oculofacial approach.
Figure 34B:
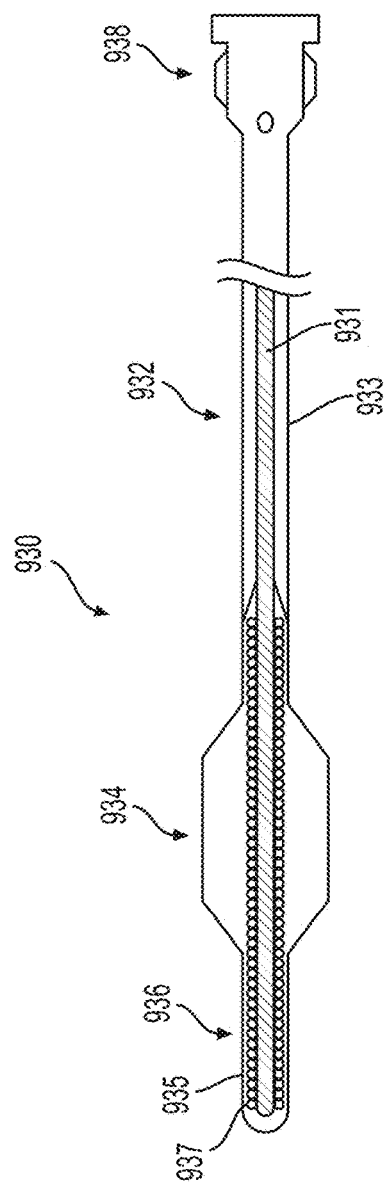
FIG. 34B is a more detailed schematic side sectional view of the fixed-wire balloon catheter shown in FIG. 34A.

In addition to making use of the bareback technique due to limited space inside the SOA and STrA, it may be desirable to make use of a fixed-wire balloon catheter 930 because it has a very low profile. FIGS. 34A and 34B are schematic illustrations of a fixed-wire balloon catheter 930 for the oculofacial approach. With reference to FIG. 34A, which shows a schematic side view of the fixed-wire catheter 930, the catheter may have an overall length sufficient to extend from the SOA or STrA accessed near the eyebrow to the ostium of the OA at the ICA, plus sufficient length for manipulation outside the body by the treating physician.

With reference to FIG. 34B, which shows a schematic side sectional view of the fixed-wire catheter, the catheter may generally include an elongate shaft 932 with a distally mounted balloon 934 and a flexible guidewire-like tip 936. The shaft 932 may comprise a core wire 931 over which the proximal waist 933 of the balloon 934 extends to a proximal hub 938 to define an annular inflation lumen therein. The core wire 931 may taper distally and a coil 937 of radiopaque wire may be disposed over the tapered core 931. A polymer jacket 935 may extend over the coil 937 and may be bonded to the core wire 931 proximal of the coil 937. The distal waist of the balloon 934 may be bonded to the polymer jacket 935 over the coil 937. By way of example, the balloon 934 may have a length of about 1.0-1.5 cm and distal tip 936 may have a length of about 10 mm. The distal tip 936 may have an outside diameter of about 0.008 inches, and the proximal shaft 932 may have an outside diameter of about 0.014 inches. The coil 937 length may be about 2.0 cm and the overall working length of the fixed-wire catheter 930 may be about 30 cm, and a hydrophilic coating may be applied to the shaft and optionally the balloon.

Figure 35G:
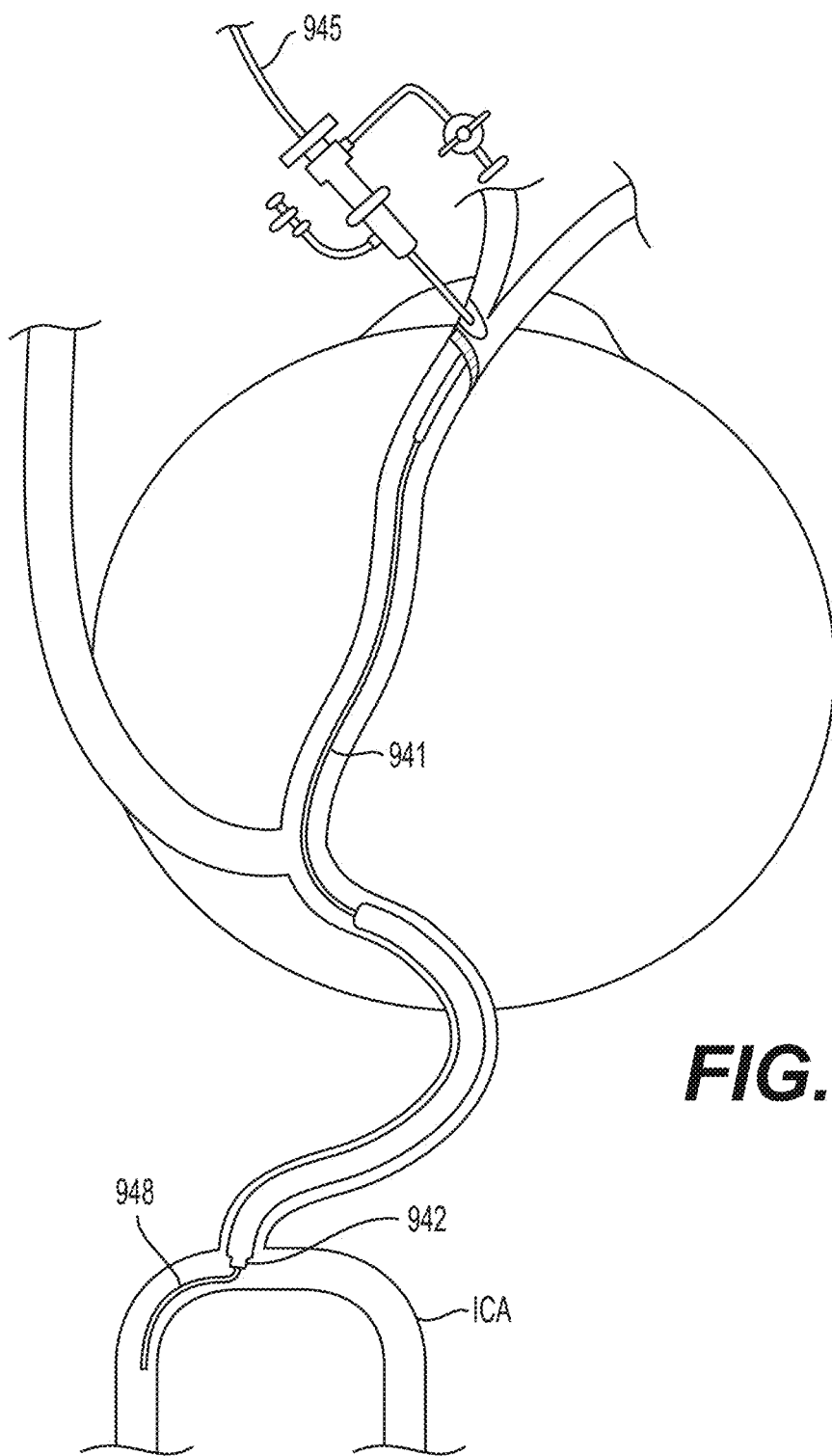
FIG. 35G schematically illustrates how the innerless over-the-wire balloon catheter shown in FIG. 35A may be used with the guidewire shown in FIG. 35C.

As an alternative to a fixed-wire balloon catheter, an innerless over-the-wire balloon catheter 940 may be used as schematically illustrated in FIGS. 35A-35G. The innerless over-the-wire balloon catheter 940 eliminates the need for a separate inner tube by providing a seal between the distal end of the balloon catheter 940 and the guidewire 945 as seen in FIG. 35A, which is a schematic cross-sectional view of the distal ends of the balloon catheter 940 and guidewire 945. As shown, the distal balloon 942 waist may include an inside collar 943 that fluidly seals to a raised part 947 of the guidewire. As shown in FIG. 35B, which is a schematic sectional view of the proximal end of the balloon catheter 940 and the guidewire 945, a Tuohy Borst fitting may seal onto a proximal portion of the guidewire 945 and may be connected to the proximal hub 944 of the balloon catheter 940 via a luer lock fitting (shown disconnected). Inflation and deflation of the balloon 942 may be facilitated by connecting a syringe (not shown) or the like to a side port of the Tuohy Borst fitting.

As seen in FIG. 35C, which is a schematic partially sectioned side view of the guidewire body 946 and tip 948, the guidewire 945 may comprise a standard design except for the provision of a raised portion 947 having a slightly larger diameter (e.g., 0.016 inches) than the guidewire shaft (e.g., 0.010 inches). The raised portion 947 may comprise a short SST hypotube or polyimide tube having an inside diameter of about 0.013 inches and a wall thickness of about 0.0015 inches boned to the guidewire proximal of the distal tip 948 of the guidewire 945, such as near the proximal end of the coiled tip 948, as shown in FIG. 35D which is a cross-sectional view taken along line B-B in FIG. 35C. As seen in FIG. 35E, which is a schematic sectioned side view of the balloon 942 and catheter shaft 941 distal portion, an inner collar 943 is provided at the distal end of the balloon 942 to seal onto the raised portion 947 of the guidewire 945 and eliminate the need for a separate inner tube. The proximal catheter shaft 941 may comprise a NiTi hypotube or 90AE polyurethane tubing having an outside diameter of about 0.021-0.022 inches. As shown in FIG. 35F which is a cross-sectional view taken along line A-A in FIG. 35E, the inner collar 943 may comprise an outer layer of 0.001 inch wall thickness polyether-block-amide or polyurethane over an inner layer of 0.0005-0.001 inch wall thickness polyimide tubing for a combined wall thickness of about 0.0015-0.002 inches, an inside diameter of 0.0165 inches and an outside diameter of about 0.0195 inches. The inner collar 943 may be bonded inside the distal waist of the balloon 942, which may be formed of a soft urethane extrusion have a wall thickness of 0.001 to 0.002 inches and an outside diameter of about 0.023-0.026 inches.

With reference to FIG. 35G, which is a schematic illustration of how the innerless over-the-wire balloon catheter 940 may be used, an access sheath is shown accessing the SOA, but may alternatively access the STrA. The guidewire 945 may be inserted into the access sheath followed by the innerless balloon catheter 940 thereover, or the guidewire 945 and innerless balloon catheter 940 may be inserted into the access sheath together. The guidewire 945 and innerless balloon catheter 940 may be advanced in the SOA or STrA to the OA until the distal end 948 of the guidewire 945 is disposed in the ICA. With the raised portion 947 of the guidewire 945 positioned just distal of the area to be dilated, such as the ostium of the OA to the ICA, and the inner collar 943 of the innerless balloon catheter 940 positioned on the raised portion 947 of the guidewire 945 to establish a fluid seal, the balloon 942 may be inflated to dilate a restriction is the OA, for example.

Figure 36A:
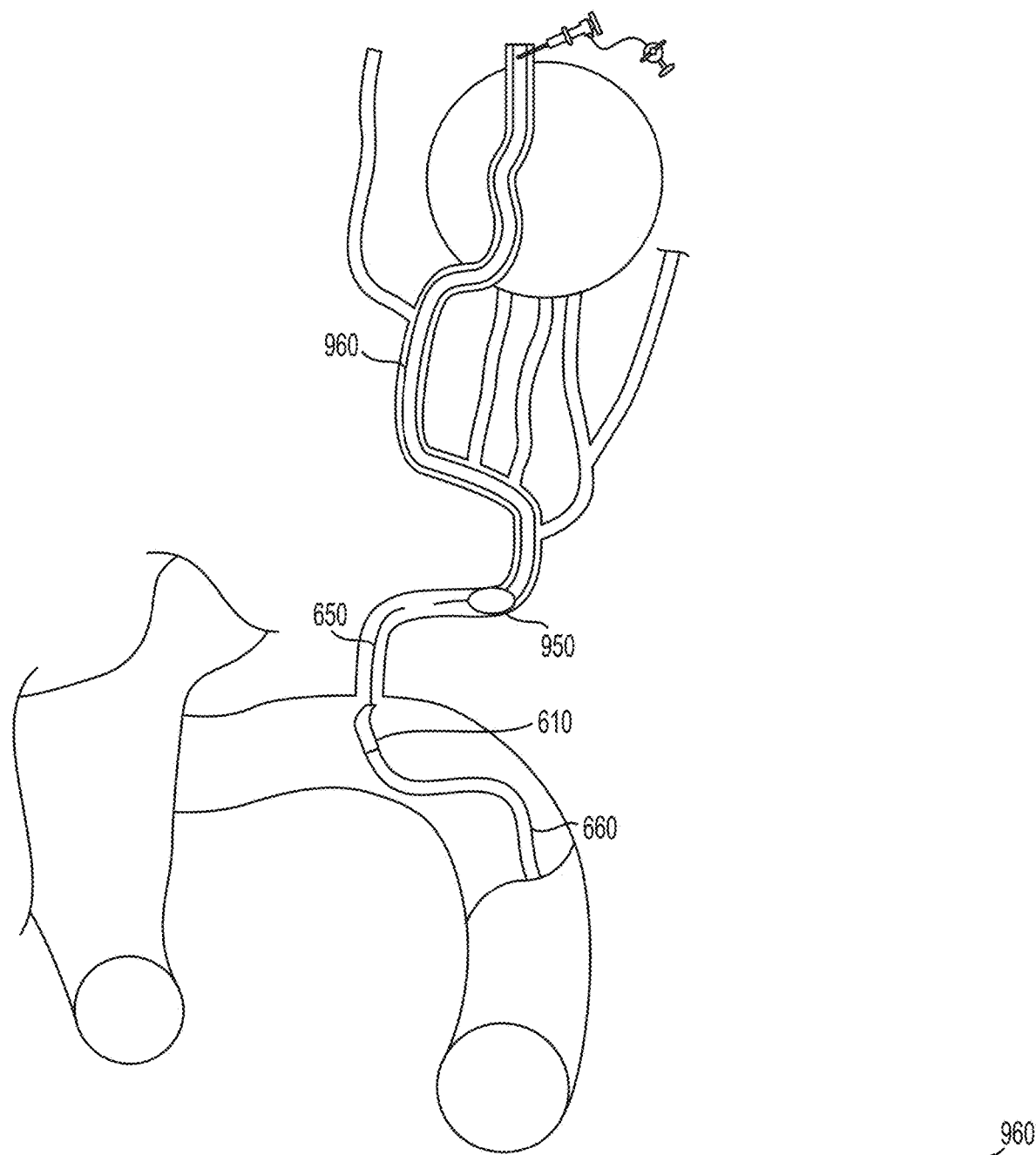
FIGS. 36A-36B are schematic illustrations of a combined femoral and oculofacial approach to stop antegrade flow in the ophthalmic artery, dilate the ophthalmic artery and aspirate if needed.
Figure 36B:
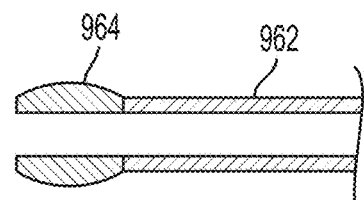

The oculofacial approach may be used in combination with a femoral or radial approach, an example of which is shown in FIG. 36A. The STrA and/or SOA may be accessed and cannulated with a microcatheter 960, which is similar to microcatheter 610 illustrated in FIG. 21A but foreshortened for the oculofacial approach. The microcatheter 960 may include a relatively larger soft bulbous tip 965 on the distal end of an elongate shaft 962 as shown in FIG. 36B. The microcatheter 960 may be positioned with its distal tip 964 in the OA beyond the branch to the CRA such as in the long limb of the OA. The microcatheter 960 may be used to deliver drugs, to inject contrast media or to aspirate the OA during and/or after balloon dilation by applying a proximal vacuum. An occlusion balloon catheter 950 may be inserted through the microcatheter 960 with the occlusion balloon positioned distal of the CRA such as in the long limb of the OA. The occlusion balloon catheter 950 may be used to stop antegrade flow in the OA by inflating the occlusion balloon, thereby mitigating emboli flowing into the CRA and potentially causing harm to the retina. By using the oculofacial retrograde approach for these purposes, the femoral or radial antegrade approach remains free to deliver the aiming intermediate catheter 660, microcatheter 610 or balloon catheter 640 (not shown) over guidewire 650 to deliver fluids or to dilate a proximal portion of the OA such as the ostium of the OA or the OA short limb.

Superficial Temporal Artery Approach

Figure 37:
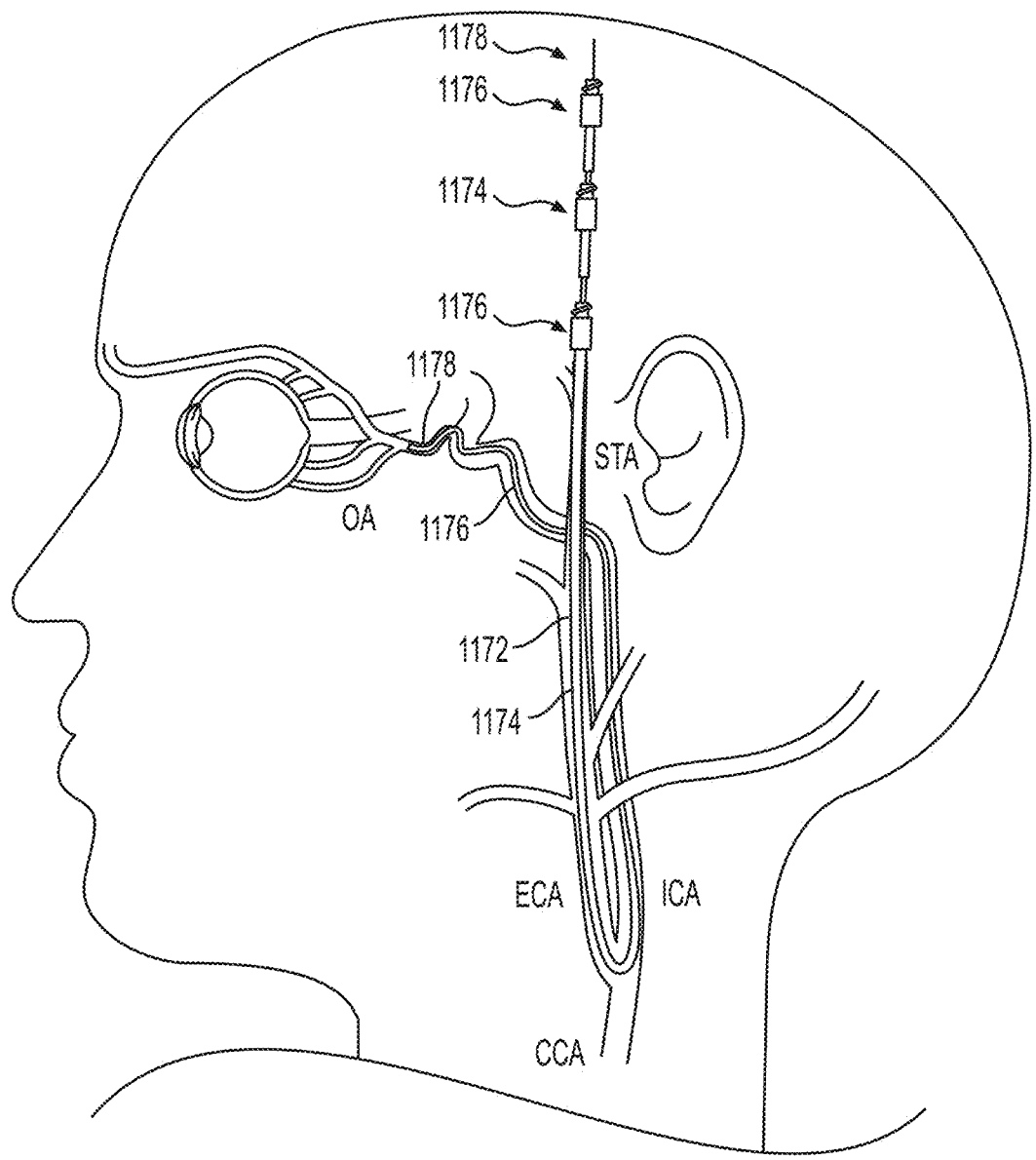
FIG. 37 schematically illustrates a superficial temporal artery access approach.

With reference to FIG. 37, examples of devices used for the STA access approach are shown schematically. A procedural sheath 1172 may be inserted into the STA over an 0.035" guidewire (not shown) having a knuckled end until the distal end of the procedural sheath 1172 is positioned near the ECA and the proximal end of the procedural sheath is positioned near the STA access site adjacent the tragus of the ear. A guide sheath 1174 may be inserted into the procedural sheath 1172 and navigated inferiorly down the ECA, around the carotid bifurcation to the ICA until the distal end of the guide sheath 1174 is positioned superiorly to the carotid bifurcation. Optionally, the guide sheath 1174 may be advanced through the STA and ECA without a procedural sheath 1172. Also, optionally, the guide sheath 1174 may be advanced over an obturator and guidewire as described later. A microcatheter 1176 may then be inserted into the guide sheath 1174 together with a guidewire 1178 and navigated superiorly in the ICA until the distal end of the microcatheter is positioned at or near the OA ostium. With the distal end of the microcatheter 1176 aimed toward the OA, the guidewire 1178 may be advanced until the distal end of the guidewire is inside the OA. The microcatheter 1176 may be removed leaving the guidewire 1178, guide sheath 1174 and procedural sheath in place. A balloon dilation catheter (not shown) as described previously may be advanced over the guidewire 1178 to the OA for dilation of a restriction therein.

Figure 38A:
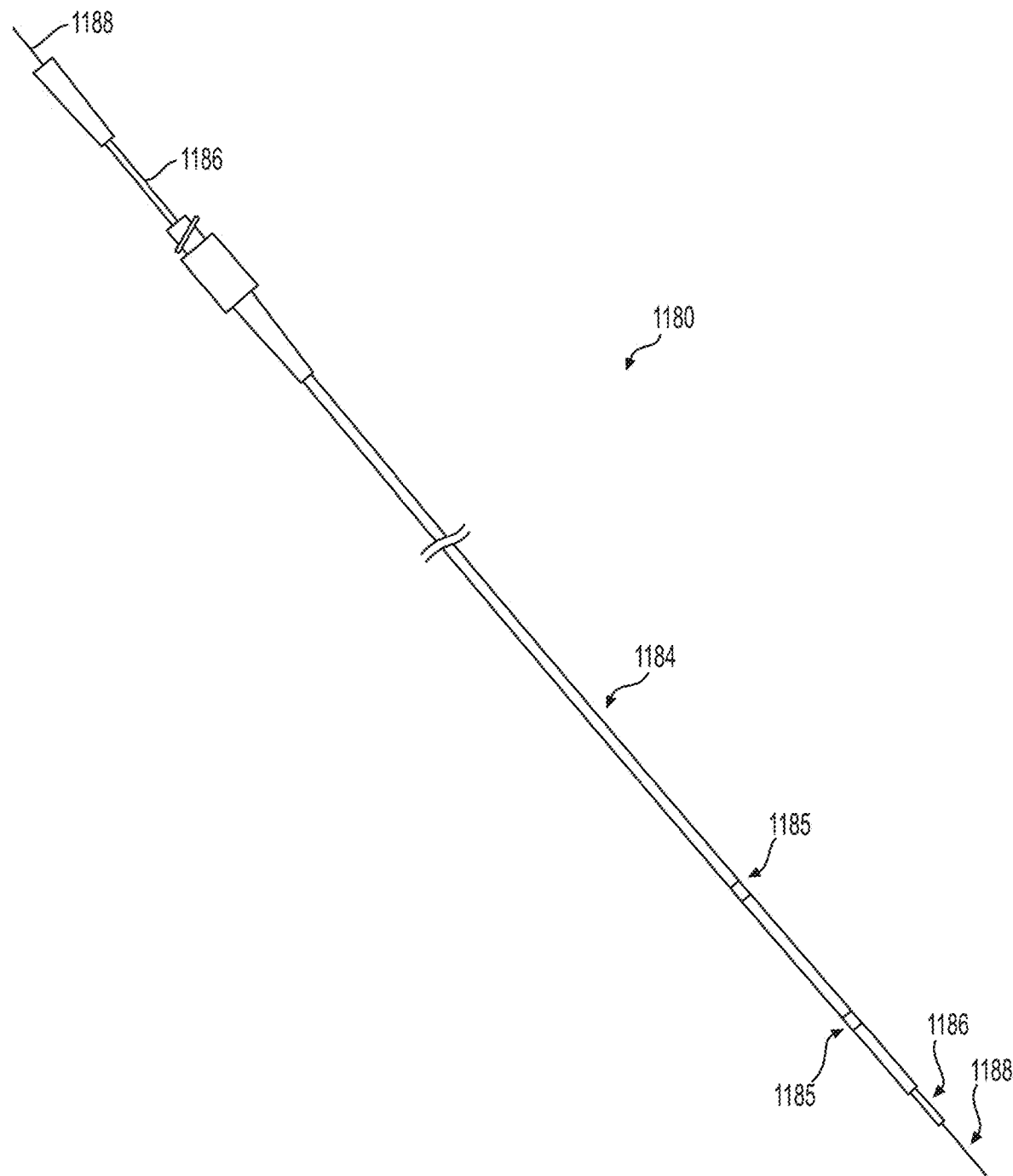
FIGS. 38A-38E schematically illustrated devices for use in the superficial temporal artery access approach.
Figures 38B, 38C:
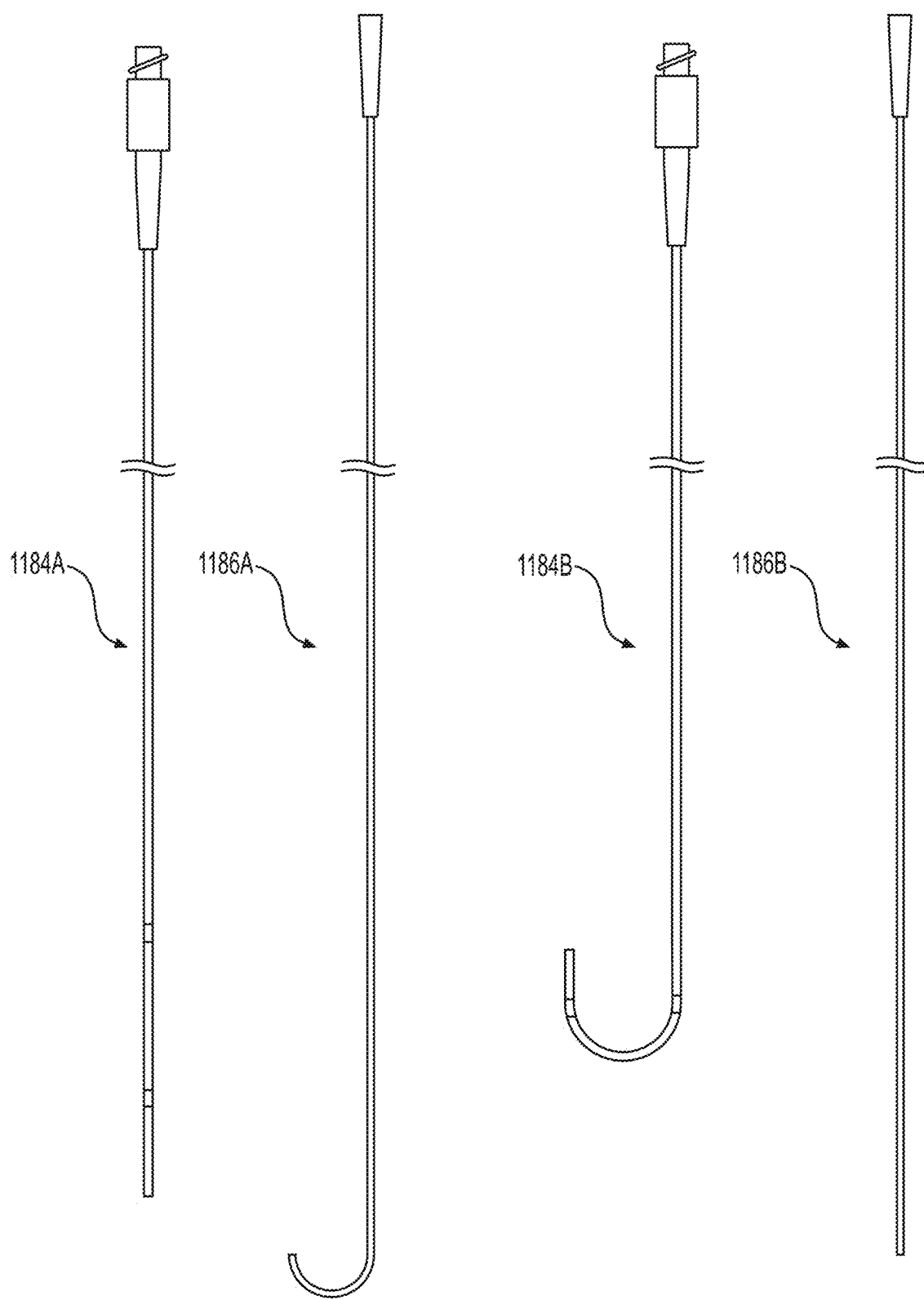

With reference to FIG. 38A, an example of a guide sheath 1180 system is shown schematically. The guide sheath 1180 system may be used with the STA approach described above. The guide sheath system 1180 may include a progressively flexible braid and/or coil reinforced tubular guide sheath 1184 placed over a tubular obturator 1186 placed over a guidewire 1188. To facilitate the "U" turn around the carotid bifurcation, the guide sheath system 1180 may use a straight guide sheath 1184A and a U-shaped obturator 1186A as shown in FIG. 38B. Alternatively, to facilitate the "U" turn around the carotid bifurcation, the guide sheath system 1180 may use a U-shaped guide sheath 1184B and a straight obturator 1186B as shown in FIG. 38C. With either embodiment, the obturator 1186 may be selectively advanced or retracted relative to the guide sheath 1184 to effectuate different curves while steering around the "U" turn at the carotid bifurcation. In both embodiments, the curve may be approximately 180+/−45 degrees with a radius of curvature of about 1.0 to 2.5 cm, by way of example, not necessarily limitation.

Figure 38D:
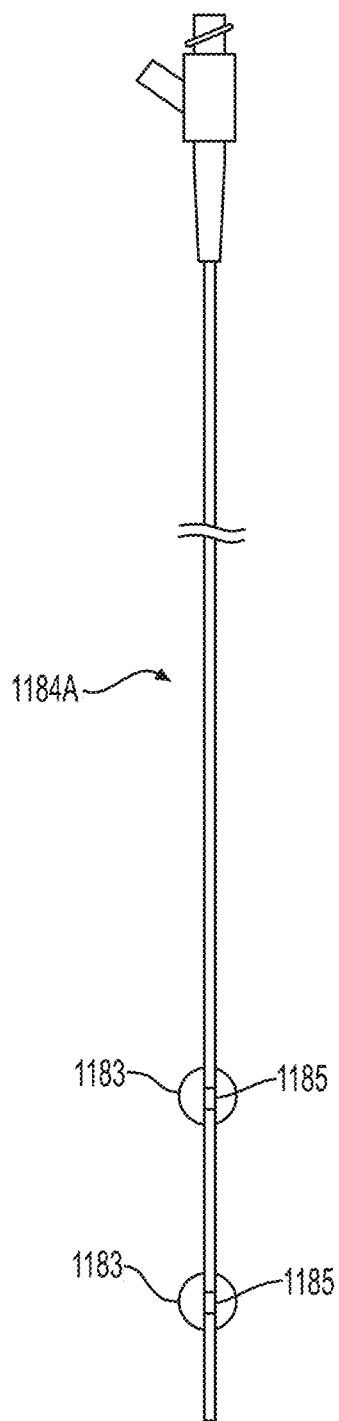
Figure 38E:
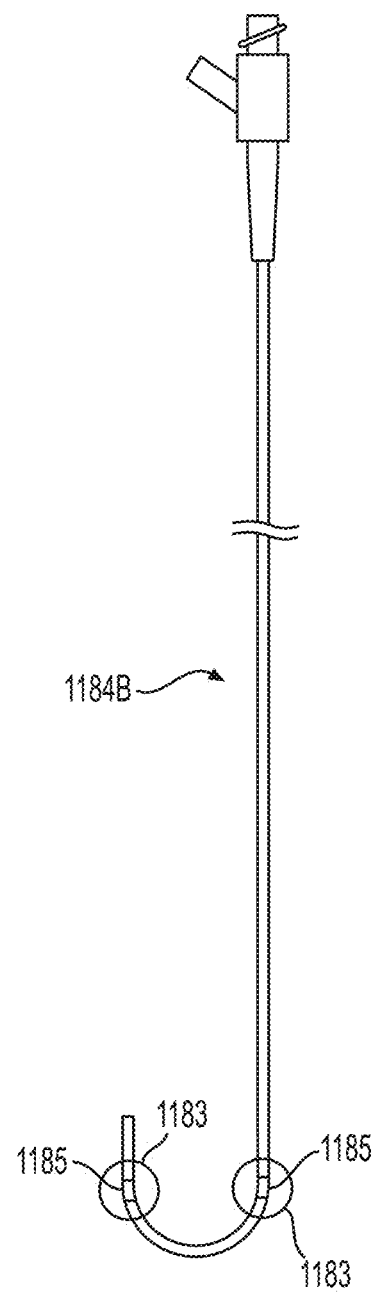

The guide sheath 1184 may be equipped with a pair of radiopaque marker bands 1185 that reside on the same transverse plane when the curve of the guide sheath 1184 is correctly positioned around the "U" turn at the carotid bifurcation. In addition, the guide sheath 1184 may include a pair of anchoring balloons 1183 similarly positioned as marker bands 1185. As shown in FIG. 38D, the anchoring balloons 1183 may be placed on a straight guide sheath 1184A, or, as shown in FIG. 38E, the anchoring balloons 1183 may be placed on a curved guide sheath 1184A. Inflation of the anchoring balloons 1183 secures the distal portion of the guide sheath 1184 across the carotid bifurcation such that devices advanced therethrough do not cause the guide sheath to back out of the ICA.

As an alternative the guide sheath 1184 include push/pull wires to provide a steerable tip. As a further alternative, the guide sheath 1184 may incorporate a straight or curved core wire disposed in a side lumen that may be advanced or retracted to adjust stiffness to provide additional support (core wire advanced) or flexibility (core wire retracted), and may include a curved shape to support the U-shaped curve around the carotid bifurcation.

By way of example, not necessarily limitation, the following steps describe the STA approach in more detail.

1) Locate the artery near the tragus of the ear.
2) Use ultrasound or echo to locate the artery for puncture.
3) Puncture the vessel with a Micro puncture kit (0.014" compatible).

4) Insert an 0.014" guidewire (that is predisposed to "knuckling", J-ing or prolapsing) through the micro puncture needle.
5) Knuckle or for a "J" at the distal end of the guidewire.
6) Spin the guidewire to track through the STA to the ECA and ultimately past the bifurcation into the CCA, using the wire to straighten extreme tortuosity along the vessel(s).
7) Remove the needle and insert a 5F/6F procedural sheath with dilator over the guidewire into the STA beyond any tortuosity that would prevent advancing subsequent devices.
8) Remove the dilator and guidewire leaving the procedural sheath in place. If the dilator was not able to be placed beyond tortuosity that would prevent subsequent device exchanges, leave the 0.014 guidewire in place in the CCA to maintain access.
9) Use below techniques to cross the carotid bifurcation
   a. Insert a guiding sheath, obturator and 0.021-0.025" angle tip guidewire, steer the guidewire into the ICA and follow the guidewire with the guide sheath.
   b. Optionally, two microcatheters or a microcatheter and guidewire may be used for additional rail support of the guiding sheath further into the ICA.
   c. Use either the curved-tip guide sheath with straight obturator or curved-tip obturator with straight guide sheath. As an alternative, use a steerable guiding sheath placed at the carotid bifurcation and point the internal lumen of the guide sheath preferentially towards the lumen of the ICA. As a further alternative, use a flow directed wire/catheter placed in the bifurcation and blood flow from the common carotid to preferentially steer the flow directed catheter from the ECA to the ICA, then use the flow directed catheter as a rail to deliver the guide sheath into the ICA.
   d. Verify the radiopaque markers are on one either side of the bifurcation. If the 0.014" guidewire was left in place to maintain access, track the guide sheath over the 0.014" guidewire into the CCA before swapping out to a 0.021"-0.025" guidewire.
   e. If the guide sheath incorporates inflatable anchoring balloons, inflate the balloons to stabilize the curve and provide flow cessation/allow aspiration during the intervention.
10) Advance a curved-tip aiming microcatheter into the guide sheath together with an 0.014 guidewire and navigated superiorly in the ICA until the distal end of the microcatheter is aimed at the OA ostium.
11) Advance the guidewire inside the OA.
12) Remove the microcatheter leaving the guidewire in place
13) Advance a balloon dilation catheter over the guidewire to the OA
14) Place balloon across restriction in OA and inflate.
15) Deflate balloon.
16) Remove devices in reverse order, optionally applying aspiration using guide sheath.
17) Close access site.

Identification of Dormant Photoreceptors

Figure 39:
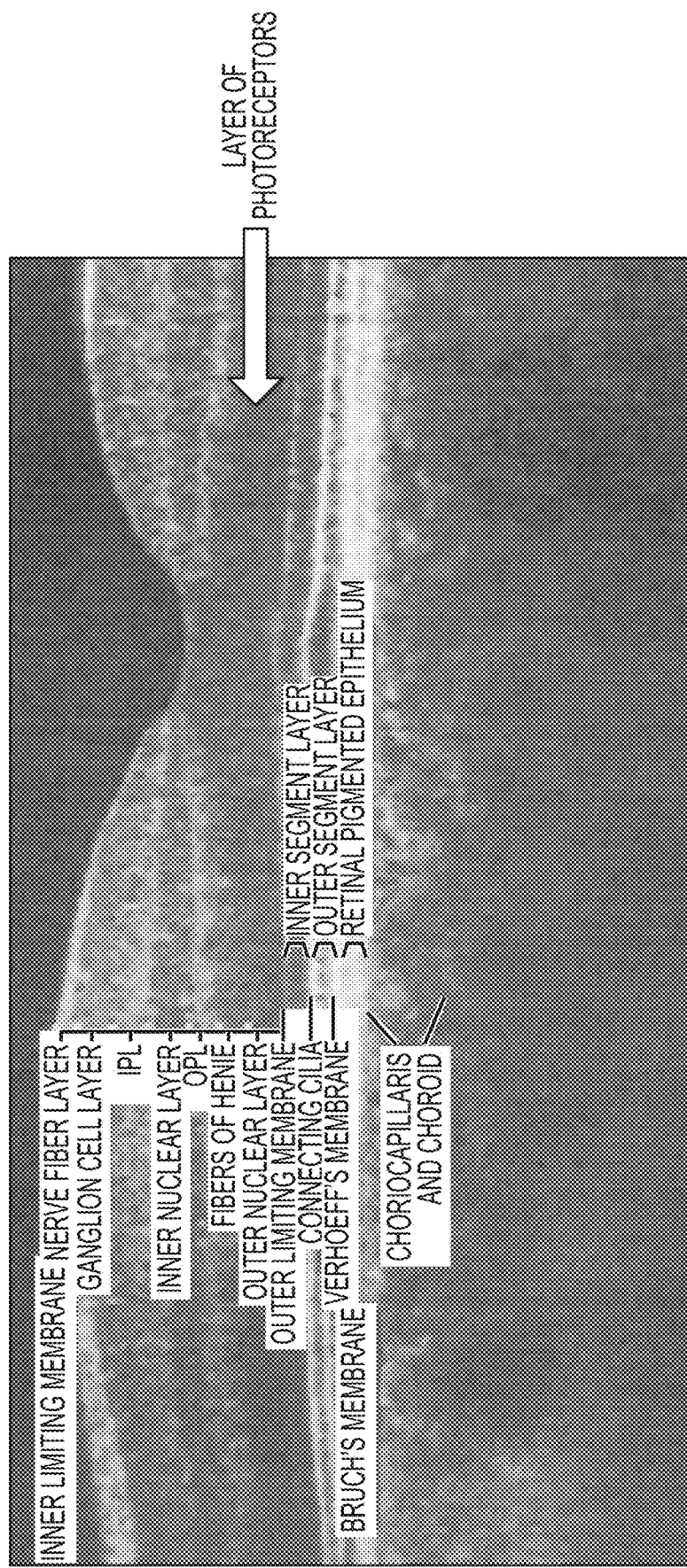
FIG. 39 is an OCT B Scan (e.g., cross-sectional) image showing various layers of the back of the eye.

Identification of dormant photoreceptors may be used as a diagnostic step before treating arterial disease in the vascular blood supply to the rear of the eye (e.g., restriction in OA ostium, OA short limb, etc.). If dormant photoreceptors are present, improving blood flow to the choroid may more likely be effective, as compared to photoreceptors that are atrophied or otherwise not dormant. As such, as a diagnostic step, if dormant photoreceptors are found to be present in a given patient, then the patient may be treated using the devices and methods described herein. Absent dormant photoreceptors, the patient may not be treated using the devices and methods described herein or may be treated with alternative methods. In this diagnostic method, Optical Coherence Tomography (OCT) may be used to identify the presence or absence of dormant photoreceptors in the macula. FIG. 39 shows the various tissue layers visible with OCT.

Figure 40:
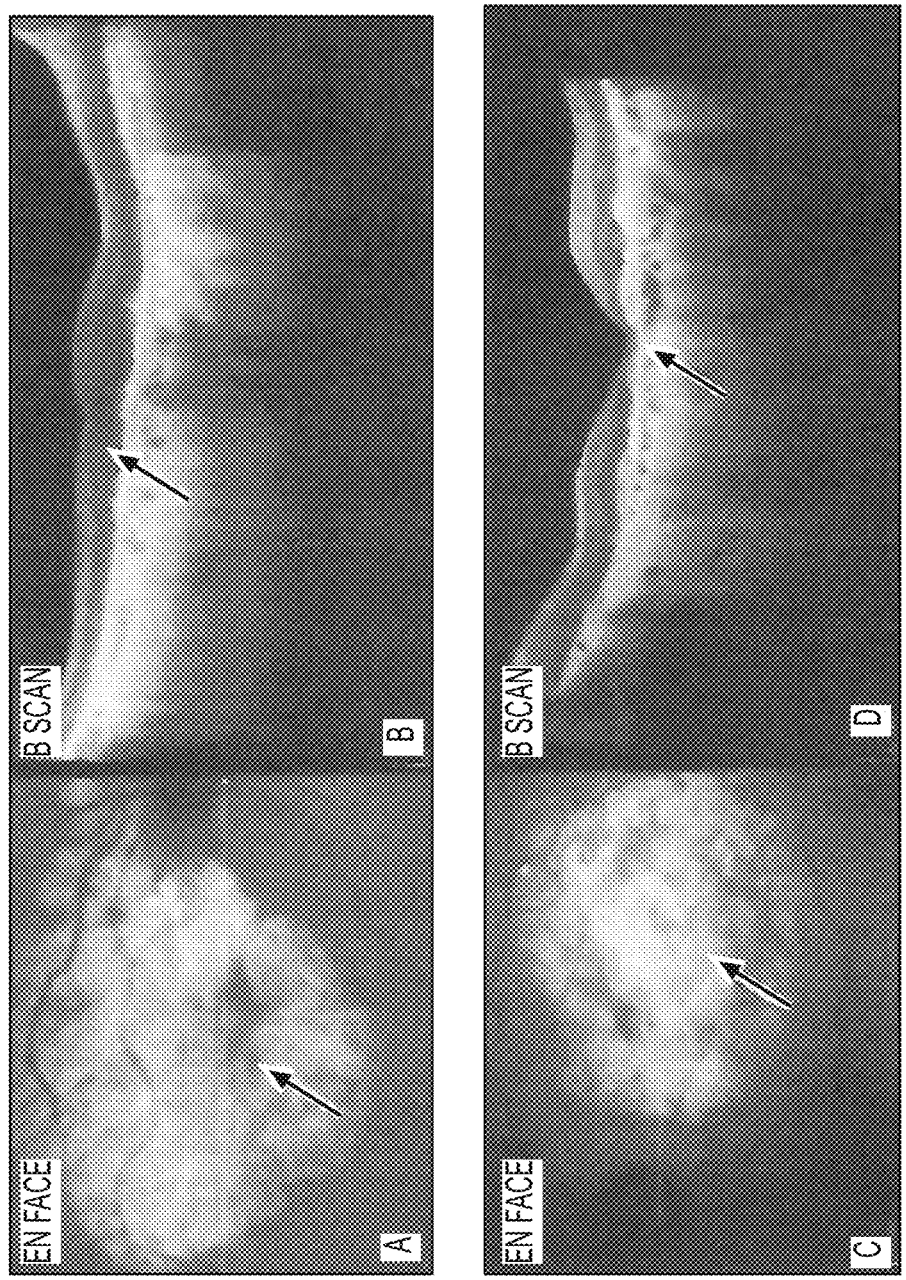
FIG. 40 is a series of En Face and B Scan (e.g., cross-sectional) OCT images.

The present method uses two forms of OCT to examine the fovea to look for possible dormant photoreceptors: en face OCT and B scan (e.g., cross-sectional) OCT as shown in FIG. 40. Geographic atrophy appears as a light segment in the macula when viewed by en face OCT. In severe cases, the majority of the macula may appear lighter than the surrounding retina. Darker spots or areas in the macula, in particular in the foveal section, may correlate to dormant photoreceptors. The first step is to take an en face OCT scan. An en face scan takes an image of the fovea, macula and majority of the retina looking directly at it. This scan will be examined to identify a 'darker' spot at the fovea as indicated by the white arrow in the top en face image (see FIG. 40 Panel A). If dormant photoreceptors (DP) are present, the central fovea will appear darker than the surrounding macula tissue. The next step is to take an B scan using OCT. The B scan takes a cross section of the eye tissue and includes the layers from the retina to the choroid. This scan is also used to identify dark areas of tissue just below the foveal pit as indicated by the white arrow in the top B scan image to the right (see FIG. 40 Panel B). In the event DP are not present, this will be indicated by an absence of a dark spot as noted by the white arrows in the en face and b scans on the bottom image as compared to the above scans (see FIG. 40 Panels C and D).

Figure 41:
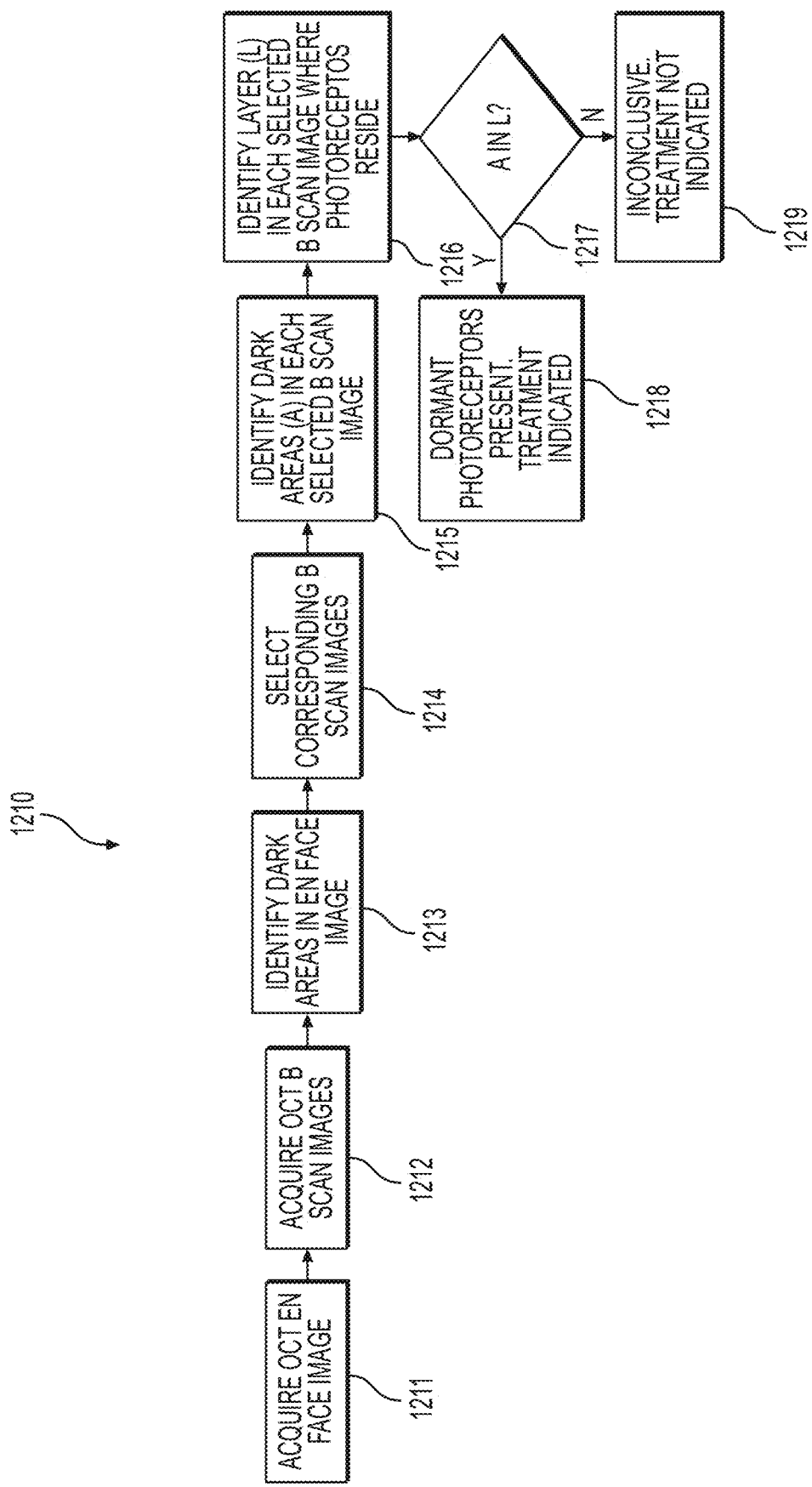
FIG. 41 is a flow chart of an automated process to determine if dormant photoreceptors are present and suitable for treatment.

The image comparison may be performed manually by a physician or OCT reader, or may be automated by an algorithm that examines each B scan, looks for the dark tissue segment, scans the en face image, looks for the dark tissue segment and then finally compares the two to calculate a likelihood of the presence of dormant photoreceptors. FIG. 41 shows a flow diagram of an example process algorithm 1210 that may be automated with software run by a computer. Initially, an en face OCT image is acquired 1211 of the patient's eye under evaluation for treatment by the devices and methods described herein. B scan images are then acquired 1212 from the same eye. Dark areas in en face image are then identified 1213. The corresponding B scan images (B scan slices that go through dark area in en face image) are then selected 1214. In each of the selected B scan images, dark areas (A) are identified 1215. Also, in each of the selected B scan images, the layer (L) is identified that contains photoreceptors 1216. A comparison 1217 is then made to determine if the dark areas (A) reside within the layer (L) containing the photoreceptors. If most of A resides in L, then dormant photoreceptors are present, and the treatment described herein may be indicated 1218. Otherwise, the treatment described herein may not be indicated 1219 and alternative treatment options may be sought.

We claim:
1. A method, comprising:
  accessing an artery in communication with an ophthalmic artery of a subject;
  advancing a balloon microcatheter along the accessed artery so as to align a distal end of the balloon microcatheter with an ostium of the ophthalmic artery, wherein the balloon microcatheter includes a lumen having a guidewire positioned therein;

proximally withdrawing the guidewire relative to the balloon microcatheter so as to enable a distal portion of the balloon microcatheter to assume a curved relaxed configuration;

cannulating the ostium with the distal portion of the balloon microcatheter when the distal portion is in the curved relaxed configuration; and performing a balloon dilation procedure by inflating a balloon of the balloon microcatheter within the ostium.

2. The method of claim 1, wherein the accessed artery is an internal carotid artery, and, during the balloon dilation procedure, a distal portion of the balloon is positioned within the ostium or the ophthalmic artery, while a proximal portion of the balloon is positioned within the internal carotid artery.

3. The method of claim 1, wherein, during the balloon dilation procedure, no portion of the balloon extends beyond a short limb of the ophthalmic artery.

4. The method of claim 1, wherein the balloon microcatheter includes a first wall defining a first lumen and a second wall defining a second lumen.

5. The method of claim 4, wherein the proximally withdrawing the guidewire includes proximally withdrawing the guidewire through the first lumen.

6. The method of claim 4, wherein an annular space between the first wall and the second wall defines an inflation lumen for the balloon.

7. The method of claim 1, wherein, in the curved relaxed configuration, a central longitudinal axis of the distal portion of the balloon microcatheter includes at least a first curve in a first direction and a second curve in a second direction different than the first direction.

8. The method of claim 7, wherein a radius of curvature of the first curve is larger than a radius of curvature of the second curve.

9. The method of claim 7, wherein in the curved relaxed configuration, the central longitudinal axis of the distal portion further includes a third curve.

10. The method of claim 7, wherein a radius of curvature of the first curve is larger than a radius of curvature of the second curve, and a radius of curvature of the second curve is larger than a radius of curvature of the third curve.

11. The method of claim 7, wherein a shape of the distal portion of the balloon microcatheter in the curved relaxed configuration corresponds to a shepherd's hook.

12. The method of claim 7, wherein the accessed artery is an internal carotid artery, and, when the distal portion of the balloon microcatheter assumes the curved relaxed configuration, the method further comprises seating the first curve in one of an ophthalmic segment or a communicating segment of the internal carotid artery, and seating the second curve in one of a clinoid segment or the ophthalmic segment of the internal carotid artery to stabilize the balloon microcatheter.

13. A method, comprising:

accessing an internal carotid artery in communication with an ophthalmic artery of a subject;

advancing a balloon microcatheter along the internal carotid artery so as to align a distal end of the balloon microcatheter with an ostium of the ophthalmic artery, wherein the balloon microcatheter includes a lumen having a guidewire positioned therein;

proximally withdrawing the guidewire relative to the balloon microcatheter so as to enable a distal portion of the balloon microcatheter to assume a curved relaxed configuration, wherein, in the curved relaxed configuration, a central longitudinal axis of the distal portion includes at least a first curve in a first direction and a second curve in a second direction different than the first direction;

cannulating the ostium with the distal portion of the balloon microcatheter when the distal portion is in the curved relaxed configuration; and performing an angioplasty procedure by inflating a balloon of the balloon microcatheter within the ostium, wherein, during the performing the angioplasty, no portion of the balloon extends beyond a short limb of the ophthalmic artery.

14. The method of claim 13, wherein, during the balloon dilation procedure, a distal portion of the balloon is positioned within the ostium or the ophthalmic artery, while a proximal portion of the balloon is positioned within the internal carotid artery.

15. The method of claim 13, wherein the lumen having the guidewire positioned therein is a first lumen, and wherein the balloon microcatheter includes a first wall defining the first lumen and a second wall defining a second lumen.

16. The method of claim 15, wherein the inflating the balloon includes delivering inflation fluid to the balloon via the second lumen, wherein the second lumen is arranged between the first wall and the second wall.

17. The method of claim 13, wherein a radius of curvature of the first curve is greater than a radius of curvature of the second curve.

18. The method of claim 13, wherein a shape of the distal portion of the balloon microcatheter in the curved relaxed configuration corresponds to a shepherd's hook.

19. The method of claim 13, wherein, when the distal portion of the balloon microcatheter assumes the curved relaxed configuration, the method further comprises seating the first curve in one of an ophthalmic segment or a communicating segment of the internal carotid artery, and seating the second curve in one of a clinoid segment or the ophthalmic segment of the internal carotid artery to stabilize the balloon microcatheter.

20. A method, comprising:

accessing an internal carotid artery in communication with an ophthalmic artery of a subject;

advancing a balloon microcatheter along the internal carotid artery so as to align a distal end of the balloon microcatheter with an ostium between the internal carotid artery and the ophthalmic artery, wherein the balloon microcatheter includes a lumen having a guidewire positioned therein;

proximally withdrawing the guidewire relative to the balloon microcatheter so as to enable a distal portion of the balloon microcatheter to assume a curved relaxed configuration, wherein, in the curved relaxed configuration, a central longitudinal axis of the distal portion includes at least a first curve in a first direction and a second curve in a second direction different than the first direction;

seating the first curve in one of an ophthalmic segment or a communicating segment of the internal carotid artery, and seating the second curve in one of a clinoid segment or an ophthalmic segment of the internal carotid artery to stabilize the balloon microcatheter;

cannulating the ostium via the distal portion of the balloon microcatheter when the distal portion is in the curved relaxed configuration; and performing an angioplasty procedure by inflating a balloon of the balloon microcatheter within the ostium, wherein, during the performing the angioplasty, a distal portion of the balloon is positioned within the ostium or the ophthalmic artery, a proximal portion of the balloon is positioned within the internal carotid artery, and no portion of the balloon extends beyond a short limb of the ophthalmic artery.

* * * * *